US011884716B2

(12) United States Patent
Gill et al.

(10) Patent No.: US 11,884,716 B2
(45) **Date of Patent: *Jan. 30, 2024**

(54) COMPOSITIONS AND METHODS OF PHOSPHOLIPASE A2 RECEPTOR CHIMERIC AUTOANTIBODY RECEPTOR T CELLS

(71) Applicant: THE TRUSTEES OF THE UNIVERSITY OF PENNSYLVANIA, Philadelphia, PA (US)

(72) Inventors: Saar Gill, Philadelphia, PA (US); Jonathan Hogan, Haddonfield, NJ (US); Aimee S. Payne, Merion Station, PA (US); Baomei Wang, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/543,429

(22) Filed: Dec. 6, 2021

(65) Prior Publication Data

US 2022/0098271 A1 Mar. 31, 2022

Related U.S. Application Data

(63) Continuation of application No. 17/051,248, filed as application No. PCT/US2019/030459 on May 2, 2019.

(60) Provisional application No. 62/665,863, filed on May 2, 2018.

(51) Int. Cl.

| | |
|---|---|
| ***C07K 16/18*** | (2006.01) |
| ***A61K 35/17*** | (2015.01) |
| ***C07K 14/705*** | (2006.01) |
| ***C07K 14/725*** | (2006.01) |

(52) U.S. Cl.

CPC .......... *C07K 14/7056* (2013.01); *A61K 35/17* (2013.01); *C07K 14/7051* (2013.01); *C07K 14/70517* (2013.01); *C07K 14/70578* (2013.01); *C07K 2319/02* (2013.01); *C07K 2319/03* (2013.01)

(58) Field of Classification Search

None

See application file for complete search history.

(56) References Cited

U.S. PATENT DOCUMENTS

| | | | | |
|---|---|---|---|---|
| 10,111,937 | B2 * | 10/2018 | Shayman ................ | A61P 11/00 |
| 11,266,717 | B2 * | 3/2022 | Zhu ......................... | A61P 13/12 |
| 2013/0287748 | A1 | 10/2013 | June et al. | |
| 2014/0010861 | A1 | 1/2014 | Bancel et al. | |
| 2017/0051035 | A1 | 2/2017 | Payne et al. | |

FOREIGN PATENT DOCUMENTS

| | | | |
|---|---|---|---|
| CN | 107663235 A | * | 2/2018 |
| WO | 1997040154 | | 10/1997 |
| WO | WO2012079000 A1 | * | 6/2012 |
| WO | 2013007640 | | 1/2013 |
| WO | WO2013044225 A1 | * | 3/2013 |
| WO | 2017009245 | | 1/2017 |
| WO | 2018031947 | | 2/2018 |
| WO | WO 2018/031947 | * | 2/2018 |
| WO | 2018127585 | | 7/2018 |

OTHER PUBLICATIONS

Incoming Written Opinion for U.S. Appl. No. 17/051,248, dated Sep. 16, 2019; pp. 1-7.*

Dotti et al., Design and Development of Therapies using Chimeric Antigen Receptor-Expressing T cells Immunol Rev. Jan. 2014; pp. 1-35.*

Seitz-Polski et al, "Epitope Spreading of Autoantibody Response to PLA2R Associates with Poor Prognosis in Membranous Nephropathy", J Am Soc Nephrol,, (Jan. 1, 2016), vol. 27, doi:10.1681/ASN.2014111061, pp. 1517-1533, XP002800680.

C. T. Ellebrecht et al, "Reengineering chimeric antigen receptor T cells for targeted therapy of autoimmune disease", Science, US, (Jul. 8, 2016), vol. 353, No. 6295, doi:10.1126/science.aaf6756, ISSN 0036-8075, pp. 179-184, XP055434542.

Beck et al, "M-Type Phospholipase A2 Receptor as Target Antigen in Idiopathic Membranous Nephropathy", The New England Journal of Medicine, US, (Jul. 2, 2009), vol. 361, No. 1, doi:10.1056/NEJMoa0810457, ISSN 0028-4793, pp. 11-21, XP055568290.

Dahan Karine et al, "Rituximab for Severe Membranous Nephropathy: A 6-Month Trial with Extended Follow-Up", Journal of the American Society of Nephrology, US, vol. 28, No. 1, doi:10.1681/ASN.2016040449, ISSN 1046-6673, (Jan. 1, 2017), pp. 348-358, URL: https://jasn.asnjournals.org/content/jnephrol/28/1/348.full.pdf?with-ds=yes, XP055867970.

Extended European Search Report for App. No. EP19796773.0, dated Dec. 10, 2021, 14 pages.

Stanescu, HC, et al., "Risk HLA-DQA1 and PLA2R1 alleles in idiopathic membranous nephropathy", N Engl J Med. Feb. 17, 2011;364(7):616-26.

(Continued)

*Primary Examiner* — Maria G Leavitt

(74) *Attorney, Agent, or Firm* — Saul Ewing LLP; Kathryn Doyle

(57) ABSTRACT

The invention includes compositions comprising at least one chimeric autoantibody receptor (CAAR) specific for an anti-phospholipase A2 receptor (PLA2R) autoantibody-based B cell receptor, polynucleotides encoding the CAAR, vectors comprising a polynucleotide encoding the CAAR, and recombinant T cells comprising the CAAR. The invention also includes methods of making a genetically modified cell, e.g., a genetically modified T cell, expressing a PLA2R-CAAR wherein the expressed CAAR comprises a PLA2R extracellular domain.

18 Claims, 12 Drawing Sheets

Specification includes a Sequence Listing.

(56) References Cited

OTHER PUBLICATIONS

Beck, LH Jr, et al.," M-type phospholipase A2 receptor as target antigen in idiopathic membranous nephropathy", N Engl J Med. Jul. 2, 2009;361(1):11-21.
GenBank Accession No. BC144631, Direct Submission: "*Homo sapiens* phospholipase A2 receptor 1, 180kDa, mRNA (cDNA clone MGC:178179 Image:9053162), complete cds", Jun. 12, 2007.
Enxiu Wang et al, "Generation of Potent T-cell Immunotherapy for Cancer Using DAP12-Based, Multichain, Chimeric Immunoreceptors", Cancer Immunol Res; 3(7) Jul. 2015.
Yarosz and Chang, "The Role of Reactive Oxygen Species in Regulating T Cell-mediated Immunity and Disease", Immune Network, vol. 18, No. 1, No. e14, published Feb. 22, 2018.
International Search Report for PCT International Application No. PCT/US19/030459 dated Sep. 16, 2019.
Augert, et al. "The M-type receptor PLA2R regulates senescence through the p53 pathway" (2009) EMBO Rep. 10:271-277.
Zheng Rongliang, et al., "10.1.3.3 Reactive oxygen species are involved in the signaling process of specific immune activation" Basics of Free Radical Medicine and Agriculture, p. 132, published in Nov. 2001.

* cited by examiner 4028 pTRPE.CysR-FNII-CTLD1-3.CD8H.BBz CAAR
(4028.CF123)

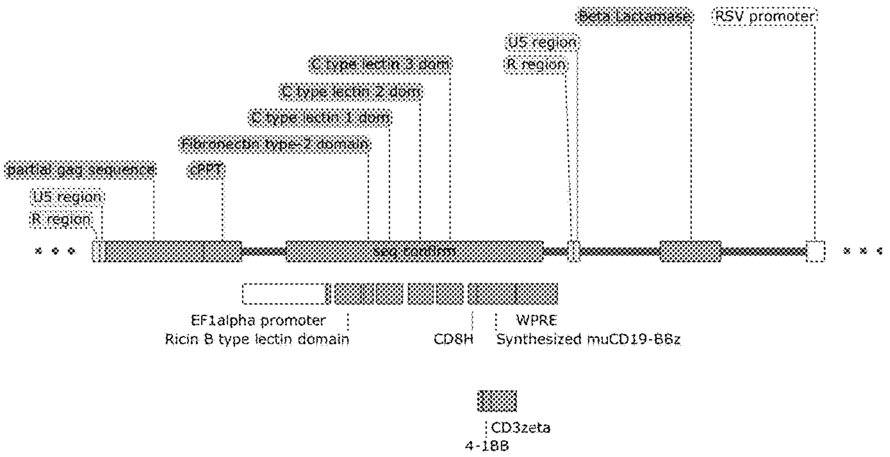

FIG. 3A

| Construct name | Vector used | Signal sequence | Propeptide | Spacer | nt sequence (complete CAAR) | aa sequence (PLA2R domains only) |
|---|---|---|---|---|---|---|
| 4025.C | pTRPE | native PLA2R | native PLA2R | CD8 hinge, aa 45 | Codon optimized, length 1182 | CysR aa 38-166 |
| C | pTRPE | Ig | none | CD8 hinge, aa 55 | Codon optimized, length 1167 | CysR aa 38-169 |
| 4026.CF1 | pTRPE | native PLA2R | native PLA2R | CD8 hinge, aa 45 | Codon optimized, length 1821 | CF1 aa 38-379 |
| CF1 | pTRPE | Ig | none | CD8 hinge, aa 55 | Codon optimized, length 1761 | CF1 aa 38-367 |
| 4027.CF12 | pTRPE | native PLA2R | native PLA2R | CD8 hinge, aa 45 | Codon optimized, length 2232 | CF12 aa 38-516 |
| 4028.CF123 | pTRPE | native PLA2R | native PLA2R | CD8 hinge, aa 45 | Codon optimized, length 2682 | CF123 aa 38-666 |
| CF123 | pTRPE | Ig | none | GS linker | Codon optimized, length 2490 | CF123 aa 38-653 |
| CF1237 | pTRPE | Ig | none | GS linker | Codon optimized, length 2910 | CF1237 aa 38-653, aa 1107-1246 |
| CF17 | pTRPE | Ig | none | GS linker | Codon optimized, length 2052 | CF17 aa 38-367, aa 1107-1246 |
| C17 | pTRPE | Ig | none | GS linker | Codon optimized, length 1893 | C17 aa 38-169, aa 223-367, aa 1107-1246 |

FIG. 3B

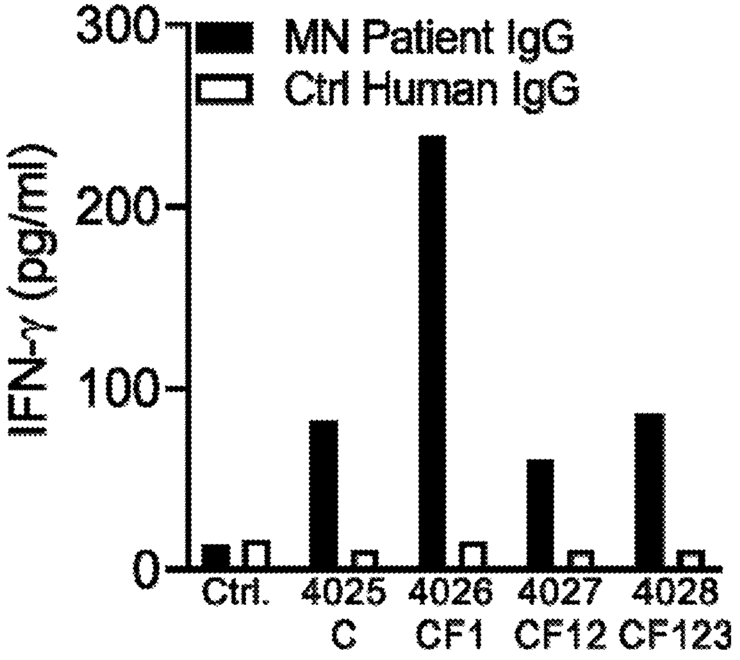
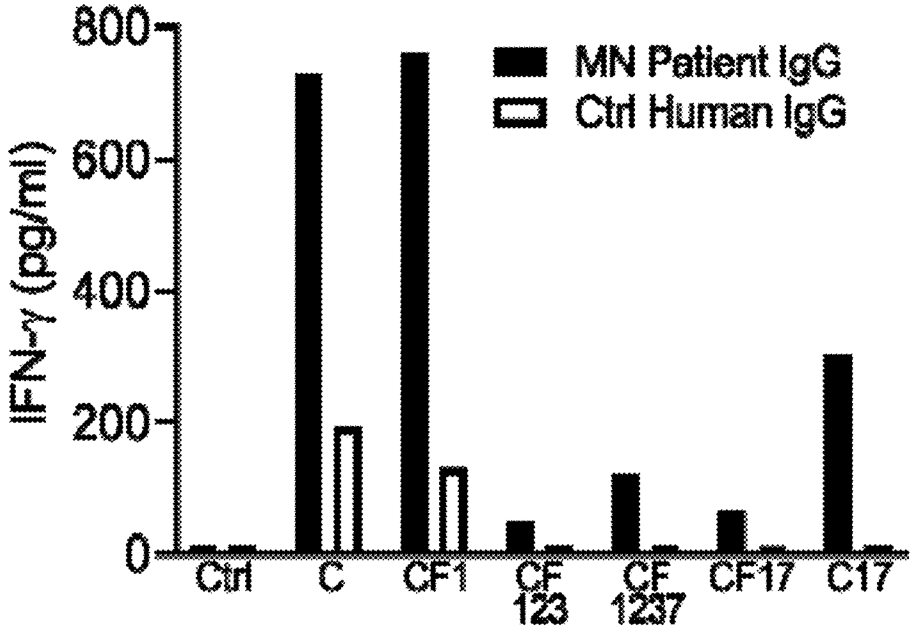
FIG. 9

SEQUENCE LISTING

```
<160> NUMBER OF SEQ ID NOS: 72

<210> SEQ ID NO 1
<211> LENGTH: 372
<212> TYPE: DNA
<213> ORGANISM: Artificial Sequence
<220> FEATURE:
<223> OTHER INFORMATION: CysR (Ricin B type lectin) domain

<400> SEQUENCE: 1

aagggcatct tcgtgatcca gagcgagagc ctgaagaagt gcatccaggc cggcaagagc      60

gtgctgaccc tggaaaattg caagcaggcc aacaagcaca tgctgtggaa atgggtgtcc     120

aaccacggcc tgttcaacat cggcggctct ggatgtctgg gcctgaattt ctctgcccct     180

gagcagcctc tgagcctgta cgagtgtgat agcaccctgg tgtccctgag atggcggtgc     240

aaccggaaga tgatcacagg ccctctgcag tactctgtgc aggtcgccca cgacaatacc     300

gtggtggcca gcagaaagta catccacaag tggatcagct acggcagcgg cggaggcgac     360

atctgtgaat ac                                                         372
```

-continued

<210> SEQ ID NO 2
<211> LENGTH: 33
<212> TYPE: DNA
<213> ORGANISM: Artificial Sequence
<220> FEATURE:
<223> OTHER INFORMATION: Linker

<400> SEQUENCE: 2
ctgcacaagg atctgcacac catcaagggc aac 33

<210> SEQ ID NO 3
<211> LENGTH: 147
<212> TYPE: DNA
<213> ORGANISM: Artificial Sequence
<220> FEATURE:
<223> OTHER INFORMATION: Fibronectin type-2 domain

<400> SEQUENCE: 3
acccacggaa tgccctgcat gttcccgttt cagtacaacc accagtggca ccacgagtgc 60
accagagaag gcagagagga cgacctgctt tggtgcgcca caaccagcag atacgagcgg 120
gatgagaagt ggggcttctg ccctgat 147

<210> SEQ ID NO 4
<211> LENGTH: 48
<212> TYPE: DNA
<213> ORGANISM: Artificial Sequence
<220> FEATURE:
<223> OTHER INFORMATION: Linker

<400> SEQUENCE: 4
cctacctctg ccgaagtggg ctgcgatacc atctgggaga aagacctg 48

<210> SEQ ID NO 5
<211> LENGTH: 354
<212> TYPE: DNA
<213> ORGANISM: Artificial Sequence
<220> FEATURE:
<223> OTHER INFORMATION: C-type lectin domain 1

<400> SEQUENCE: 5
aacagccaca tctgctacca gttcaacctg ctgtccagcc tgtcttggag cgaggcccac 60
agcagctgtc aaatgcaagg cggcacactg ctgagcatca ccgacgagac agaggaaaac 120
ttcatccgcg agcacatgag cagcaagacc gtggaagtgt ggatgggact gaaccagctg 180
gatgagcatg ccggatggca gtggagtgat ggcacccctc tgaactacct gaactggtcc 240
cctgaagtga acttcgagcc cttcgtggaa gatcactgcg gcaccttcag cagcttcatg 300
cccagcgctt ggagaagcag agactgcgag agcaccctgc cttacatctg caag 354

<210> SEQ ID NO 6
<211> LENGTH: 87
<212> TYPE: DNA
<213> ORGANISM: Artificial Sequence
<220> FEATURE:
<223> OTHER INFORMATION: Linker

<400> SEQUENCE: 6
aagtacctga accacatcga ccacgagatc gtggaaaagg acgcctggaa gtactacgcc 60
acacactgcg agcctggctg gaacccc 87

<210> SEQ ID NO 7
<211> LENGTH: 354
<212> TYPE: DNA

<213> ORGANISM: Artificial Sequence
<220> FEATURE:
<223> OTHER INFORMATION: C-type lectin domain 2

<400> SEQUENCE: 7
tacaaccgga actgctacaa gctgcagaaa gaggaaaaga cctggcacga ggccctgaga 60
agctgccagg ccgataatag cgccctgatc gacatcacaa gcctggccga ggtggaattt 120
ctggtcactc tgctgggcga cgagaacgcc tctgagacat ggatcggcct gtccagcaac 180
aagatccccg tgtccttcga gtggtccaac gacagcagcg tgatcttcac caactggcac 240
accctggaac ctcacatctt ccccaacaga tcccagctgt gtgtgtccgc cgagcagtct 300
gaaggccact ggaaagtgaa gaactgcgag gaacggctgt tctacatctg taaa 354

<210> SEQ ID NO 8
<211> LENGTH: 1395
<212> TYPE: DNA
<213> ORGANISM: Artificial Sequence
<220> FEATURE:
<223> OTHER INFORMATION: Extracellular domains of Construct 4027.CF12

<400> SEQUENCE: 8
aagggcatct tcgtgatcca gagcgagagc ctgaagaagt gcatccaggc cggcaagagc 60
gtgctgaccc tggaaaattg caagcaggcc aacaagcaca tgctgtggaa atgggtgtcc 120
aaccacggcc tgttcaacat cggcggctct ggatgtctgg gcctgaattt ctctgcccct 180
gagcagcctc tgagcctgta cgagtgtgat agcaccctgg tgtccctgag atggcggtgc 240
aaccggaaga tgatcacagg ccctctgcag tactctgtgc aggtcgccca cgacaatacc 300
gtggtggcca gcagaaagta catccacaag tggatcagct acggcagcgg cggaggcgac 360
atctgtgaat acctgcacaa ggatctgcac accatcaagg gcaacaccca cggaatgccc 420
tgcatgttcc cgtttcagta caaccaccag tggcaccacg agtgcaccag agaaggcaga 480
gaggacgacc tgctttggtg cgccacaacc agcagatacg agcgggatga gaagtggggc 540
ttctgccctg atcctacctc tgccgaagtg ggctgcgata ccatctggga gaaagacctg 600
aacagccaca tctgctacca gttcaacctg ctgtccagcc tgtcttggag cgaggcccac 660
agcagctgtc aaatgcaagg cggcacactg ctgagcatca ccgacgagac agaggaaaac 720
ttcatccgcg agcacatgag cagcaagacc gtggaagtgt ggatgggact gaaccagctg 780
gatgagcatg ccggatggca gtggagtgat ggcacccctc tgaactacct gaactggtcc 840
cctgaagtga acttcgagcc cttcgtggaa gatcactgcg gcaccttcag cagcttcatg 900
cccagcgctt ggagaagcag agactgcgag agcaccctgc cttacatctg caagaagtac 960
ctgaaccaca tcgaccacga gatcgtggaa aaggacgcct ggaagtacta cgccacacac 1020
tgcgagcctg gctggaaccc ctacaaccgg aactgctaca agctgcagaa agaggaaaag 1080
acctggcacg aggccctgag aagctgccag gccgataata gcgccctgat cgacatcaca 1140
agcctggccg aggtggaatt tctggtcact ctgctgggcg acgagaacgc ctctgagaca 1200
tggatcggcc tgtccagcaa caagatcccc gtgtccttcg agtggtccaa cgacagcagc 1260
gtgatcttca ccaactggca caccctggaa cctcacatct tccccaacag atcccagctg 1320
tgtgtgtccg ccgagcagtc tgaaggccac tggaaagtga agaactgcga ggaacggctg 1380
ttctacatct gtaaa 1395

<210> SEQ ID NO 9
<211> LENGTH: 48

<212> TYPE: DNA
<213> ORGANISM: Artificial Sequence
<220> FEATURE:
<223> OTHER INFORMATION: Linker

<400> SEQUENCE: 9
aaggccggcc acgtgctgtc cgatgccgag agtggatgtc aatccgga 48

<210> SEQ ID NO 10
<211> LENGTH: 132
<212> TYPE: DNA
<213> ORGANISM: Artificial Sequence
<220> FEATURE:
<223> OTHER INFORMATION: CD8 hinge domain

<400> SEQUENCE: 10
accacgacgc cagcgccgcg accaccaaca ccggcgccca ccatcgcgtc gcagcccctg 60
tccctgcgcc cagaggcgtg ccggccagcg gcggggggcg cagtgcacac gagggggctg 120
gacttcgcct gt 132

<210> SEQ ID NO 11
<211> LENGTH: 2232
<212> TYPE: DNA
<213> ORGANISM: Artificial Sequence
<220> FEATURE:
<223> OTHER INFORMATION: PLA2R-CAAR Construct 4027.CF12

<400> SEQUENCE: 11
atgctgctga gccctagcct gctgctgctc ctgcttcttg gagcccctag aggatgtgcc 60
ggatctgaag gtgttgccgc cgctctgaca cccgagagac tgctggaatg gcaggacaag 120
ggcatcttcg tgatccagag cgagagcctg aagaagtgca tccaggccgg caagagcgtg 180
ctgaccctgg aaaattgcaa gcaggccaac aagcacatgc tgtggaaatg ggtgtccaac 240
cacggcctgt tcaacatcgg cggctctgga tgtctgggcc tgaatttctc tgcccctgag 300
cagcctctga gcctgtacga gtgtgatagc accctggtgt ccctgagatg gcggtgcaac 360
cggaagatga tcacaggccc tctgcagtac tctgtgcagg tcgcccacga caataccgtg 420
gtggccagca gaaagtacat ccacaagtgg atcagctacg gcagcggcgg aggcgacatc 480
tgtgaatacc tgcacaagga tctgcacacc atcaagggca acacccacgg aatgccctgc 540
atgttcccgt ttcagtacaa ccaccagtgg caccacgagt gcaccagaga aggcagagag 600
gacgacctgc tttggtgcgc cacaaccagc agatacgagc gggatgagaa gtggggcttc 660
tgccctgatc ctacctctgc cgaagtgggc tgcgatacca tctgggagaa agacctgaac 720
agccacatct gctaccagtt caacctgctg tccagcctgt cttggagcga ggcccacagc 780
agctgtcaaa tgcaaggcgg cacactgctg agcatcaccg acgagacaga ggaaaacttc 840
atccgcgagc acatgagcag caagaccgtg gaagtgtgga tgggactgaa ccagctggat 900
gagcatgccg gatggcagtg gagtgatggc accccctctga actacctgaa ctggtcccct 960
gaagtgaact tcgagccctt cgtggaagat cactgcggca ccttcagcag cttcatgccc 1020
agcgcttgga gaagcagaga ctgcgagagc accctgcctt acatctgcaa gaagtacctg 1080
aaccacatcg accacgagat cgtggaaaag gacgcctgga agtactacgc cacacactgc 1140
gagcctggct ggaaccccta caaccggaac tgctacaagc tgcagaaaga ggaaaagacc 1200
tggcacgagg ccctgagaag ctgccaggcc gataatagcg ccctgatcga catcacaagc 1260
ctggccgagg tggaatttct ggtcactctg ctgggcgacg agaacgcctc tgagacatgg 1320

```
atcggcctgt ccagcaacaa gatccccgtg tccttcgagt ggtccaacga cagcagcgtg   1380

atcttcacca actggcacac cctggaacct cacatcttcc ccaacagatc ccagctgtgt   1440

gtgtccgccg agcagtctga aggccactgg aaagtgaaga actgcgagga acggctgttc   1500

tacatctgta aaaaggccgg ccacgtgctg tccgatgccg agagtggatg tcaatccgga   1560

accacgacgc cagcgccgcg accaccaaca ccggcgccca ccatcgcgtc gcagcccctg   1620

tccctgcgcc cagaggcgtg ccggccagcg gcggggggcg cagtgcacac gagggggctg   1680

gacttcgcct gtgatatcta catctgggcg cccttggccg ggacttgtgg ggtccttctc   1740

ctgtcactgg ttatcaccct ttactgcaaa cggggcagaa agaaactcct gtatatattc   1800

aaacaaccat ttatgagacc agtacaaact actcaagagg aagatggctg tagctgccga   1860

tttccagaag aagaagaagg aggatgtgaa ctgagagtga agttcagcag gagcgcagac   1920

gcccccgcgt acaagcaggg ccagaaccag ctctataacg agctcaatct aggacgaaga   1980

gaggagtacg atgttttgga caagagacgt ggccgggacc ctgagatggg gggaaagccg   2040

agaaggaaga accctcagga aggcctgtac aatgaactgc agaaagataa gatggcggag   2100

gcctacagtg agattgggat gaaaggcgag cgccggaggg gcaaggggca cgatggcctt   2160

taccagggtc tcagtacagc caccaaggac acctacgacg cccttcacat gcaggccctg   2220

cccctcgct aa                                                         2232


<210> SEQ ID NO 12
<211> LENGTH: 743
<212> TYPE: PRT
<213> ORGANISM: Artificial Sequence
<220> FEATURE:
<223> OTHER INFORMATION: PLA2R-CAAR Construct 4027.CF12

<400> SEQUENCE: 12

Met Leu Leu Ser Pro Ser Leu Leu Leu Leu Leu Leu Leu Gly Ala Pro
1               5                   10                  15

Arg Gly Cys Ala Gly Ser Glu Gly Val Ala Ala Ala Leu Thr Pro Glu
            20                  25                  30

Arg Leu Leu Glu Trp Gln Asp Lys Gly Ile Phe Val Ile Gln Ser Glu
        35                  40                  45

Ser Leu Lys Lys Cys Ile Gln Ala Gly Lys Ser Val Leu Thr Leu Glu
    50                  55                  60

Asn Cys Lys Gln Ala Asn Lys His Met Leu Trp Lys Trp Val Ser Asn
65                  70                  75                  80

His Gly Leu Phe Asn Ile Gly Gly Ser Gly Cys Leu Gly Leu Asn Phe
                85                  90                  95

Ser Ala Pro Glu Gln Pro Leu Ser Leu Tyr Glu Cys Asp Ser Thr Leu
            100                 105                 110

Val Ser Leu Arg Trp Arg Cys Asn Arg Lys Met Ile Thr Gly Pro Leu
        115                 120                 125

Gln Tyr Ser Val Gln Val Ala His Asp Asn Thr Val Val Ala Ser Arg
    130                 135                 140

Lys Tyr Ile His Lys Trp Ile Ser Tyr Gly Ser Gly Gly Gly Asp Ile
145                 150                 155                 160

Cys Glu Tyr Leu His Lys Asp Leu His Thr Ile Lys Gly Asn Thr His
                165                 170                 175

Gly Met Pro Cys Met Phe Pro Phe Gln Tyr Asn His Gln Trp His His
            180                 185                 190

Glu Cys Thr Arg Glu Gly Arg Glu Asp Asp Leu Leu Trp Cys Ala Thr
```

-continued

```
        195                 200                 205

Thr Ser Arg Tyr Glu Arg Asp Glu Lys Trp Gly Phe Cys Pro Asp Pro
    210                 215                 220

Thr Ser Ala Glu Val Gly Cys Asp Thr Ile Trp Glu Lys Asp Leu Asn
225                 230                 235                 240

Ser His Ile Cys Tyr Gln Phe Asn Leu Leu Ser Ser Leu Ser Trp Ser
                245                 250                 255

Glu Ala His Ser Ser Cys Gln Met Gln Gly Gly Thr Leu Leu Ser Ile
            260                 265                 270

Thr Asp Glu Thr Glu Glu Asn Phe Ile Arg Glu His Met Ser Ser Lys
        275                 280                 285

Thr Val Glu Val Trp Met Gly Leu Asn Gln Leu Asp Glu His Ala Gly
    290                 295                 300

Trp Gln Trp Ser Asp Gly Thr Pro Leu Asn Tyr Leu Asn Trp Ser Pro
305                 310                 315                 320

Glu Val Asn Phe Glu Pro Phe Val Glu Asp His Cys Gly Thr Phe Ser
                325                 330                 335

Ser Phe Met Pro Ser Ala Trp Arg Ser Arg Asp Cys Glu Ser Thr Leu
            340                 345                 350

Pro Tyr Ile Cys Lys Lys Tyr Leu Asn His Ile Asp His Glu Ile Val
        355                 360                 365

Glu Lys Asp Ala Trp Lys Tyr Tyr Ala Thr His Cys Glu Pro Gly Trp
    370                 375                 380

Asn Pro Tyr Asn Arg Asn Cys Tyr Lys Leu Gln Lys Glu Glu Lys Thr
385                 390                 395                 400

Trp His Glu Ala Leu Arg Ser Cys Gln Ala Asp Asn Ser Ala Leu Ile
                405                 410                 415

Asp Ile Thr Ser Leu Ala Glu Val Glu Phe Leu Val Thr Leu Leu Gly
            420                 425                 430

Asp Glu Asn Ala Ser Glu Thr Trp Ile Gly Leu Ser Ser Asn Lys Ile
        435                 440                 445

Pro Val Ser Phe Glu Trp Ser Asn Asp Ser Ser Val Ile Phe Thr Asn
    450                 455                 460

Trp His Thr Leu Glu Pro His Ile Phe Pro Asn Arg Ser Gln Leu Cys
465                 470                 475                 480

Val Ser Ala Glu Gln Ser Glu Gly His Trp Lys Val Lys Asn Cys Glu
                485                 490                 495

Glu Arg Leu Phe Tyr Ile Cys Lys Lys Ala Gly His Val Leu Ser Asp
            500                 505                 510

Ala Glu Ser Gly Cys Gln Ser Gly Thr Thr Thr Pro Ala Pro Arg Pro
        515                 520                 525

Pro Thr Pro Ala Pro Thr Ile Ala Ser Gln Pro Leu Ser Leu Arg Pro
    530                 535                 540

Glu Ala Cys Arg Pro Ala Ala Gly Gly Ala Val His Thr Arg Gly Leu
545                 550                 555                 560

Asp Phe Ala Cys Asp Ile Tyr Ile Trp Ala Pro Leu Ala Gly Thr Cys
                565                 570                 575

Gly Val Leu Leu Leu Ser Leu Val Ile Thr Leu Tyr Cys Lys Arg Gly
            580                 585                 590

Arg Lys Lys Leu Leu Tyr Ile Phe Lys Gln Pro Phe Met Arg Pro Val
        595                 600                 605

Gln Thr Thr Gln Glu Glu Asp Gly Cys Ser Cys Arg Phe Pro Glu Glu
    610                 615                 620
```

```
Glu Glu Gly Gly Cys Glu Leu Arg Val Lys Phe Ser Arg Ser Ala Asp
625                 630                 635                 640

Ala Pro Ala Tyr Lys Gln Gly Gln Asn Gln Leu Tyr Asn Glu Leu Asn
                645                 650                 655

Leu Gly Arg Arg Glu Glu Tyr Asp Val Leu Asp Lys Arg Arg Gly Arg
            660                 665                 670

Asp Pro Glu Met Gly Gly Lys Pro Arg Arg Lys Asn Pro Gln Glu Gly
        675                 680                 685

Leu Tyr Asn Glu Leu Gln Lys Asp Lys Met Ala Glu Ala Tyr Ser Glu
    690                 695                 700

Ile Gly Met Lys Gly Glu Arg Arg Arg Gly Lys Gly His Asp Gly Leu
705                 710                 715                 720

Tyr Gln Gly Leu Ser Thr Ala Thr Lys Asp Thr Tyr Asp Ala Leu His
                725                 730                 735

Met Gln Ala Leu Pro Pro Arg
            740
```

<210> SEQ ID NO 13
<211> LENGTH: 57
<212> TYPE: DNA
<213> ORGANISM: Artificial Sequence
<220> FEATURE:
<223> OTHER INFORMATION: Linker

<400> SEQUENCE: 13

```
aaggccggcc acgtgctgtc cgatgccgag agtggatgtc aagaaggctg ggagaga        57
```

<210> SEQ ID NO 14
<211> LENGTH: 366
<212> TYPE: DNA
<213> ORGANISM: Artificial Sequence
<220> FEATURE:
<223> OTHER INFORMATION: CC-type lectin domain 3

<400> SEQUENCE: 14

```
cacggcggct tttgctacaa gatcgacacc gtgctgcgga gcttcgatca ggccagcagc     60

ggctactatt gccctcctgc tctggtcacc atcaccaaca gattcgagca ggccttcatc    120

accagcctga tcagcagcgt cgtgaagatg aaggacagct acttctggat cgccctgcag    180

gaccagaacg acaccggcga gtacacatgg aagcccgtgg gacagaaacc cgagcctgtg    240

cagtacaccc actggaacac acaccagcct agatactccg gcggctgcgt ggcaatgaga    300

ggcagacatc ctctcggcag atgggaagtg aagcactgtc ggcacttcaa ggccatgtct    360

ctgtgc                                                                366
```

<210> SEQ ID NO 15
<211> LENGTH: 1818
<212> TYPE: DNA
<213> ORGANISM: Artificial Sequence
<220> FEATURE:
<223> OTHER INFORMATION: Extracellular domains of PLA2R Construct
      4028.CF123

<400> SEQUENCE: 15

```
aagggcatct tcgtgatcca gagcgagagc ctgaagaagt gcatccaggc cggcaagagc     60

gtgctgaccc tggaaaattg caagcaggcc aacaagcaca tgctgtggaa atgggtgtcc    120

aaccacggcc tgttcaacat cggcggctct ggatgtctgg gcctgaattt ctctgcccct    180

gagcagcctc tgagcctgta cgagtgtgat agcaccctgg tgtccctgag atggcggtgc    240
```

aaccggaaga tgatcacagg ccctctgcag tactctgtgc aggtcgccca cgacaatacc 300
gtggtggcca gcagaaagta catccacaag tggatcagct acggcagcgg cggaggcgac 360
atctgtgaat acctgcacaa ggatctgcac accatcaagg gcaacaccca cggaatgccc 420
tgcatgttcc cgtttcagta caaccaccag tggcaccacg agtgcaccag agaaggcaga 480
gaggacgacc tgctttggtg cgccacaacc agcagatacg agcgggatga gaagtggggc 540
ttctgccctg atcctacctc tgccgaagtg ggctgcgata ccatctggga gaaagacctg 600
aacagccaca tctgctacca gttcaacctg ctgtccagcc tgtcttggag cgaggcccac 660
agcagctgtc aaatgcaagg cggcacactg ctgagcatca ccgacgagac agaggaaaac 720
ttcatccgcg agcacatgag cagcaagacc gtggaagtgt ggatgggact gaaccagctg 780
gatgagcatg ccggatggca gtggagtgat ggcacccctc tgaactacct gaactggtcc 840
cctgaagtga acttcgagcc cttcgtggaa gatcactgcg gcaccttcag cagcttcatg 900
cccagcgctt ggagaagcag agactgcgag agcaccctgc cttacatctg caagaagtac 960
ctgaaccaca tcgaccacga gatcgtggaa aaggacgcct ggaagtacta cgccacacac 1020
tgcgagcctg gctggaaccc ctacaaccgg aactgctaca agctgcagaa agaggaaaag 1080
acctggcacg aggccctgag aagctgccag gccgataata gcgccctgat cgacatcaca 1140
agcctggccg aggtggaatt tctggtcact ctgctgggcg acgagaacgc ctctgagaca 1200
tggatcggcc tgtccagcaa caagatcccc gtgtccttcg agtggtccaa cgacagcagc 1260
gtgatcttca ccaactggca caccctggaa cctcacatct tccccaacag atcccagctg 1320
tgtgtgtccg ccgagcagtc tgaaggccac tggaaagtga agaactgcga ggaacggctg 1380
ttctacatct gtaaaaaggc cggccacgtg ctgtccgatg ccgagagtgg atgtcaagaa 1440
ggctgggaga gacacggcgg cttttgctac aagatcgaca ccgtgctgcg gagcttcgat 1500
caggccagca gcggctacta ttgccctcct gctctggtca ccatcaccaa cagattcgag 1560
caggccttca tcaccagcct gatcagcagc gtcgtgaaga tgaaggacag ctacttctgg 1620
atcgccctgc aggaccagaa cgacaccggc gagtacacat ggaagcccgt gggacagaaa 1680
cccgagcctg tgcagtacac ccactggaac acacaccagc ctagatactc cggcggctgc 1740
gtggcaatga gaggcagaca tcctctcggc agatgggaag tgaagcactg tcggcacttc 1800
aaggccatgt ctctgtgc 1818

<210> SEQ ID NO 16
<211> LENGTH: 75
<212> TYPE: DNA
<213> ORGANISM: Artificial Sequence
<220> FEATURE:
<223> OTHER INFORMATION: Linker

<400> SEQUENCE: 16
aagcagcccg tggaaaatca agagaaggcc gagtacgagg aacgctggcc ttttcaccct 60
tgctacctgt ccgga 75

<210> SEQ ID NO 17
<211> LENGTH: 2682
<212> TYPE: DNA
<213> ORGANISM: Artificial Sequence
<220> FEATURE:
<223> OTHER INFORMATION: PLA2R-CAAR Construct 4028.CF123

<400> SEQUENCE: 17

```
atgctgctga gccctagcct gctgctgctc ctgcttcttg gagcccctag aggatgtgcc     60
ggatctgaag gtgttgccgc cgctctgaca cccgagagac tgctggaatg gcaggacaag    120
ggcatcttcg tgatccagag cgagagcctg aagaagtgca tccaggccgg caagagcgtg    180
ctgaccctgg aaaattgcaa gcaggccaac aagcacatgc tgtggaaatg ggtgtccaac    240
cacggcctgt tcaacatcgg cggctctgga tgtctgggcc tgaatttctc tgcccctgag    300
cagcctctga gcctgtacga gtgtgatagc accctggtgt ccctgagatg gcggtgcaac    360
cggaagatga tcacaggccc tctgcagtac tctgtgcagg tcgcccacga caataccgtg    420
gtggccagca gaaagtacat ccacaagtgg atcagctacg gcagcggcgg aggcgacatc    480
tgtgaatacc tgcacaagga tctgcacacc atcaagggca acacccacgg aatgccctgc    540
atgttcccgt ttcagtacaa ccaccagtgg caccacgagt gcaccagaga aggcagagag    600
gacgacctgc tttggtgcgc cacaaccagc agatacgagc gggatgagaa gtggggcttc    660
tgccctgatc ctacctctgc cgaagtgggc tgcgatacca tctgggagaa agacctgaac    720
agccacatct gctaccagtt caacctgctg tccagcctgt cttggagcga ggcccacagc    780
agctgtcaaa tgcaaggcgg cacactgctg agcatcaccg acgagacaga ggaaaacttc    840
atccgcgagc acatgagcag caagaccgtg gaagtgtgga tgggactgaa ccagctggat    900
gagcatgccg gatggcagtg gagtgatggc acccctctga actacctgaa ctggtcccct    960
gaagtgaact tcgagccctt cgtggaagat cactgcggca ccttcagcag cttcatgccc   1020
agcgcttgga gaagcagaga ctgcgagagc accctgcctt acatctgcaa gaagtacctg   1080
aaccacatcg accacgagat cgtggaaaag gacgcctgga agtactacgc cacacactgc   1140
gagcctggct ggaaccccta caaccggaac tgctacaagc tgcagaaaga ggaaaagacc   1200
tggcacgagg ccctgagaag ctgccaggcc gataatagcg ccctgatcga catcacaagc   1260
ctggccgagg tggaatttct ggtcactctg ctgggcgacg agaacgcctc tgagacatgg   1320
atcggcctgt ccagcaacaa gatccccgtg tccttcgagt ggtccaacga cagcagcgtg   1380
atcttcacca actggcacac cctggaacct cacatcttcc ccaacagatc ccagctgtgt   1440
gtgtccgccg agcagtctga aggccactgg aaagtgaaga actgcgagga acggctgttc   1500
tacatctgta aaaaggccgg ccacgtgctg tccgatgccg agagtggatg tcaagaaggc   1560
tgggagagac acggcggctt ttgctacaag atcgacaccg tgctgcggag cttcgatcag   1620
gccagcagcg gctactattg ccctcctgct ctggtcacca tcaccaacag attcgagcag   1680
gccttcatca ccagcctgat cagcagcgtc gtgaagatga aggacagcta cttctggatc   1740
gccctgcagg accagaacga caccggcgag tacacatgga agcccgtggg acagaaaccc   1800
gagcctgtgc agtacaccca ctggaacaca caccagccta gatactccgg cggctgcgtg   1860
gcaatgagag gcagacatcc tctcggcaga tgggaagtga agcactgtcg gcacttcaag   1920
gccatgtctc tgtgcaagca gcccgtggaa aatcaagaga aggccgagta cgaggaacgc   1980
tggccttttc acccttgcta cctgtccgga accacgacgc cagcgccgcg accaccaaca   2040
ccggcgccca ccatcgcgtc gcagcccctg tccctgcgcc cagaggcgtg ccggccagcg   2100
gcggggggcg cagtgcacac gagggggctg gacttcgcct gtgatatcta catctgggcg   2160
cccttggccg ggacttgtgg ggtccttctc ctgtcactgg ttatcaccct ttactgcaaa   2220
cggggcagaa agaaactcct gtatatattc aaacaaccat ttatgagacc agtacaaact   2280
actcaagagg aagatggctg tagctgccga tttccagaag aagaagaagg aggatgtgaa   2340
ctgagagtga agttcagcag gagcgcagac gcccccgcgt acaagcaggg ccagaaccag   2400
```

```
ctctataacg agctcaatct aggacgaaga gaggagtacg atgttttgga caagagacgt   2460

ggccgggacc ctgagatggg gggaaagccg agaaggaaga accctcagga aggcctgtac   2520

aatgaactgc agaaagataa gatggcggag gcctacagtg agattgggat gaaaggcgag   2580

cgccggaggg gcaaggggca cgatggcctt taccagggtc tcagtacagc caccaaggac   2640

acctacgacg cccttcacat gcaggccctg ccccctcgct aa                      2682


<210> SEQ ID NO 18
<211> LENGTH: 893
<212> TYPE: PRT
<213> ORGANISM: Artificial Sequence
<220> FEATURE:
<223> OTHER INFORMATION: PLA2R-CAAR Construct 4028.CF123

<400> SEQUENCE: 18

Met Leu Leu Ser Pro Ser Leu Leu Leu Leu Leu Leu Leu Gly Ala Pro
1               5                   10                  15

Arg Gly Cys Ala Gly Ser Glu Gly Val Ala Ala Ala Leu Thr Pro Glu
            20                  25                  30

Arg Leu Leu Glu Trp Gln Asp Lys Gly Ile Phe Val Ile Gln Ser Glu
        35                  40                  45

Ser Leu Lys Lys Cys Ile Gln Ala Gly Lys Ser Val Leu Thr Leu Glu
    50                  55                  60

Asn Cys Lys Gln Ala Asn Lys His Met Leu Trp Lys Trp Val Ser Asn
65                  70                  75                  80

His Gly Leu Phe Asn Ile Gly Gly Ser Gly Cys Leu Gly Leu Asn Phe
                85                  90                  95

Ser Ala Pro Glu Gln Pro Leu Ser Leu Tyr Glu Cys Asp Ser Thr Leu
            100                 105                 110

Val Ser Leu Arg Trp Arg Cys Asn Arg Lys Met Ile Thr Gly Pro Leu
        115                 120                 125

Gln Tyr Ser Val Gln Val Ala His Asp Asn Thr Val Val Ala Ser Arg
    130                 135                 140

Lys Tyr Ile His Lys Trp Ile Ser Tyr Gly Ser Gly Gly Gly Asp Ile
145                 150                 155                 160

Cys Glu Tyr Leu His Lys Asp Leu His Thr Ile Lys Gly Asn Thr His
                165                 170                 175

Gly Met Pro Cys Met Phe Pro Phe Gln Tyr Asn His Gln Trp His His
            180                 185                 190

Glu Cys Thr Arg Glu Gly Arg Glu Asp Asp Leu Leu Trp Cys Ala Thr
        195                 200                 205

Thr Ser Arg Tyr Glu Arg Asp Glu Lys Trp Gly Phe Cys Pro Asp Pro
    210                 215                 220

Thr Ser Ala Glu Val Gly Cys Asp Thr Ile Trp Glu Lys Asp Leu Asn
225                 230                 235                 240

Ser His Ile Cys Tyr Gln Phe Asn Leu Leu Ser Ser Leu Ser Trp Ser
                245                 250                 255

Glu Ala His Ser Ser Cys Gln Met Gln Gly Gly Thr Leu Leu Ser Ile
            260                 265                 270

Thr Asp Glu Thr Glu Glu Asn Phe Ile Arg Glu His Met Ser Ser Lys
        275                 280                 285

Thr Val Glu Val Trp Met Gly Leu Asn Gln Leu Asp Glu His Ala Gly
    290                 295                 300

Trp Gln Trp Ser Asp Gly Thr Pro Leu Asn Tyr Leu Asn Trp Ser Pro
```

-continued

```
305                 310                 315                 320

Glu Val Asn Phe Glu Pro Phe Val Glu Asp His Cys Gly Thr Phe Ser
                325                 330                 335

Ser Phe Met Pro Ser Ala Trp Arg Ser Arg Asp Cys Glu Ser Thr Leu
            340                 345                 350

Pro Tyr Ile Cys Lys Lys Tyr Leu Asn His Ile Asp His Glu Ile Val
        355                 360                 365

Glu Lys Asp Ala Trp Lys Tyr Tyr Ala Thr His Cys Glu Pro Gly Trp
    370                 375                 380

Asn Pro Tyr Asn Arg Asn Cys Tyr Lys Leu Gln Lys Glu Glu Lys Thr
385                 390                 395                 400

Trp His Glu Ala Leu Arg Ser Cys Gln Ala Asp Asn Ser Ala Leu Ile
                405                 410                 415

Asp Ile Thr Ser Leu Ala Glu Val Glu Phe Leu Val Thr Leu Leu Gly
            420                 425                 430

Asp Glu Asn Ala Ser Glu Thr Trp Ile Gly Leu Ser Ser Asn Lys Ile
        435                 440                 445

Pro Val Ser Phe Glu Trp Ser Asn Asp Ser Ser Val Ile Phe Thr Asn
    450                 455                 460

Trp His Thr Leu Glu Pro His Ile Phe Pro Asn Arg Ser Gln Leu Cys
465                 470                 475                 480

Val Ser Ala Glu Gln Ser Glu Gly His Trp Lys Val Lys Asn Cys Glu
                485                 490                 495

Glu Arg Leu Phe Tyr Ile Cys Lys Lys Ala Gly His Val Leu Ser Asp
            500                 505                 510

Ala Glu Ser Gly Cys Gln Glu Gly Trp Glu Arg His Gly Gly Phe Cys
        515                 520                 525

Tyr Lys Ile Asp Thr Val Leu Arg Ser Phe Asp Gln Ala Ser Ser Gly
    530                 535                 540

Tyr Tyr Cys Pro Pro Ala Leu Val Thr Ile Thr Asn Arg Phe Glu Gln
545                 550                 555                 560

Ala Phe Ile Thr Ser Leu Ile Ser Ser Val Val Lys Met Lys Asp Ser
                565                 570                 575

Tyr Phe Trp Ile Ala Leu Gln Asp Gln Asn Asp Thr Gly Glu Tyr Thr
            580                 585                 590

Trp Lys Pro Val Gly Gln Lys Pro Glu Pro Val Gln Tyr Thr His Trp
        595                 600                 605

Asn Thr His Gln Pro Arg Tyr Ser Gly Gly Cys Val Ala Met Arg Gly
    610                 615                 620

Arg His Pro Leu Gly Arg Trp Glu Val Lys His Cys Arg His Phe Lys
625                 630                 635                 640

Ala Met Ser Leu Cys Lys Gln Pro Val Glu Asn Gln Glu Lys Ala Glu
                645                 650                 655

Tyr Glu Glu Arg Trp Pro Phe His Pro Cys Tyr Leu Ser Gly Thr Thr
            660                 665                 670

Thr Pro Ala Pro Arg Pro Pro Thr Pro Ala Pro Thr Ile Ala Ser Gln
        675                 680                 685

Pro Leu Ser Leu Arg Pro Glu Ala Cys Arg Pro Ala Ala Gly Gly Ala
    690                 695                 700

Val His Thr Arg Gly Leu Asp Phe Ala Cys Asp Ile Tyr Ile Trp Ala
705                 710                 715                 720

Pro Leu Ala Gly Thr Cys Gly Val Leu Leu Leu Ser Leu Val Ile Thr
                725                 730                 735
```

```
Leu Tyr Cys Lys Arg Gly Arg Lys Lys Leu Leu Tyr Ile Phe Lys Gln
            740                 745                 750

Pro Phe Met Arg Pro Val Gln Thr Thr Gln Glu Glu Asp Gly Cys Ser
        755                 760                 765

Cys Arg Phe Pro Glu Glu Glu Glu Gly Gly Cys Glu Leu Arg Val Lys
    770                 775                 780

Phe Ser Arg Ser Ala Asp Ala Pro Ala Tyr Lys Gln Gly Gln Asn Gln
785                 790                 795                 800

Leu Tyr Asn Glu Leu Asn Leu Gly Arg Arg Glu Glu Tyr Asp Val Leu
                805                 810                 815

Asp Lys Arg Arg Gly Arg Asp Pro Glu Met Gly Gly Lys Pro Arg Arg
            820                 825                 830

Lys Asn Pro Gln Glu Gly Leu Tyr Asn Glu Leu Gln Lys Asp Lys Met
        835                 840                 845

Ala Glu Ala Tyr Ser Glu Ile Gly Met Lys Gly Glu Arg Arg Arg Gly
    850                 855                 860

Lys Gly His Asp Gly Leu Tyr Gln Gly Leu Ser Thr Ala Thr Lys Asp
865                 870                 875                 880

Thr Tyr Asp Ala Leu His Met Gln Ala Leu Pro Pro Arg
                885                 890


<210> SEQ ID NO 19
<211> LENGTH: 24
<212> TYPE: PRT
<213> ORGANISM: Artificial Sequence
<220> FEATURE:
<223> OTHER INFORMATION: CD8 alpha transmembrane domain

<400> SEQUENCE: 19

Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 20
<211> LENGTH: 72
<212> TYPE: DNA
<213> ORGANISM: Artificial Sequence
<220> FEATURE:
<223> OTHER INFORMATION: CD8 alpha transmembrane domain

<400> SEQUENCE: 20

atctacatct gggcgccctt ggccgggact tgtggggtcc ttctcctgtc actggttatc      60

accctttact gc                                                          72


<210> SEQ ID NO 21
<211> LENGTH: 42
<212> TYPE: PRT
<213> ORGANISM: Artificial Sequence
<220> FEATURE:
<223> OTHER INFORMATION: 4-1BB

<400> SEQUENCE: 21

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 22
<211> LENGTH: 126
<212> TYPE: DNA
<213> ORGANISM: Artificial Sequence
<220> FEATURE:
<223> OTHER INFORMATION: 4-1BB

<400> SEQUENCE: 22
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 23
<211> LENGTH: 112
<212> TYPE: PRT
<213> ORGANISM: Artificial Sequence
<220> FEATURE:
<223> OTHER INFORMATION: CD3 zeta signaling domain

<400> SEQUENCE: 23

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 24
<211> LENGTH: 336
<212> TYPE: DNA
<213> ORGANISM: Artificial Sequence
<220> FEATURE:
<223> OTHER INFORMATION: CD3 zeta signaling domain

<400> SEQUENCE: 24
agagtgaagt tcagcaggag cgcagacgcc cccgcgtacc agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgc 336

<210> SEQ ID NO 25
<211> LENGTH: 1167
<212> TYPE: DNA
<213> ORGANISM: Artificial Sequence
<220> FEATURE:
<223> OTHER INFORMATION: PLA2R-CAAR Construct C

<400> SEQUENCE: 25

```
atggagtttg ggctgagctg gctttttctt gtggctattt taaaaggtgt ccagtgcgga     60

tccaaaggaa tatttgtcat tcagtcagag tctttgaaaa agtgcataca ggctggaaaa    120

agcgtgctta ccctggagaa ctgcaagcaa gctaataagc atatgctttg gaaatgggtt    180

agcaaccacg gactctttaa tatcggaggc tccggctgtc tgggcctgaa cttcagtgca    240

ccggagcaac cgctttctct gtacgaatgt gatagcacac ttgttagtct tcggtggcgg    300

tgtaaccgaa aaatgattac aggccctctg caatatagtg ttcaagtggc ccacgacaat    360

acagttgtgg cgtctagaaa atatattcac aagtggattt cctacgggag cggcggaggg    420

gatatatgtg aatatcttca caaagacttg catacaatcg ctagcttcgt gccggtcttc    480

ctgccagcga agccaaccac gacgccagca ccgcgaccac caacacctgc gcccaccatc    540

gcgtcgcagc ccctgtccct gcgcccagag gcgtgcagac cagcagcggg gggcgcagtg    600

cacacgaggg ggctggactt cgcctgtgat atctacatct gggcgccctt ggccgggact    660

tgtggggtcc ttctcctgtc actggttatc accctttact gcaagcgcgg tcgcaagaaa    720

ctgctctata tttttaaaca gccattcatg agacctgtcc agaccactca agaggaggac    780

ggatgttcct gtagatttcc tgaagaggaa gaggggggct gcgagctgag agtgaagttc    840

agcaggagcg cagacgcccc cgcgtaccag cagggccaga accagctcta taacgagctc    900

aatctaggac gaagagagga gtacgatgtt ttggacaaga gacgtggccg ggaccctgag    960

atggggggaa agccgagaag gaagaaccct caggaaggcc tgtacaatga actgcagaaa   1020

gataagatgg cggaggccta cagtgagatt gggatgaaag gcgagcgccg gaggggcaag   1080

gggcacgatg gcctttacca gggtctcagt acagccacca aggacaccta cgacgccctt   1140

cacatgcagg ccctgccccc tcgctaa                                       1167
```

<210> SEQ ID NO 26
<211> LENGTH: 388
<212> TYPE: PRT
<213> ORGANISM: Artificial Sequence
<220> FEATURE:
<223> OTHER INFORMATION: PLA2R-CAAR Construct C

<400> SEQUENCE: 26

```
Met Glu Phe Gly Leu Ser Trp Leu Phe Leu Val Ala Ile Leu Lys Gly
1               5                   10                  15

Val Gln Cys Gly Ser Lys Gly Ile Phe Val Ile Gln Ser Glu Ser Leu
            20                  25                  30

Lys Lys Cys Ile Gln Ala Gly Lys Ser Val Leu Thr Leu Glu Asn Cys
        35                  40                  45

Lys Gln Ala Asn Lys His Met Leu Trp Lys Trp Val Ser Asn His Gly
    50                  55                  60

Leu Phe Asn Ile Gly Gly Ser Gly Cys Leu Gly Leu Asn Phe Ser Ala
65                  70                  75                  80

Pro Glu Gln Pro Leu Ser Leu Tyr Glu Cys Asp Ser Thr Leu Val Ser
                85                  90                  95

Leu Arg Trp Arg Cys Asn Arg Lys Met Ile Thr Gly Pro Leu Gln Tyr
            100                 105                 110

Ser Val Gln Val Ala His Asp Asn Thr Val Val Ala Ser Arg Lys Tyr
        115                 120                 125

Ile His Lys Trp Ile Ser Tyr Gly Ser Gly Gly Gly Asp Ile Cys Glu
    130                 135                 140

Tyr Leu His Lys Asp Leu His Thr Ile Ala Ser Phe Val Pro Val Phe
```

-continued

```
145                 150                 155                 160

Leu Pro Ala Lys Pro Thr Thr Thr Pro Ala Pro Arg Pro Pro Thr Pro
                165                 170                 175

Ala Pro Thr Ile Ala Ser Gln Pro Leu Ser Leu Arg Pro Glu Ala Cys
            180                 185                 190

Arg Pro Ala Ala Gly Gly Ala Val His Thr Arg Gly Leu Asp Phe Ala
        195                 200                 205

Cys Asp Ile Tyr Ile Trp Ala Pro Leu Ala Gly Thr Cys Gly Val Leu
    210                 215                 220

Leu Leu Ser Leu Val Ile Thr Leu Tyr Cys Lys Arg Gly Arg Lys Lys
225                 230                 235                 240

Leu Leu Tyr Ile Phe Lys Gln Pro Phe Met Arg Pro Val Gln Thr Thr
                245                 250                 255

Gln Glu Glu Asp Gly Cys Ser Cys Arg Phe Pro Glu Glu Glu Glu Gly
            260                 265                 270

Gly Cys Glu Leu Arg Val Lys Phe Ser Arg Ser Ala Asp Ala Pro Ala
        275                 280                 285

Tyr Gln Gln Gly Gln Asn Gln Leu Tyr Asn Glu Leu Asn Leu Gly Arg
    290                 295                 300

Arg Glu Glu Tyr Asp Val Leu Asp Lys Arg Arg Gly Arg Asp Pro Glu
305                 310                 315                 320

Met Gly Gly Lys Pro Arg Arg Lys Asn Pro Gln Glu Gly Leu Tyr Asn
                325                 330                 335

Glu Leu Gln Lys Asp Lys Met Ala Glu Ala Tyr Ser Glu Ile Gly Met
            340                 345                 350

Lys Gly Glu Arg Arg Arg Gly Lys Gly His Asp Gly Leu Tyr Gln Gly
        355                 360                 365

Leu Ser Thr Ala Thr Lys Asp Thr Tyr Asp Ala Leu His Met Gln Ala
    370                 375                 380

Leu Pro Pro Arg
385


<210> SEQ ID NO 27
<211> LENGTH: 1761
<212> TYPE: DNA
<213> ORGANISM: Artificial Sequence
<220> FEATURE:
<223> OTHER INFORMATION: PLA2R-CAAR construct CF1

<400> SEQUENCE: 27

atggagtttg ggctgagctg gctttttctt gtggctattt taaaaggtgt ccagtgcgga     60

tccaaaggga tctttgttat acaaagtgag agcttgaaaa aatgtataca ggctggcaaa    120

agtgtactga ctcttgaaaa ttgcaaacaa gccaacaaac acatgctgtg gaaatgggtg    180

tctaatcacg gtctcttcaa tattggggga agtggatgcc tcggcctgaa tttctccgct    240

cccgaacagc ccctctcact ttatgagtgt gattcaactc tggtgtcctt gaggtggcga    300

tgtaaccgca agatgataac cggccccctc cagtattccg tccaagtagc acacgacaat    360

accgtggtgg catctaggaa atacattcat aagtggatat cttatggcag tggtggcggt    420

gacatatgcg agtacctgca caaggacctc cacacaataa aggggaacac gcacgggatg    480

ccgtgtatgt tcccgttcca atataatcat caatggcacc atgagtgtac gagagagggg    540

cgagaagacg acctcctgtg gtgtgcgacc acctcaagat atgaacggga tgagaagtgg    600

ggcttttgcc ccgacccaac ctccgccgag gttggttgcg acactatttg ggaaaaagat    660
```

ttgaacagtc atatatgcta tcaatttaat ttgttgagtt cactctcctg gagcgaagcg 720
cacagctctt gtcagatgca aggtggtaca ttgcttagca ttactgatga aactgaggag 780
aatttcatta gggagcatat gtcctcaaag acagtagagg tgtggatggg tctgaaccag 840
ctcgacgaac acgccggttg gcagtggtca gatggaacgc ctctgaatta tctcaactgg 900
tcccctgagg tcaactttga accgtttgtg gaagatcatt gtggtacttt ttccagtttt 960
atgccaagcg cctggcgaag ccgagactgc gagtctacgt tgccctatat ctgcaagaag 1020
tatttgaatc acatagatca tgaaattgtt gaagctagct tcgtgccggt cttcctgcca 1080
gcgaagccaa ccacgacgcc agcaccgcga ccaccaacac ctgcgcccac catcgcgtcg 1140
cagcccctgt ccctgcgccc agaggcgtgc agaccagcag cggggggcgc agtgcacacg 1200
agggggctgg acttcgcctg tgatatctac atctgggcgc ccttggccgg gacttgtggg 1260
gtccttctcc tgtcactggt tatcaccctt tactgcaagc gcggtcgcaa gaaactgctc 1320
tatattttta aacagccatt catgagacct gtccagacca ctcaagagga ggacggatgt 1380
tcctgtagat ttcctgaaga ggaagagggg gggtgcgagc tgagagtgaa gttcagcagg 1440
agcgcagacg cccccgcgta ccagcagggc cagaaccagc tctataacga gctcaatcta 1500
ggacgaagag aggagtacga tgttttggac aagagacgtg gccgggaccc tgagatgggg 1560
ggaaagccga gaaggaagaa ccctcaggaa ggcctgtaca atgaactgca gaaagataag 1620
atggcggagg cctacagtga gattgggatg aaaggcgagc gccggagggg caaggggcac 1680
gatggccttt accagggtct cagtacagcc accaaggaca cctacgacgc ccttcacatg 1740
caggccctgc cccctcgcta a 1761

<210> SEQ ID NO 28
<211> LENGTH: 586
<212> TYPE: PRT
<213> ORGANISM: Artificial Sequence
<220> FEATURE:
<223> OTHER INFORMATION: PLA2R-CAAR construct CF1

<400> SEQUENCE: 28

Met Glu Phe Gly Leu Ser Trp Leu Phe Leu Val Ala Ile Leu Lys Gly
1 5 10 15

Val Gln Cys Gly Ser Lys Gly Ile Phe Val Ile Gln Ser Glu Ser Leu
20 25 30

Lys Lys Cys Ile Gln Ala Gly Lys Ser Val Leu Thr Leu Glu Asn Cys
35 40 45

Lys Gln Ala Asn Lys His Met Leu Trp Lys Trp Val Ser Asn His Gly
50 55 60

Leu Phe Asn Ile Gly Gly Ser Gly Cys Leu Gly Leu Asn Phe Ser Ala
65 70 75 80

Pro Glu Gln Pro Leu Ser Leu Tyr Glu Cys Asp Ser Thr Leu Val Ser
85 90 95

Leu Arg Trp Arg Cys Asn Arg Lys Met Ile Thr Gly Pro Leu Gln Tyr
100 105 110

Ser Val Gln Val Ala His Asp Asn Thr Val Val Ala Ser Arg Lys Tyr
115 120 125

Ile His Lys Trp Ile Ser Tyr Gly Ser Gly Gly Gly Asp Ile Cys Glu
130 135 140

Tyr Leu His Lys Asp Leu His Thr Ile Lys Gly Asn Thr His Gly Met
145 150 155 160

Pro Cys Met Phe Pro Phe Gln Tyr Asn His Gln Trp His His Glu Cys

```
                165                 170                 175

Thr Arg Glu Gly Arg Glu Asp Asp Leu Leu Trp Cys Ala Thr Thr Ser
            180                 185                 190

Arg Tyr Glu Arg Asp Glu Lys Trp Gly Phe Cys Pro Asp Pro Thr Ser
        195                 200                 205

Ala Glu Val Gly Cys Asp Thr Ile Trp Glu Lys Asp Leu Asn Ser His
    210                 215                 220

Ile Cys Tyr Gln Phe Asn Leu Leu Ser Ser Leu Ser Trp Ser Glu Ala
225                 230                 235                 240

His Ser Ser Cys Gln Met Gln Gly Gly Thr Leu Leu Ser Ile Thr Asp
                245                 250                 255

Glu Thr Glu Glu Asn Phe Ile Arg Glu His Met Ser Ser Lys Thr Val
            260                 265                 270

Glu Val Trp Met Gly Leu Asn Gln Leu Asp Glu His Ala Gly Trp Gln
        275                 280                 285

Trp Ser Asp Gly Thr Pro Leu Asn Tyr Leu Asn Trp Ser Pro Glu Val
    290                 295                 300

Asn Phe Glu Pro Phe Val Glu Asp His Cys Gly Thr Phe Ser Ser Phe
305                 310                 315                 320

Met Pro Ser Ala Trp Arg Ser Arg Asp Cys Glu Ser Thr Leu Pro Tyr
                325                 330                 335

Ile Cys Lys Lys Tyr Leu Asn His Ile Asp His Glu Ile Val Glu Ala
            340                 345                 350

Ser Phe Val Pro Val Phe Leu Pro Ala Lys Pro Thr Thr Thr Pro Ala
        355                 360                 365

Pro Arg Pro Pro Thr Pro Ala Pro Thr Ile Ala Ser Gln Pro Leu Ser
    370                 375                 380

Leu Arg Pro Glu Ala Cys Arg Pro Ala Ala Gly Gly Ala Val His Thr
385                 390                 395                 400

Arg Gly Leu Asp Phe Ala Cys Asp Ile Tyr Ile Trp Ala Pro Leu Ala
                405                 410                 415

Gly Thr Cys Gly Val Leu Leu Leu Ser Leu Val Ile Thr Leu Tyr Cys
            420                 425                 430

Lys Arg Gly Arg Lys Lys Leu Leu Tyr Ile Phe Lys Gln Pro Phe Met
        435                 440                 445

Arg Pro Val Gln Thr Thr Gln Glu Glu Asp Gly Cys Ser Cys Arg Phe
    450                 455                 460

Pro Glu Glu Glu Glu Gly Gly Cys Glu Leu Arg Val Lys Phe Ser Arg
465                 470                 475                 480

Ser Ala Asp Ala Pro Ala Tyr Gln Gln Gly Gln Asn Gln Leu Tyr Asn
                485                 490                 495

Glu Leu Asn Leu Gly Arg Arg Glu Glu Tyr Asp Val Leu Asp Lys Arg
            500                 505                 510

Arg Gly Arg Asp Pro Glu Met Gly Gly Lys Pro Arg Arg Lys Asn Pro
        515                 520                 525

Gln Glu Gly Leu Tyr Asn Glu Leu Gln Lys Asp Lys Met Ala Glu Ala
    530                 535                 540

Tyr Ser Glu Ile Gly Met Lys Gly Glu Arg Arg Arg Gly Lys Gly His
545                 550                 555                 560

Asp Gly Leu Tyr Gln Gly Leu Ser Thr Ala Thr Lys Asp Thr Tyr Asp
                565                 570                 575

Ala Leu His Met Gln Ala Leu Pro Pro Arg
            580                 585
```

<210> SEQ ID NO 29
<211> LENGTH: 2490
<212> TYPE: DNA
<213> ORGANISM: Artificial Sequence
<220> FEATURE:
<223> OTHER INFORMATION: PLA2R-CAAR Construct CF123

<400> SEQUENCE: 29
atggagtttg ggctgagctg gctttttctt gtggctattt taaaaggtgt ccagtgcgga 60
tccaaaggga ttttcgtgat acagtccgag agtctcaaaa agtgtatcca ggcaggcaaa 120
agtgttctca ctctggaaaa ctgcaaacaa gcgaacaagc acatgttgtg gaagtgggtt 180
agtaaccatg gactgttcaa catcggaggt agtggatgcc ttggtctcaa tttctctgct 240
ccggaacagc ctttgtcact gtacgaatgc gactccactc tcgttagtct tagatggcga 300
tgcaatcgca aaatgattac gggaccactt caatattcag ttcaagtggc acatgataac 360
accgtagtgg cctcacggaa atacatccat aaatggattt cttatggtag cgggggcggc 420
gatatatgtg aatacctcca taaggatctc cacaccatta agggtaatac tcacggtatg 480
ccgtgtatgt ttccttttca gtacaatcat cagtggcatc atgaatgcac gagggaagga 540
cgcgaggacg atttgctctg gtgcgcaacc acctcacgct acgagagaga cgaaaaatgg 600
ggcttttgcc cggaccccac tagtgctgag gtaggatgtg atacgatttg ggaaaaggat 660
ttgaattctc atatttgcta ccagtttaat cttctttcat ccctgtcctg gtctgaggct 720
cattctagtt gccagatgca aggtgggact ttgctttcaa ttactgacga gactgaggaa 780
aattttatcc gagagcatat gtcttctaaa accgtagagg tatggatggg cctgaaccaa 840
ttggacgaac acgcgggctg gcagtggagc gacgggacac ctctcaacta ccttaattgg 900
agccctgagg taaactttga accgtttgtc gaggatcact gcggaacttt cagcagcttc 960
atgcctagtg catggcggtc ccgagactgt gagagcaccc ttccatacat atgtaaaaaa 1020
tacctcaatc acatagacca cgagatcgta gagaaggatg catggaaata ttatgctacg 1080
cactgtgagc cgggatggaa tccttataac cgcaactgtt acaagctgca aaaagaagag 1140
aagacatggc atgaggcgct gcgctcatgt caagcggaca attctgcact tatagatata 1200
actagtttgg cggaggtaga atttttggtt acgcttctcg gcgatgagaa tgcgtccgag 1260
acgtggatag ggttgtcaag caataaaatt cctgtaagtt ttgaatggtc aaatgactct 1320
tctgtcatct tcaccaattg gcacacactc gaaccccata tcttcccaaa ccgaagccag 1380
ttgtgtgtca gcgctgagca atcagaagga cattggaaag ttaaaaactg tgaagaaaga 1440
ctgttctaca tctgtaagaa ggcaggacat gtgctttcag atgcggaaag cggctgtcaa 1500
gaaggttggg agcgccatgg aggtttctgt tataaaatcg acacagtttt gcgatctttc 1560
gatcaggctt caagcgggta ctattgtcct cctgcactgg ttacaatcac gaaccggttt 1620
gaacaggctt ttataacttc tttgatttcc agcgtggtta aaatgaagga ctcttatttc 1680
tggatagccc tgcaagacca aaatgatacc ggtgagtaca catggaaacc ggtaggtcaa 1740
aagccagagc cagtccagta cactcattgg aatacccacc agcctaggta ctccggcggg 1800
tgtgtggcga tgcggggtcg ccaccctctc ggacgctggg aggtgaagca ttgccgccac 1860
ttcaaggcga tgagcttgtg taaacagccc gtcgaaaatc aggaaaaggc agctagcggt 1920
ggcggaggtt ctggaggtgg aggttcctcc ggaatctaca tctgggcgcc cttggccggg 1980
acttgtgggg tccttctcct gtcactggtt atcacccttt actgcaagcg cggtcgcaag 2040

```
aaactgctct atatttttaa acagccattc atgagacctg tccagaccac tcaagaggag   2100

gacggatgtt cctgtagatt tcctgaagag gaagaggggg ggtgcgagct gagagtgaag   2160

ttcagcagga gcgcagacgc ccccgcgtac cagcagggcc agaaccagct ctataacgag   2220

ctcaatctag gacgaagaga ggagtacgat gttttggaca agagacgtgg ccgggaccct   2280

gagatggggg gaaagccgag aaggaagaac cctcaggaag gcctgtacaa tgaactgcag   2340

aaagataaga tggcggaggc ctacagtgag attgggatga aaggcgagcg ccggaggggc   2400

aaggggcacg atggccttta ccagggtctc agtacagcca ccaaggacac ctacgacgcc   2460

cttcacatgc aggccctgcc ccctcgctaa                                    2490


<210> SEQ ID NO 30
<211> LENGTH: 829
<212> TYPE: PRT
<213> ORGANISM: Artificial Sequence
<220> FEATURE:
<223> OTHER INFORMATION: PLA2R-CAAR Construct CF123

<400> SEQUENCE: 30

Met Glu Phe Gly Leu Ser Trp Leu Phe Leu Val Ala Ile Leu Lys Gly
1               5                   10                  15

Val Gln Cys Gly Ser Lys Gly Ile Phe Val Ile Gln Ser Glu Ser Leu
            20                  25                  30

Lys Lys Cys Ile Gln Ala Gly Lys Ser Val Leu Thr Leu Glu Asn Cys
        35                  40                  45

Lys Gln Ala Asn Lys His Met Leu Trp Lys Trp Val Ser Asn His Gly
    50                  55                  60

Leu Phe Asn Ile Gly Gly Ser Gly Cys Leu Gly Leu Asn Phe Ser Ala
65                  70                  75                  80

Pro Glu Gln Pro Leu Ser Leu Tyr Glu Cys Asp Ser Thr Leu Val Ser
                85                  90                  95

Leu Arg Trp Arg Cys Asn Arg Lys Met Ile Thr Gly Pro Leu Gln Tyr
            100                 105                 110

Ser Val Gln Val Ala His Asp Asn Thr Val Val Ala Ser Arg Lys Tyr
        115                 120                 125

Ile His Lys Trp Ile Ser Tyr Gly Ser Gly Gly Gly Asp Ile Cys Glu
    130                 135                 140

Tyr Leu His Lys Asp Leu His Thr Ile Lys Gly Asn Thr His Gly Met
145                 150                 155                 160

Pro Cys Met Phe Pro Phe Gln Tyr Asn His Gln Trp His His Glu Cys
                165                 170                 175

Thr Arg Glu Gly Arg Glu Asp Asp Leu Leu Trp Cys Ala Thr Thr Ser
            180                 185                 190

Arg Tyr Glu Arg Asp Glu Lys Trp Gly Phe Cys Pro Asp Pro Thr Ser
        195                 200                 205

Ala Glu Val Gly Cys Asp Thr Ile Trp Glu Lys Asp Leu Asn Ser His
    210                 215                 220

Ile Cys Tyr Gln Phe Asn Leu Leu Ser Ser Leu Ser Trp Ser Glu Ala
225                 230                 235                 240

His Ser Ser Cys Gln Met Gln Gly Gly Thr Leu Leu Ser Ile Thr Asp
                245                 250                 255

Glu Thr Glu Glu Asn Phe Ile Arg Glu His Met Ser Ser Lys Thr Val
            260                 265                 270

Glu Val Trp Met Gly Leu Asn Gln Leu Asp Glu His Ala Gly Trp Gln
        275                 280                 285
```

```
Trp Ser Asp Gly Thr Pro Leu Asn Tyr Leu Asn Trp Ser Pro Glu Val
    290                 295                 300

Asn Phe Glu Pro Phe Val Glu Asp His Cys Gly Thr Phe Ser Ser Phe
305                 310                 315                 320

Met Pro Ser Ala Trp Arg Ser Arg Asp Cys Glu Ser Thr Leu Pro Tyr
                325                 330                 335

Ile Cys Lys Lys Tyr Leu Asn His Ile Asp His Glu Ile Val Glu Lys
            340                 345                 350

Asp Ala Trp Lys Tyr Tyr Ala Thr His Cys Glu Pro Gly Trp Asn Pro
        355                 360                 365

Tyr Asn Arg Asn Cys Tyr Lys Leu Gln Lys Glu Glu Lys Thr Trp His
    370                 375                 380

Glu Ala Leu Arg Ser Cys Gln Ala Asp Asn Ser Ala Leu Ile Asp Ile
385                 390                 395                 400

Thr Ser Leu Ala Glu Val Glu Phe Leu Val Thr Leu Leu Gly Asp Glu
                405                 410                 415

Asn Ala Ser Glu Thr Trp Ile Gly Leu Ser Ser Asn Lys Ile Pro Val
            420                 425                 430

Ser Phe Glu Trp Ser Asn Asp Ser Ser Val Ile Phe Thr Asn Trp His
        435                 440                 445

Thr Leu Glu Pro His Ile Phe Pro Asn Arg Ser Gln Leu Cys Val Ser
    450                 455                 460

Ala Glu Gln Ser Glu Gly His Trp Lys Val Lys Asn Cys Glu Glu Arg
465                 470                 475                 480

Leu Phe Tyr Ile Cys Lys Lys Ala Gly His Val Leu Ser Asp Ala Glu
                485                 490                 495

Ser Gly Cys Gln Glu Gly Trp Glu Arg His Gly Gly Phe Cys Tyr Lys
            500                 505                 510

Ile Asp Thr Val Leu Arg Ser Phe Asp Gln Ala Ser Ser Gly Tyr Tyr
        515                 520                 525

Cys Pro Pro Ala Leu Val Thr Ile Thr Asn Arg Phe Glu Gln Ala Phe
    530                 535                 540

Ile Thr Ser Leu Ile Ser Ser Val Val Lys Met Lys Asp Ser Tyr Phe
545                 550                 555                 560

Trp Ile Ala Leu Gln Asp Gln Asn Asp Thr Gly Glu Tyr Thr Trp Lys
                565                 570                 575

Pro Val Gly Gln Lys Pro Glu Pro Val Gln Tyr Thr His Trp Asn Thr
            580                 585                 590

His Gln Pro Arg Tyr Ser Gly Gly Cys Val Ala Met Arg Gly Arg His
        595                 600                 605

Pro Leu Gly Arg Trp Glu Val Lys His Cys Arg His Phe Lys Ala Met
    610                 615                 620

Ser Leu Cys Lys Gln Pro Val Glu Asn Gln Glu Lys Ala Ala Ser Gly
625                 630                 635                 640

Gly Gly Gly Ser Gly Gly Gly Gly Ser Ser Gly Ile Tyr Ile Trp Ala
                645                 650                 655

Pro Leu Ala Gly Thr Cys Gly Val Leu Leu Leu Ser Leu Val Ile Thr
            660                 665                 670

Leu Tyr Cys Lys Arg Gly Arg Lys Lys Leu Leu Tyr Ile Phe Lys Gln
        675                 680                 685

Pro Phe Met Arg Pro Val Gln Thr Thr Gln Glu Glu Asp Gly Cys Ser
    690                 695                 700
```

```
Cys Arg Phe Pro Glu Glu Glu Glu Gly Gly Cys Glu Leu Arg Val Lys
705                 710                 715                 720

Phe Ser Arg Ser Ala Asp Ala Pro Ala Tyr Gln Gln Gly Gln Asn Gln
                725                 730                 735

Leu Tyr Asn Glu Leu Asn Leu Gly Arg Arg Glu Glu Tyr Asp Val Leu
            740                 745                 750

Asp Lys Arg Arg Gly Arg Asp Pro Glu Met Gly Gly Lys Pro Arg Arg
        755                 760                 765

Lys Asn Pro Gln Glu Gly Leu Tyr Asn Glu Leu Gln Lys Asp Lys Met
    770                 775                 780

Ala Glu Ala Tyr Ser Glu Ile Gly Met Lys Gly Glu Arg Arg Arg Gly
785                 790                 795                 800

Lys Gly His Asp Gly Leu Tyr Gln Gly Leu Ser Thr Ala Thr Lys Asp
                805                 810                 815

Thr Tyr Asp Ala Leu His Met Gln Ala Leu Pro Pro Arg
            820                 825


<210> SEQ ID NO 31
<211> LENGTH: 2910
<212> TYPE: DNA
<213> ORGANISM: Artificial Sequence
<220> FEATURE:
<223> OTHER INFORMATION: PLA2R-CAAR Construct CF1237

<400> SEQUENCE: 31

atggagtttg ggctgagctg gctttttctt gtggctattt taaaaggtgt ccagtgcgga     60

tccaaaggga ttttcgtgat acagtccgag agtctcaaaa agtgtatcca ggcaggcaaa    120

agtgttctca ctctggaaaa ctgcaaacaa gcgaacaagc acatgttgtg gaagtgggtt    180

agtaaccatg gactgttcaa catcggaggt agtggatgcc ttggtctcaa tttctctgct    240

ccggaacagc ctttgtcact gtacgaatgc gactccactc tcgttagtct tagatggcga    300

tgcaatcgca aaatgattac gggaccactt caatattcag ttcaagtggc acatgataac    360

accgtagtgg cctcacggaa atacatccat aaatggattt cttatggtag cgggggcggc    420

gatatatgtg aatacctcca taaggatctc cacaccatta agggtaatac tcacggtatg    480

ccgtgtatgt ttccttttca gtacaatcat cagtggcatc atgaatgcac gagggaagga    540

cgcgaggacg atttgctctg gtgcgcaacc acctcacgct acgagagaga cgaaaaatgg    600

ggcttttgcc cggaccccac tagtgctgag gtaggatgtg atacgatttg ggaaaaggat    660

ttgaattctc atatttgcta ccagtttaat cttctttcat ccctgtcctg gtctgaggct    720

cattctagtt gccagatgca aggtgggact ttgctttcaa ttactgacga gactgaggaa    780

aattttatcc gagagcatat gtcttctaaa accgtagagg tatggatggg cctgaaccaa    840

ttggacgaac acgcgggctg gcagtggagc gacgggacac ctctcaacta ccttaattgg    900

agccctgagg taaactttga accgtttgtc gaggatcact gcggaacttt cagcagcttc    960

atgcctagtg catggcggtc ccgagactgt gagagcaccc ttccatacat atgtaaaaaa   1020

tacctcaatc acatagacca cgagatcgta gagaaggatg catggaaata ttatgctacg   1080

cactgtgagc cgggatggaa tccttataac cgcaactgtt acaagctgca aaaagaagag   1140

aagacatggc atgaggcgct gcgctcatgt caagcggaca attctgcact tatagatata   1200

actagtttgg cggaggtaga atttttggtt acgcttctcg gcgatgagaa tgcgtccgag   1260

acgtggatag ggttgtcaag caataaaatt cctgtaagtt ttgaatggtc aaatgactct   1320

tctgtcatct tcaccaattg gcacacactc gaaccccata tcttcccaaa ccgaagccag   1380
```

-continued

```
ttgtgtgtca gcgctgagca atcagaagga cattggaaag ttaaaaactg tgaagaaaga   1440

ctgttctaca tctgtaagaa ggcaggacat gtgctttcag atgcggaaag cggctgtcaa   1500

gaaggttggg agcgccatgg aggtttctgt tataaaatcg acacagtttt gcgatctttc   1560

gatcaggctt caagcgggta ctattgtcct cctgcactgg ttacaatcac gaaccggttt   1620

gaacaggctt ttataacttc tttgatttcc agcgtggtta aaatgaagga ctcttatttc   1680

tggatagccc tgcaagacca aaatgatacc ggtgagtaca catggaaacc ggtaggtcaa   1740

aagccagagc cagtccagta cactcattgg aatacccacc agcctaggta ctccggcggg   1800

tgtgtggcga tgcggggtcg ccaccctctc ggacgctggg aggtgaagca ttgccgccac   1860

ttcaaggcga tgagcttgtg taaacagccc gtcgaaaatc aggaaaaggc agttaacaca   1920

tctgatatgt accctatgcc taacacactc gaatatggga ataggacgta caagattata   1980

aacgcgaaca tgacgtggta tgctgcaatc aagacgtgcc tcatgcacaa agctcagctt   2040

gtgtctatta ctgaccaata ccaccaatca tttttgacag tcgtgttgaa tcgattgggg   2100

tacgcccatt ggatcggtct cttcacgacg gacaatgggc tcaattttga ctggagtgac   2160

ggtactaaat catcctttac tttttggaag gatgaagaaa gttctctgtt gggcgattgc   2220

gtgtttgctg actcaaatgg ccgatggcat tccacagcct gtgaaagttt tctgcaggga   2280

gctatttgcc acgtgcctcc cgaaacgcgg cagtccgaac acccggaatt ggctagcggt   2340

ggcggaggtt ctggaggtgg aggttcctcc ggaatctaca tctgggcgcc cttggccggg   2400

acttgtgggg tccttctcct gtcactggtt atcacccttt actgcaagcg cggtcgcaag   2460

aaactgctct atatttttaa acagccattc atgagacctg tccagaccac tcaagaggag   2520

gacggatgtt cctgtagatt tcctgaagag gaagaggggg ggtgcgagct gagagtgaag   2580

ttcagcagga gcgcagacgc ccccgcgtac cagcagggcc agaaccagct ctataacgag   2640

ctcaatctag gacgaagaga ggagtacgat gttttggaca agagacgtgg ccgggaccct   2700

gagatggggg gaaagccgag aaggaagaac cctcaggaag gcctgtacaa tgaactgcag   2760

aaagataaga tggcggaggc ctacagtgag attgggatga aaggcgagcg ccggaggggc   2820

aaggggcacg atggccttta ccagggtctc agtacagcca ccaaggacac ctacgacgcc   2880

cttcacatgc aggccctgcc ccctcgctaa                                    2910
```

<210> SEQ ID NO 32
<211> LENGTH: 969
<212> TYPE: PRT
<213> ORGANISM: Artificial Sequence
<220> FEATURE:
<223> OTHER INFORMATION: PLA2R-CAAR Construct CF1237

<400> SEQUENCE: 32

```
Met Glu Phe Gly Leu Ser Trp Leu Phe Leu Val Ala Ile Leu Lys Gly
1               5                   10                  15

Val Gln Cys Gly Ser Lys Gly Ile Phe Val Ile Gln Ser Glu Ser Leu
            20                  25                  30

Lys Lys Cys Ile Gln Ala Gly Lys Ser Val Leu Thr Leu Glu Asn Cys
        35                  40                  45

Lys Gln Ala Asn Lys His Met Leu Trp Lys Trp Val Ser Asn His Gly
    50                  55                  60

Leu Phe Asn Ile Gly Gly Ser Gly Cys Leu Gly Leu Asn Phe Ser Ala
65                  70                  75                  80

Pro Glu Gln Pro Leu Ser Leu Tyr Glu Cys Asp Ser Thr Leu Val Ser
```

-continued

```
                85                  90                  95

Leu Arg Trp Arg Cys Asn Arg Lys Met Ile Thr Gly Pro Leu Gln Tyr
            100                 105                 110

Ser Val Gln Val Ala His Asp Asn Thr Val Val Ala Ser Arg Lys Tyr
        115                 120                 125

Ile His Lys Trp Ile Ser Tyr Gly Ser Gly Gly Gly Asp Ile Cys Glu
    130                 135                 140

Tyr Leu His Lys Asp Leu His Thr Ile Lys Gly Asn Thr His Gly Met
145                 150                 155                 160

Pro Cys Met Phe Pro Phe Gln Tyr Asn His Gln Trp His His Glu Cys
                165                 170                 175

Thr Arg Glu Gly Arg Glu Asp Asp Leu Leu Trp Cys Ala Thr Thr Ser
            180                 185                 190

Arg Tyr Glu Arg Asp Glu Lys Trp Gly Phe Cys Pro Asp Pro Thr Ser
        195                 200                 205

Ala Glu Val Gly Cys Asp Thr Ile Trp Glu Lys Asp Leu Asn Ser His
    210                 215                 220

Ile Cys Tyr Gln Phe Asn Leu Leu Ser Ser Leu Ser Trp Ser Glu Ala
225                 230                 235                 240

His Ser Ser Cys Gln Met Gln Gly Gly Thr Leu Leu Ser Ile Thr Asp
                245                 250                 255

Glu Thr Glu Glu Asn Phe Ile Arg Glu His Met Ser Ser Lys Thr Val
            260                 265                 270

Glu Val Trp Met Gly Leu Asn Gln Leu Asp Glu His Ala Gly Trp Gln
        275                 280                 285

Trp Ser Asp Gly Thr Pro Leu Asn Tyr Leu Asn Trp Ser Pro Glu Val
    290                 295                 300

Asn Phe Glu Pro Phe Val Glu Asp His Cys Gly Thr Phe Ser Ser Phe
305                 310                 315                 320

Met Pro Ser Ala Trp Arg Ser Arg Asp Cys Glu Ser Thr Leu Pro Tyr
                325                 330                 335

Ile Cys Lys Lys Tyr Leu Asn His Ile Asp His Glu Ile Val Glu Lys
            340                 345                 350

Asp Ala Trp Lys Tyr Tyr Ala Thr His Cys Glu Pro Gly Trp Asn Pro
        355                 360                 365

Tyr Asn Arg Asn Cys Tyr Lys Leu Gln Lys Glu Glu Lys Thr Trp His
    370                 375                 380

Glu Ala Leu Arg Ser Cys Gln Ala Asp Asn Ser Ala Leu Ile Asp Ile
385                 390                 395                 400

Thr Ser Leu Ala Glu Val Glu Phe Leu Val Thr Leu Leu Gly Asp Glu
                405                 410                 415

Asn Ala Ser Glu Thr Trp Ile Gly Leu Ser Ser Asn Lys Ile Pro Val
            420                 425                 430

Ser Phe Glu Trp Ser Asn Asp Ser Ser Val Ile Phe Thr Asn Trp His
        435                 440                 445

Thr Leu Glu Pro His Ile Phe Pro Asn Arg Ser Gln Leu Cys Val Ser
    450                 455                 460

Ala Glu Gln Ser Glu Gly His Trp Lys Val Lys Asn Cys Glu Glu Arg
465                 470                 475                 480

Leu Phe Tyr Ile Cys Lys Lys Ala Gly His Val Leu Ser Asp Ala Glu
                485                 490                 495

Ser Gly Cys Gln Glu Gly Trp Glu Arg His Gly Gly Phe Cys Tyr Lys
            500                 505                 510
```

```
Ile Asp Thr Val Leu Arg Ser Phe Asp Gln Ala Ser Ser Gly Tyr Tyr
        515                 520                 525

Cys Pro Pro Ala Leu Val Thr Ile Thr Asn Arg Phe Glu Gln Ala Phe
    530                 535                 540

Ile Thr Ser Leu Ile Ser Ser Val Val Lys Met Lys Asp Ser Tyr Phe
545                 550                 555                 560

Trp Ile Ala Leu Gln Asp Gln Asn Asp Thr Gly Glu Tyr Thr Trp Lys
                565                 570                 575

Pro Val Gly Gln Lys Pro Glu Pro Val Gln Tyr Thr His Trp Asn Thr
            580                 585                 590

His Gln Pro Arg Tyr Ser Gly Gly Cys Val Ala Met Arg Gly Arg His
        595                 600                 605

Pro Leu Gly Arg Trp Glu Val Lys His Cys Arg His Phe Lys Ala Met
    610                 615                 620

Ser Leu Cys Lys Gln Pro Val Glu Asn Gln Glu Lys Ala Val Asn Thr
625                 630                 635                 640

Ser Asp Met Tyr Pro Met Pro Asn Thr Leu Glu Tyr Gly Asn Arg Thr
                645                 650                 655

Tyr Lys Ile Ile Asn Ala Asn Met Thr Trp Tyr Ala Ala Ile Lys Thr
            660                 665                 670

Cys Leu Met His Lys Ala Gln Leu Val Ser Ile Thr Asp Gln Tyr His
        675                 680                 685

Gln Ser Phe Leu Thr Val Val Leu Asn Arg Leu Gly Tyr Ala His Trp
    690                 695                 700

Ile Gly Leu Phe Thr Thr Asp Asn Gly Leu Asn Phe Asp Trp Ser Asp
705                 710                 715                 720

Gly Thr Lys Ser Ser Phe Thr Phe Trp Lys Asp Glu Glu Ser Ser Leu
                725                 730                 735

Leu Gly Asp Cys Val Phe Ala Asp Ser Asn Gly Arg Trp His Ser Thr
            740                 745                 750

Ala Cys Glu Ser Phe Leu Gln Gly Ala Ile Cys His Val Pro Pro Glu
        755                 760                 765

Thr Arg Gln Ser Glu His Pro Glu Leu Ala Ser Gly Gly Gly Gly Ser
    770                 775                 780

Gly Gly Gly Gly Ser Ser Gly Ile Tyr Ile Trp Ala Pro Leu Ala Gly
785                 790                 795                 800

Thr Cys Gly Val Leu Leu Leu Ser Leu Val Ile Thr Leu Tyr Cys Lys
                805                 810                 815

Arg Gly Arg Lys Lys Leu Leu Tyr Ile Phe Lys Gln Pro Phe Met Arg
            820                 825                 830

Pro Val Gln Thr Thr Gln Glu Glu Asp Gly Cys Ser Cys Arg Phe Pro
        835                 840                 845

Glu Glu Glu Glu Gly Gly Cys Glu Leu Arg Val Lys Phe Ser Arg Ser
    850                 855                 860

Ala Asp Ala Pro Ala Tyr Gln Gln Gly Gln Asn Gln Leu Tyr Asn Glu
865                 870                 875                 880

Leu Asn Leu Gly Arg Arg Glu Glu Tyr Asp Val Leu Asp Lys Arg Arg
                885                 890                 895

Gly Arg Asp Pro Glu Met Gly Gly Lys Pro Arg Arg Lys Asn Pro Gln
            900                 905                 910

Glu Gly Leu Tyr Asn Glu Leu Gln Lys Asp Lys Met Ala Glu Ala Tyr
        915                 920                 925
```

```
Ser Glu Ile Gly Met Lys Gly Glu Arg Arg Arg Gly Lys Gly His Asp
    930                 935                 940

Gly Leu Tyr Gln Gly Leu Ser Thr Ala Thr Lys Asp Thr Tyr Asp Ala
945                 950                 955                 960

Leu His Met Gln Ala Leu Pro Pro Arg
                965


<210> SEQ ID NO 33
<211> LENGTH: 2052
<212> TYPE: DNA
<213> ORGANISM: Artificial Sequence
<220> FEATURE:
<223> OTHER INFORMATION: PLA2R-CAAR Construct CF17

<400> SEQUENCE: 33

atggagtttg ggctgagctg gctttttctt gtggctattt taaaaggtgt ccagtgcgga     60

tccaaaggca tcttcgtaat ccagtcagaa agtttgaaaa aatgtatcca agctggcaaa    120

tcagtactta cccttgagaa ctgcaagcaa gccaataaac atatgctgtg gaaatgggtc    180

tcaaaccacg gcctcttcaa tattggtggg tcaggttgct tggggttgaa tttctccgcc    240

ccagagcaac cactcagcct ttacgagtgt gattccacac ttgtctcttt gcgatggcgc    300

tgcaatagga aaatgatcac aggccccctt cagtactctg tgcaagttgc tcatgataac    360

acagtcgtgg cgagtcggaa atatattcac aaatggattt cttatgggag tggtggagga    420

gatatatgcg agtatttgca taaggacttg cacaccatca agggaaacac tcacggtatg    480

ccatgtatgt ttccgttcca atataatcat caatggcacc acgaatgtac ccgagaggga    540

cgcgaggacg atcttctttg gtgcgccaca acctctcgat atgaacgaga tgagaagtgg    600

gggttttgtc ctgacccaac cagtgcagaa gtagggtgcg ataccatctg ggagaaagac    660

ttgaactcac acatatgcta tcagtttaat ttgttgtctt ctttgtcatg gagcgaagct    720

cattcatcat gccagatgca gggcgggaca ctgctttcta tcaccgacga gactgaggaa    780

aattttatcc gcgagcacat gtcaagcaag acagttgagg tttggatggg gctcaatcaa    840

ctggacgaac acgcagggtg gcagtggtcc gatggcactc cgctcaacta ccttaactgg    900

agcccagagg tgaactttga gccgtttgtc gaagatcact gtggtacttt tagctccttc    960

atgccgtccg catggagaag tcgcgactgc gagtcaaccc tcccttacat ctgtaagaaa   1020

tacctcaacc acatagatca cgaaatcgta gaggtcaata cgtccgacat gtacccaatg   1080

ccaaatacgt tggaatatgg gaataggaca tacaagataa ttaacgcaaa tatgacgtgg   1140

tatgccgcaa tcaaaacgtg cctcatgcac aaggcacagc tcgtgtcaat tacggaccag   1200

taccaccaat catttctcac agtcgttctt aatcgattgg gttatgcaca ctggataggc   1260

ttgttcacga cggacaatgg tttgaacttt gactggtccg atggaactaa aagttctttc   1320

actttttgga aggatgagga gtcctccttg ctcggggact gcgtcttcgc agattcaaac   1380

gggcgctggc actcaacggc atgtgagtcc ttcctgcagg gagctatatg ccatgtgcca   1440

ccagaaacac gccagtctga gcaccctgag ttggctagcg gtggcggagg ttctggaggt   1500

ggaggttcct ccggaatcta catctgggcg cccttggccg ggacttgtgg ggtccttctc   1560

ctgtcactgg ttatcaccct ttactgcaag cgcggtcgca agaaactgct ctatattttt   1620

aaacagccat tcatgagacc tgtccagacc actcaagagg aggacggatg ttcctgtaga   1680

tttcctgaag aggaagaggg ggggtgcgag ctgagagtga agttcagcag gagcgcagac   1740

gcccccgcgt accagcaggg ccagaaccag ctctataacg agctcaatct aggacgaaga   1800
```

-continued

```
gaggagtacg atgttttgga caagagacgt ggccgggacc ctgagatggg gggaaagccg   1860

agaaggaaga accctcagga aggcctgtac aatgaactgc agaaagataa gatggcggag   1920

gcctacagtg agattgggat gaaaggcgag cgccggaggg gcaaggggca cgatggcctt   1980

taccagggtc tcagtacagc caccaaggac acctacgacg cccttcacat gcaggccctg   2040

ccccctcgct aa                                                       2052


<210> SEQ ID NO 34
<211> LENGTH: 683
<212> TYPE: PRT
<213> ORGANISM: Artificial Sequence
<220> FEATURE:
<223> OTHER INFORMATION: PLA2R-CAAR Construct CF17

<400> SEQUENCE: 34

Met Glu Phe Gly Leu Ser Trp Leu Phe Leu Val Ala Ile Leu Lys Gly
1               5                   10                  15

Val Gln Cys Gly Ser Lys Gly Ile Phe Val Ile Gln Ser Glu Ser Leu
            20                  25                  30

Lys Lys Cys Ile Gln Ala Gly Lys Ser Val Leu Thr Leu Glu Asn Cys
        35                  40                  45

Lys Gln Ala Asn Lys His Met Leu Trp Lys Trp Val Ser Asn His Gly
    50                  55                  60

Leu Phe Asn Ile Gly Gly Ser Gly Cys Leu Gly Leu Asn Phe Ser Ala
65                  70                  75                  80

Pro Glu Gln Pro Leu Ser Leu Tyr Glu Cys Asp Ser Thr Leu Val Ser
                85                  90                  95

Leu Arg Trp Arg Cys Asn Arg Lys Met Ile Thr Gly Pro Leu Gln Tyr
            100                 105                 110

Ser Val Gln Val Ala His Asp Asn Thr Val Val Ala Ser Arg Lys Tyr
        115                 120                 125

Ile His Lys Trp Ile Ser Tyr Gly Ser Gly Gly Gly Asp Ile Cys Glu
    130                 135                 140

Tyr Leu His Lys Asp Leu His Thr Ile Lys Gly Asn Thr His Gly Met
145                 150                 155                 160

Pro Cys Met Phe Pro Phe Gln Tyr Asn His Gln Trp His His Glu Cys
                165                 170                 175

Thr Arg Glu Gly Arg Glu Asp Asp Leu Leu Trp Cys Ala Thr Thr Ser
            180                 185                 190

Arg Tyr Glu Arg Asp Glu Lys Trp Gly Phe Cys Pro Asp Pro Thr Ser
        195                 200                 205

Ala Glu Val Gly Cys Asp Thr Ile Trp Glu Lys Asp Leu Asn Ser His
    210                 215                 220

Ile Cys Tyr Gln Phe Asn Leu Leu Ser Ser Leu Ser Trp Ser Glu Ala
225                 230                 235                 240

His Ser Ser Cys Gln Met Gln Gly Gly Thr Leu Leu Ser Ile Thr Asp
                245                 250                 255

Glu Thr Glu Glu Asn Phe Ile Arg Glu His Met Ser Ser Lys Thr Val
            260                 265                 270

Glu Val Trp Met Gly Leu Asn Gln Leu Asp Glu His Ala Gly Trp Gln
        275                 280                 285

Trp Ser Asp Gly Thr Pro Leu Asn Tyr Leu Asn Trp Ser Pro Glu Val
    290                 295                 300

Asn Phe Glu Pro Phe Val Glu Asp His Cys Gly Thr Phe Ser Ser Phe
305                 310                 315                 320
```

```
Met Pro Ser Ala Trp Arg Ser Arg Asp Cys Glu Ser Thr Leu Pro Tyr
                325                 330                 335

Ile Cys Lys Lys Tyr Leu Asn His Ile Asp His Glu Ile Val Glu Val
            340                 345                 350

Asn Thr Ser Asp Met Tyr Pro Met Pro Asn Thr Leu Glu Tyr Gly Asn
        355                 360                 365

Arg Thr Tyr Lys Ile Ile Asn Ala Asn Met Thr Trp Tyr Ala Ala Ile
    370                 375                 380

Lys Thr Cys Leu Met His Lys Ala Gln Leu Val Ser Ile Thr Asp Gln
385                 390                 395                 400

Tyr His Gln Ser Phe Leu Thr Val Val Leu Asn Arg Leu Gly Tyr Ala
                405                 410                 415

His Trp Ile Gly Leu Phe Thr Thr Asp Asn Gly Leu Asn Phe Asp Trp
            420                 425                 430

Ser Asp Gly Thr Lys Ser Ser Phe Thr Phe Trp Lys Asp Glu Glu Ser
        435                 440                 445

Ser Leu Leu Gly Asp Cys Val Phe Ala Asp Ser Asn Gly Arg Trp His
    450                 455                 460

Ser Thr Ala Cys Glu Ser Phe Leu Gln Gly Ala Ile Cys His Val Pro
465                 470                 475                 480

Pro Glu Thr Arg Gln Ser Glu His Pro Glu Leu Ala Ser Gly Gly Gly
                485                 490                 495

Gly Ser Gly Gly Gly Gly Ser Ser Gly Ile Tyr Ile Trp Ala Pro Leu
            500                 505                 510

Ala Gly Thr Cys Gly Val Leu Leu Leu Ser Leu Val Ile Thr Leu Tyr
        515                 520                 525

Cys Lys Arg Gly Arg Lys Lys Leu Leu Tyr Ile Phe Lys Gln Pro Phe
    530                 535                 540

Met Arg Pro Val Gln Thr Thr Gln Glu Glu Asp Gly Cys Ser Cys Arg
545                 550                 555                 560

Phe Pro Glu Glu Glu Glu Gly Gly Cys Glu Leu Arg Val Lys Phe Ser
                565                 570                 575

Arg Ser Ala Asp Ala Pro Ala Tyr Gln Gln Gly Gln Asn Gln Leu Tyr
            580                 585                 590

Asn Glu Leu Asn Leu Gly Arg Arg Glu Glu Tyr Asp Val Leu Asp Lys
        595                 600                 605

Arg Arg Gly Arg Asp Pro Glu Met Gly Gly Lys Pro Arg Arg Lys Asn
    610                 615                 620

Pro Gln Glu Gly Leu Tyr Asn Glu Leu Gln Lys Asp Lys Met Ala Glu
625                 630                 635                 640

Ala Tyr Ser Glu Ile Gly Met Lys Gly Glu Arg Arg Arg Gly Lys Gly
                645                 650                 655

His Asp Gly Leu Tyr Gln Gly Leu Ser Thr Ala Thr Lys Asp Thr Tyr
            660                 665                 670

Asp Ala Leu His Met Gln Ala Leu Pro Pro Arg
        675                 680
```

<210> SEQ ID NO 35
<211> LENGTH: 1893
<212> TYPE: DNA
<213> ORGANISM: Artificial Sequence
<220> FEATURE:
<223> OTHER INFORMATION: PLA2R-CAAR Construct C17

<400> SEQUENCE: 35

```
atggagtttg ggctgagctg gctttttctt gtggctattt taaaaggtgt ccagtgcgga     60
tccaaaggaa tcttcgtaat tcaatctgag agtctgaaaa aatgtattca ggccggtaag    120
agcgtactca cgcttgaaaa ttgcaaacag gccaacaaac acatgctttg gaaatgggtt    180
tcaaatcacg ggttgtttaa catagggga tcaggatgtc tgggccttaa cttttccgca    240
cctgaacaac ctcttagtct gtatgagtgt gactcaacgc tggtctcctt gcgctggaga    300
tgcaatcgga agatgataac cgggcccctc cagtattccg ttcaggtcgc ccacgataat    360
actgttgttg catcccgaaa atatattcat aagtggatct cctacgggag tggaggggc    420
gatatttgtg aatacctcca caaggatctg cacactatca cttctgcgga agtaggctgt    480
gacacaatct gggagaaaga tctgaattca cacatttgct atcagttcaa tcttctgagt    540
tctttgagct ggtccgaagc acattcatcc tgtcagatgc aaggtggaac actcttgtca    600
ataacagatg aaacggaaga gaactttatt agagaacata tgtcctcaaa gactgtggag    660
gtgtggatgg gacttaacca gctcgatgaa catgcaggat ggcagtggag tgacggaacg    720
ccactgaact acctgaattg gagcccagag gtgaatttcg agcctttcgt agaggaccat    780
tgcggtactt tttcatcttt tatgcccagc gcatggagat cccgagattg tgaaagcacg    840
ctgccctata tttgtaaaaa gtacctgaac cacatagatc atgagatagt tgaggtaaat    900
acaagtgata tgtaccccat gccgaacaca ctcgagtacg gaaatagaac ctacaagata    960
atcaacgcta acatgacctg gtacgcggcc attaagacct gcctcatgca caaggctcaa   1020
ctcgtcagta ttactgacca atatcaccag tcatttctca ccgtcgtgtt gaatcgcctc   1080
ggttacgccc actggatcgg tttgtttaca acggacaatg gactcaattt cgattggtca   1140
gacggaacca aatctagttt taccttctgg aaagacgagg aatcaagcct gcttggggac   1200
tgcgtatttg cggactctaa tggccgatgg catagtacag cgtgtgagag ctttttgcag   1260
ggggcgattt gtcatgttcc gccggaaacc cgccaaagcg agcatccaga attggctagc   1320
ggtggcggag gttctggagg tggaggttcc tccggaatct acatctgggc gcccttggcc   1380
gggacttgtg gggtccttct cctgtcactg gttatcaccc tttactgcaa gcgcggtcgc   1440
aagaaactgc tctatatttt taaacagcca ttcatgagac ctgtccagac cactcaagag   1500
gaggacggat gttcctgtag atttcctgaa gaggaagagg gggggtgcga gctgagagtg   1560
aagttcagca ggagcgcaga cgcccccgcg taccagcagg gccagaacca gctctataac   1620
gagctcaatc taggacgaag agaggagtac gatgttttgg acaagagacg tggccgggac   1680
cctgagatgg ggggaaagcc gagaaggaag aaccctcagg aaggcctgta caatgaactg   1740
cagaaagata agatggcgga ggcctacagt gagattggga tgaaaggcga gcgccggagg   1800
ggcaaggggc acgatggcct ttaccagggt ctcagtacag ccaccaagga cacctacgac   1860
gcccttcaca tgcaggccct gccccctcgc taa                                1893
```

<210> SEQ ID NO 36
<211> LENGTH: 630
<212> TYPE: PRT
<213> ORGANISM: Artificial Sequence
<220> FEATURE:
<223> OTHER INFORMATION: PLA2R-CAAR Construct C17

<400> SEQUENCE: 36

```
Met Glu Phe Gly Leu Ser Trp Leu Phe Leu Val Ala Ile Leu Lys Gly
1               5                   10                  15

Val Gln Cys Gly Ser Lys Gly Ile Phe Val Ile Gln Ser Glu Ser Leu
```

```
            20                  25                  30

Lys Lys Cys Ile Gln Ala Gly Lys Ser Val Leu Thr Leu Glu Asn Cys
        35                  40                  45

Lys Gln Ala Asn Lys His Met Leu Trp Lys Trp Val Ser Asn His Gly
    50                  55                  60

Leu Phe Asn Ile Gly Gly Ser Gly Cys Leu Gly Leu Asn Phe Ser Ala
65                  70                  75                  80

Pro Glu Gln Pro Leu Ser Leu Tyr Glu Cys Asp Ser Thr Leu Val Ser
                85                  90                  95

Leu Arg Trp Arg Cys Asn Arg Lys Met Ile Thr Gly Pro Leu Gln Tyr
            100                 105                 110

Ser Val Gln Val Ala His Asp Asn Thr Val Val Ala Ser Arg Lys Tyr
        115                 120                 125

Ile His Lys Trp Ile Ser Tyr Gly Ser Gly Gly Gly Asp Ile Cys Glu
    130                 135                 140

Tyr Leu His Lys Asp Leu His Thr Ile Thr Ser Ala Glu Val Gly Cys
145                 150                 155                 160

Asp Thr Ile Trp Glu Lys Asp Leu Asn Ser His Ile Cys Tyr Gln Phe
                165                 170                 175

Asn Leu Leu Ser Ser Leu Ser Trp Ser Glu Ala His Ser Ser Cys Gln
            180                 185                 190

Met Gln Gly Gly Thr Leu Leu Ser Ile Thr Asp Glu Thr Glu Glu Asn
        195                 200                 205

Phe Ile Arg Glu His Met Ser Ser Lys Thr Val Glu Val Trp Met Gly
    210                 215                 220

Leu Asn Gln Leu Asp Glu His Ala Gly Trp Gln Trp Ser Asp Gly Thr
225                 230                 235                 240

Pro Leu Asn Tyr Leu Asn Trp Ser Pro Glu Val Asn Phe Glu Pro Phe
                245                 250                 255

Val Glu Asp His Cys Gly Thr Phe Ser Ser Phe Met Pro Ser Ala Trp
            260                 265                 270

Arg Ser Arg Asp Cys Glu Ser Thr Leu Pro Tyr Ile Cys Lys Lys Tyr
        275                 280                 285

Leu Asn His Ile Asp His Glu Ile Val Glu Val Asn Thr Ser Asp Met
    290                 295                 300

Tyr Pro Met Pro Asn Thr Leu Glu Tyr Gly Asn Arg Thr Tyr Lys Ile
305                 310                 315                 320

Ile Asn Ala Asn Met Thr Trp Tyr Ala Ala Ile Lys Thr Cys Leu Met
                325                 330                 335

His Lys Ala Gln Leu Val Ser Ile Thr Asp Gln Tyr His Gln Ser Phe
            340                 345                 350

Leu Thr Val Val Leu Asn Arg Leu Gly Tyr Ala His Trp Ile Gly Leu
        355                 360                 365

Phe Thr Thr Asp Asn Gly Leu Asn Phe Asp Trp Ser Asp Gly Thr Lys
    370                 375                 380

Ser Ser Phe Thr Phe Trp Lys Asp Glu Glu Ser Ser Leu Leu Gly Asp
385                 390                 395                 400

Cys Val Phe Ala Asp Ser Asn Gly Arg Trp His Ser Thr Ala Cys Glu
                405                 410                 415

Ser Phe Leu Gln Gly Ala Ile Cys His Val Pro Pro Glu Thr Arg Gln
            420                 425                 430

Ser Glu His Pro Glu Leu Ala Ser Gly Gly Gly Gly Ser Gly Gly Gly
        435                 440                 445
```

```
Gly Ser Ser Gly Ile Tyr Ile Trp Ala Pro Leu Ala Gly Thr Cys Gly
    450                 455                 460

Val Leu Leu Leu Ser Leu Val Ile Thr Leu Tyr Cys Lys Arg Gly Arg
465                 470                 475                 480

Lys Lys Leu Leu Tyr Ile Phe Lys Gln Pro Phe Met Arg Pro Val Gln
                485                 490                 495

Thr Thr Gln Glu Glu Asp Gly Cys Ser Cys Arg Phe Pro Glu Glu Glu
            500                 505                 510

Glu Gly Gly Cys Glu Leu Arg Val Lys Phe Ser Arg Ser Ala Asp Ala
        515                 520                 525

Pro Ala Tyr Gln Gln Gly Gln Asn Gln Leu Tyr Asn Glu Leu Asn Leu
    530                 535                 540

Gly Arg Arg Glu Glu Tyr Asp Val Leu Asp Lys Arg Arg Gly Arg Asp
545                 550                 555                 560

Pro Glu Met Gly Gly Lys Pro Arg Arg Lys Asn Pro Gln Glu Gly Leu
                565                 570                 575

Tyr Asn Glu Leu Gln Lys Asp Lys Met Ala Glu Ala Tyr Ser Glu Ile
            580                 585                 590

Gly Met Lys Gly Glu Arg Arg Arg Gly Lys Gly His Asp Gly Leu Tyr
        595                 600                 605

Gln Gly Leu Ser Thr Ala Thr Lys Asp Thr Tyr Asp Ala Leu His Met
    610                 615                 620

Gln Ala Leu Pro Pro Arg
625                 630
```

<210> SEQ ID NO 37
<211> LENGTH: 1182
<212> TYPE: DNA
<213> ORGANISM: Artificial Sequence
<220> FEATURE:
<223> OTHER INFORMATION: PLA2R-CAAR Construct 4025.C

<400> SEQUENCE: 37

```
atgctgctga gccctagcct gctgctgctc ctgcttcttg gagcccctag aggatgtgcc      60

ggatctgaag gtgttgccgc cgctctgaca cccgagagac tgctggaatg gcaggacaag     120

ggcatcttcg tgatccagag cgagagcctg aagaagtgca tccaggccgg caagagcgtg     180

ctgaccctgg aaaattgcaa gcaggccaac aagcacatgc tgtggaaatg ggtgtccaac     240

cacggcctgt tcaacatcgg cggctctgga tgtctgggcc tgaatttctc tgcccctgag     300

cagcctctga gcctgtacga gtgtgatagc accctggtgt ccctgagatg gcggtgcaac     360

cggaagatga tcacaggccc tctgcagtac tctgtgcagg tcgcccacga caataccgtg     420

gtggccagca gaaagtacat ccacaagtgg atcagctacg gcagcggcgg aggcgacatc     480

tgtgaatacc tgcacaagga tctgtccgga accacgacgc cagcgccgcg accaccaaca     540

ccggcgccca ccatcgcgtc gcagcccctg tccctgcgcc cagaggcgtg ccggccagcg     600

gcggggggcg cagtgcacac gagggggctg gacttcgcct gtgatatcta catctgggcg     660

cccttggccg ggacttgtgg ggtccttctc ctgtcactgg ttatcaccct ttactgcaaa     720

cggggcagaa agaaactcct gtatatattc aaacaaccat ttatgagacc agtacaaact     780

actcaagagg aagatggctg tagctgccga tttccagaag aagaagaagg aggatgtgaa     840

ctgagagtga agttcagcag gagcgcagac gcccccgcgt acaagcaggg ccagaaccag     900

ctctataacg agctcaatct aggacgaaga gaggagtacg atgttttgga caagagacgt     960
```

```
ggccgggacc ctgagatggg gggaaagccg agaaggaaga accctcagga aggcctgtac   1020

aatgaactgc agaaagataa gatggcggag gcctacagtg agattgggat gaaaggcgag   1080

cgccggaggg gcaaggggca cgatggcctt taccagggtc tcagtacagc caccaaggac   1140

acctacgacg cccttcacat gcaggccctg ccccctcgct aa                       1182
```

<210> SEQ ID NO 38
<211> LENGTH: 393
<212> TYPE: PRT
<213> ORGANISM: Artificial Sequence
<220> FEATURE:
<223> OTHER INFORMATION: PLA2R-CAAR Construct 4025.C

<400> SEQUENCE: 38

```
Met Leu Leu Ser Pro Ser Leu Leu Leu Leu Leu Leu Leu Gly Ala Pro
1               5                   10                  15

Arg Gly Cys Ala Gly Ser Glu Gly Val Ala Ala Ala Leu Thr Pro Glu
            20                  25                  30

Arg Leu Leu Glu Trp Gln Asp Lys Gly Ile Phe Val Ile Gln Ser Glu
        35                  40                  45

Ser Leu Lys Lys Cys Ile Gln Ala Gly Lys Ser Val Leu Thr Leu Glu
    50                  55                  60

Asn Cys Lys Gln Ala Asn Lys His Met Leu Trp Lys Trp Val Ser Asn
65                  70                  75                  80

His Gly Leu Phe Asn Ile Gly Gly Ser Gly Cys Leu Gly Leu Asn Phe
                85                  90                  95

Ser Ala Pro Glu Gln Pro Leu Ser Leu Tyr Glu Cys Asp Ser Thr Leu
            100                 105                 110

Val Ser Leu Arg Trp Arg Cys Asn Arg Lys Met Ile Thr Gly Pro Leu
        115                 120                 125

Gln Tyr Ser Val Gln Val Ala His Asp Asn Thr Val Val Ala Ser Arg
    130                 135                 140

Lys Tyr Ile His Lys Trp Ile Ser Tyr Gly Ser Gly Gly Gly Asp Ile
145                 150                 155                 160

Cys Glu Tyr Leu His Lys Asp Leu Ser Gly Thr Thr Thr Pro Ala Pro
                165                 170                 175

Arg Pro Pro Thr Pro Ala Pro Thr Ile Ala Ser Gln Pro Leu Ser Leu
            180                 185                 190

Arg Pro Glu Ala Cys Arg Pro Ala Ala Gly Gly Ala Val His Thr Arg
        195                 200                 205

Gly Leu Asp Phe Ala Cys Asp Ile Tyr Ile Trp Ala Pro Leu Ala Gly
    210                 215                 220

Thr Cys Gly Val Leu Leu Leu Ser Leu Val Ile Thr Leu Tyr Cys Lys
225                 230                 235                 240

Arg Gly Arg Lys Lys Leu Leu Tyr Ile Phe Lys Gln Pro Phe Met Arg
                245                 250                 255

Pro Val Gln Thr Thr Gln Glu Glu Asp Gly Cys Ser Cys Arg Phe Pro
            260                 265                 270

Glu Glu Glu Glu Gly Gly Cys Glu Leu Arg Val Lys Phe Ser Arg Ser
        275                 280                 285

Ala Asp Ala Pro Ala Tyr Lys Gln Gly Gln Asn Gln Leu Tyr Asn Glu
    290                 295                 300

Leu Asn Leu Gly Arg Arg Glu Glu Tyr Asp Val Leu Asp Lys Arg Arg
305                 310                 315                 320

Gly Arg Asp Pro Glu Met Gly Gly Lys Pro Arg Arg Lys Asn Pro Gln
```

-continued

```
            325                 330                 335

Glu Gly Leu Tyr Asn Glu Leu Gln Lys Asp Lys Met Ala Glu Ala Tyr
            340                 345                 350

Ser Glu Ile Gly Met Lys Gly Glu Arg Arg Arg Gly Lys Gly His Asp
        355                 360                 365

Gly Leu Tyr Gln Gly Leu Ser Thr Ala Thr Lys Asp Thr Tyr Asp Ala
    370                 375                 380

Leu His Met Gln Ala Leu Pro Pro Arg
385                 390


<210> SEQ ID NO 39
<211> LENGTH: 1821
<212> TYPE: DNA
<213> ORGANISM: Artificial Sequence
<220> FEATURE:
<223> OTHER INFORMATION: PLA2R-CAAR Construct 4026.CF1

<400> SEQUENCE: 39

atgctgctga gccctagcct gctgctgctc ctgcttcttg gagcccctag aggatgtgcc     60

ggatctgaag gtgttgccgc cgctctgaca cccgagagac tgctggaatg gcaggacaag    120

ggcatcttcg tgatccagag cgagagcctg aagaagtgca tccaggccgg caagagcgtg    180

ctgaccctgg aaaattgcaa gcaggccaac aagcacatgc tgtggaaatg ggtgtccaac    240

cacggcctgt tcaacatcgg cggctctgga tgtctgggcc tgaatttctc tgcccctgag    300

cagcctctga gcctgtacga gtgtgatagc accctggtgt ccctgagatg gcggtgcaac    360

cggaagatga tcacaggccc tctgcagtac tctgtgcagg tcgcccacga caataccgtg    420

gtggccagca gaaagtacat ccacaagtgg atcagctacg gcagcggcgg aggcgacatc    480

tgtgaatacc tgcacaagga tctgcacacc atcaagggca acacccacgg aatgccctgc    540

atgttcccgt ttcagtacaa ccaccagtgg caccacgagt gcaccagaga aggcagagag    600

gacgacctgc tttggtgcgc cacaaccagc agatacgagc gggatgagaa gtggggcttc    660

tgccctgatc ctacctctgc cgaagtgggc tgcgatacca tctgggagaa agacctgaac    720

agccacatct gctaccagtt caacctgctg tccagcctgt cttggagcga ggcccacagc    780

agctgtcaaa tgcaaggcgg cacactgctg agcatcaccg acgagacaga ggaaaacttc    840

atccgcgagc acatgagcag caagaccgtg gaagtgtgga tgggactgaa ccagctggat    900

gagcatgccg gatggcagtg gagtgatggc acccctctga actacctgaa ctggtcccct    960

gaagtgaact tcgagccctt cgtggaagat cactgcggca ccttcagcag cttcatgccc   1020

agcgcttgga gaagcagaga ctgcgagagc accctgcctt acatctgcaa gaagtacctg   1080

aaccacatcg accacgagat cgtggaaaag gacgcctgga agtactacgc cacacactgc   1140

gagtccggaa ccacgacgcc agcgccgcga ccaccaacac cggcgcccac catcgcgtcg   1200

cagcccctgt ccctgcgccc agaggcgtgc cggccagcgg cggggggcgc agtgcacacg   1260

agggggctgg acttcgcctg tgatatctac atctgggcgc ccttggccgg gacttgtggg   1320

gtccttctcc tgtcactggt tatcaccctt tactgcaaac ggggcagaaa gaaactcctg   1380

tatatattca aacaaccatt tatgagacca gtacaaacta ctcaagagga agatggctgt   1440

agctgccgat ttccagaaga agaagaagga ggatgtgaac tgagagtgaa gttcagcagg   1500

agcgcagacg cccccgcgta caagcagggc cagaaccagc tctataacga gctcaatcta   1560

ggacgaagag aggagtacga tgttttggac aagagacgtg gccgggaccc tgagatgggg   1620

ggaaagccga gaaggaagaa ccctcaggaa ggcctgtaca atgaactgca gaaagataag   1680
```

atggcggagg cctacagtga gattgggatg aaaggcgagc gccggagggg caaggggcac 1740
gatggccttt accagggtct cagtacagcc accaaggaca cctacgacgc ccttcacatg 1800
caggccctgc cccctcgcta a 1821

<210> SEQ ID NO 40
<211> LENGTH: 606
<212> TYPE: PRT
<213> ORGANISM: Artificial Sequence
<220> FEATURE:
<223> OTHER INFORMATION: PLA2R-CAAR Construct 4026.CF1

<400> SEQUENCE: 40

Met Leu Leu Ser Pro Ser Leu Leu Leu Leu Leu Leu Leu Gly Ala Pro
1 5 10 15

Arg Gly Cys Ala Gly Ser Glu Gly Val Ala Ala Ala Leu Thr Pro Glu
20 25 30

Arg Leu Leu Glu Trp Gln Asp Lys Gly Ile Phe Val Ile Gln Ser Glu
35 40 45

Ser Leu Lys Lys Cys Ile Gln Ala Gly Lys Ser Val Leu Thr Leu Glu
50 55 60

Asn Cys Lys Gln Ala Asn Lys His Met Leu Trp Lys Trp Val Ser Asn
65 70 75 80

His Gly Leu Phe Asn Ile Gly Gly Ser Gly Cys Leu Gly Leu Asn Phe
85 90 95

Ser Ala Pro Glu Gln Pro Leu Ser Leu Tyr Glu Cys Asp Ser Thr Leu
100 105 110

Val Ser Leu Arg Trp Arg Cys Asn Arg Lys Met Ile Thr Gly Pro Leu
115 120 125

Gln Tyr Ser Val Gln Val Ala His Asp Asn Thr Val Val Ala Ser Arg
130 135 140

Lys Tyr Ile His Lys Trp Ile Ser Tyr Gly Ser Gly Gly Gly Asp Ile
145 150 155 160

Cys Glu Tyr Leu His Lys Asp Leu His Thr Ile Lys Gly Asn Thr His
165 170 175

Gly Met Pro Cys Met Phe Pro Phe Gln Tyr Asn His Gln Trp His His
180 185 190

Glu Cys Thr Arg Glu Gly Arg Glu Asp Asp Leu Leu Trp Cys Ala Thr
195 200 205

Thr Ser Arg Tyr Glu Arg Asp Glu Lys Trp Gly Phe Cys Pro Asp Pro
210 215 220

Thr Ser Ala Glu Val Gly Cys Asp Thr Ile Trp Glu Lys Asp Leu Asn
225 230 235 240

Ser His Ile Cys Tyr Gln Phe Asn Leu Leu Ser Ser Leu Ser Trp Ser
245 250 255

Glu Ala His Ser Ser Cys Gln Met Gln Gly Gly Thr Leu Leu Ser Ile
260 265 270

Thr Asp Glu Thr Glu Glu Asn Phe Ile Arg Glu His Met Ser Ser Lys
275 280 285

Thr Val Glu Val Trp Met Gly Leu Asn Gln Leu Asp Glu His Ala Gly
290 295 300

Trp Gln Trp Ser Asp Gly Thr Pro Leu Asn Tyr Leu Asn Trp Ser Pro
305 310 315 320

Glu Val Asn Phe Glu Pro Phe Val Glu Asp His Cys Gly Thr Phe Ser
325 330 335

-continued

Ser Phe Met Pro Ser Ala Trp Arg Ser Arg Asp Cys Glu Ser Thr Leu
340 345 350

Pro Tyr Ile Cys Lys Lys Tyr Leu Asn His Ile Asp His Glu Ile Val
355 360 365

Glu Lys Asp Ala Trp Lys Tyr Tyr Ala Thr His Cys Glu Ser Gly Thr
370 375 380

Thr Thr Pro Ala Pro Arg Pro Pro Thr Pro Ala Pro Thr Ile Ala Ser
385 390 395 400

Gln Pro Leu Ser Leu Arg Pro Glu Ala Cys Arg Pro Ala Ala Gly Gly
405 410 415

Ala Val His Thr Arg Gly Leu Asp Phe Ala Cys Asp Ile Tyr Ile Trp
420 425 430

Ala Pro Leu Ala Gly Thr Cys Gly Val Leu Leu Leu Ser Leu Val Ile
435 440 445

Thr Leu Tyr Cys Lys Arg Gly Arg Lys Lys Leu Leu Tyr Ile Phe Lys
450 455 460

Gln Pro Phe Met Arg Pro Val Gln Thr Thr Gln Glu Glu Asp Gly Cys
465 470 475 480

Ser Cys Arg Phe Pro Glu Glu Glu Glu Gly Gly Cys Glu Leu Arg Val
485 490 495

Lys Phe Ser Arg Ser Ala Asp Ala Pro Ala Tyr Lys Gln Gly Gln Asn
500 505 510

Gln Leu Tyr Asn Glu Leu Asn Leu Gly Arg Arg Glu Glu Tyr Asp Val
515 520 525

Leu Asp Lys Arg Arg Gly Arg Asp Pro Glu Met Gly Gly Lys Pro Arg
530 535 540

Arg Lys Asn Pro Gln Glu Gly Leu Tyr Asn Glu Leu Gln Lys Asp Lys
545 550 555 560

Met Ala Glu Ala Tyr Ser Glu Ile Gly Met Lys Gly Glu Arg Arg Arg
565 570 575

Gly Lys Gly His Asp Gly Leu Tyr Gln Gly Leu Ser Thr Ala Thr Lys
580 585 590

Asp Thr Tyr Asp Ala Leu His Met Gln Ala Leu Pro Pro Arg
595 600 605

<210> SEQ ID NO 41
<211> LENGTH: 4441
<212> TYPE: DNA
<213> ORGANISM: Homo sapiens

<400> SEQUENCE: 41
ccggagagcc cagtggttag cgatgctgct gtcgccgtcg ctgctgctgc tgctgctgct 60
gggggcgccg cggggctgcg ccgagggtgt ggcggcggcg cttacccccg agcggctcct 120
ggagtggcag gataaaggaa tatttgttat ccaaagtgag agtctcaaga aatgcattca 180
agcaggtaaa tcggttctga ccctggagaa ctgcaagcaa gcaaacaagc acatgctgtg 240
gaaatgggtt tcaaaccatg gcctctttaa cataggaggc agcggttgcc tgggcctgaa 300
tttctccgcc ccagagcagc cattaagctt atatgaatgt gactccaccc tcgtttcctt 360
acggtggcgc tgtaacagga agatgatcac aggcccgctg cagtactctg tccaggtggc 420
gcatgacaac acagtggtgg cctcacggaa gtatattcat aagtggattt cttatgggtc 480
aggtggtgga gacatttgtg aatatctaca caaagatttg catacaatca aagggaacac 540
ccacgggatg ccgtgtatgt ttcccttcca gtataaccat cagtggcatc atgaatgtac 600

```
ccgtgaaggt cgggaagatg acttactgtg gtgtgccacg acaagccgtt atgaaagaga    660
tgaaaagtgg ggattttgcc ctgatcccac ctctgcagaa gtaggttgtg atactatttg    720
ggagaaggac ctcaattcac acatttgcta ccagttcaac ctgctttcat ctctctcttg    780
gagtgaggca cattcttcat gccagatgca aggaggtacg ctgttaagta ttacagatga    840
aactgaagaa aatttcataa gggagcacat gagcagtaaa acagtggagg tgtggatggg    900
cctcaatcag ctggatgaac acgctggctg gcagtggtct gatggaacgc cgctcaacta    960
tctgaattgg agcccagagg taaattttga gccatttgtt gaagatcact gtggaacatt   1020
tagttcattt atgccaagtg cctggaggag tcgggattgt gagtccacct tgccatatat   1080
atgtaaaaaa tatctaaacc acattgatca tgaaatagtt gaaaaagatg cgtggaaata   1140
ttatgctacc cactgtgagc ctggctggaa tccctacaat cgtaattgct acaaacttca   1200
gaaagaagaa aagacctggc atgaggctct gcgttcttgt caggctgata acagtgcatt   1260
aatagacata acctcattag cagaggtgga gtttcttgta accctccttg gagatgaaaa   1320
tgcatcagaa acatggattg gtttgagcag caataaaatt ccagtttcct ttgaatggtc   1380
taatgactct tcagtcatct ttactaattg gcacacactt gagccccaca tttttccaaa   1440
tagaagccag ctgtgtgtct cagcagagca gtctgaggga cactggaaag tcaaaaattg   1500
tgaagaaaga ctttttaca tttgtaaaaa agcaggccat gtcctctctg atgctgaatc    1560
aggatgtcaa gagggatggg agagacatgg tggattctgt tacaaaattg acacagtcct   1620
tcgaagcttt gaccaagctt ccagcggtta ttactgtcct cctgcacttg taaccattac   1680
aaacaggttt gaacaggctt ttattaccag tttgatcagt agtgtggtaa aaatgaagga   1740
cagttatttt tggatagctc ttcaggacca aaatgatacg ggagaataca cttggaagcc   1800
agtagggcag aaacccgagc cggtgcagta cacacactgg aacacacacc agccgcgcta   1860
cagtggtggc tgtgttgcca tgcgaggaag gcatccactt ggtcgctggg aagtgaagca   1920
ctgtcggcac tttaaggcaa tgtccttgtg caagcagcca gttgaaaatc aggaaaaagc   1980
agagtatgaa gagagatggc cctttcaccc ctgctatttg gactgggagt cagagcctgg   2040
tctggccagt tgcttcaagg tatttcatag tgaaaaagtt ctgatgaaaa gaacatggag   2100
agaagctgaa gcattttgcg aagaatttgg agctcatctt gcaagctttg cccatattga   2160
ggaagagaat tttgtgaatg agctcttaca ttcaaaattt aattggacag aagaaaggca   2220
gttctggatt ggatttaata aaagaaaccc actgaatgcc ggctcatggg agtggtctga   2280
tagaactcct gttgtctctt cgtttttaga caacacttat tttggagaag atgcaagaaa   2340
ctgtgctgtt tataaggcaa acaaaacatt gctgccctta cactgtggtt ccaaacgtga   2400
atggatatgc aaaatcccaa gagatgtgaa acccaagatt ccgttctggt accagtacga   2460
tgtaccctgg ctcttttatc aggatgcaga ataccttttt catacctttg cctcagaatg   2520
gttgaacttt gagtttgtct gtagctggct gcacagtgat cttctcacaa ttcattctgc   2580
acatgagcaa gaattcatcc acagcaaaat aaaagcgcta tcaaagtatg gtgcaagttg   2640
gtggattgga cttcaagaag aaagagccaa tgatgaattt cgctggagag atggaacacc   2700
agtgatatac cagaactggg acacaggaag agaaagaact gtgaataatc agagccagag   2760
atgtggcttt atttcttcta taacaggact ctggggtagt gaagagtgtt cagtttctat   2820
gcctagtatc tgtaagcgaa aaaaggtttg gctcatagag aaaaagaaag atacaccaaa   2880
acaacatgga acgtgtccca aaggatggct atattttaac tataagtgcc ttctgctgaa   2940
```

-continued

```
tatccccaaa gacccaagca gttggaagaa ctggacgcat gctcaacatt tctgtgctga   3000

agaagggggg accctggtcg ccattgaaag tgaggtggag caagctttca ttactatgaa   3060

tctttttggc cagaccacca gtgtgtggat aggtttacaa aatgatgatt atgaaacatg   3120

gctaaatgga aagcctgtgg tatattctaa ctggtctcca tttgatataa taaatattcc   3180

aagtcacaat accactgaag ttcagaaaca cattcctctc tgtgccttac tctcaagtaa   3240

tcctaatttt catttcactg gaaaatggta ttttgaagac tgtggaaagg aaggctatgg   3300

gtttgtttgt gaaaaaatgc aagatacttc tggacacggt gtaaatacat ctgatatgta   3360

tccaatgccc aataccttag aatatggaaa cagaacttac aaaataatta atgcaaatat   3420

gacttggtat gcagcaataa aaacctgcct gatgcacaaa gcacaactgg tcagcatcac   3480

agaccagtat caccagtcct tcctcactgt tgtcctcaac cggctaggat atgcccactg   3540

gattggactg ttcaccacag ataatggtct taattttgac tggtctgatg gcaccaaatc   3600

ttctttcact tttggaaag atgaggagtc ctccctcctt ggtgactgcg tttttgccga   3660

cagcaacgga cgctggcata gcacagcctg cgagtcattt ctgcaaggtg ccatttgtca   3720

tgtgccacct gaaacaagac aatctgaaca cccagagttg tgctcagaaa catctattcc   3780

ctggataaaa tttaaaagta attgctacag tttttctaca gtcctagaca gtatgagttt   3840

tgaggctgct catgaatttt gcaaaaagga aggttctaat cttttaacaa tcaaggatga   3900

ggctgaaaat gcatttctcc tagaagagct gtttgctttt ggttcttctg tccagatggt   3960

ttggttgaat gctcaatttg atgatgaaac cataaagtgg tttgatggaa ctcccacaga   4020

ccagtcaaac tggggcattc ggaagccaga cacagactac ttcaagcccc atcattgtgt   4080

tgccttgagg atccctgaag gattatggca gctatccccg tgtcaagaaa aaaaaggctt   4140

tatatgtaaa atggaggcag atattcacac tgcagaggcg ctgccagaaa aaggaccaag   4200

tcacagcatc attcctcttg cggttgtact gacactgata gtcattgtgg ccatttgcac   4260

actttccttc tgcatataca agcataacgg tggcttcttc aggagacttg cagggtttcg   4320

gaatccttac tatcctgcaa ccaactttag tacagtatat ttagaagaaa atattctcat   4380

ttctgatctt gagaagagtg accaataata atgaggtcag agaatgccac agacaccagg   4440

g                                                                   4441
```

```
<210> SEQ ID NO 42
<211> LENGTH: 135
<212> TYPE: DNA
<213> ORGANISM: Artificial Sequence
<220> FEATURE:
<223> OTHER INFORMATION: CD8 alpha hinge domain

<400> SEQUENCE: 42

accacgacgc cagcgccgcg accaccaaca ccggcgccca ccatcgcgtc gcagcccctg     60

tccctgcgcc cagaggcgtg ccggccagcg gcggggggcg cagtgcacac gagggggctg    120

gacttcgcct gtgat                                                     135


<210> SEQ ID NO 43
<211> LENGTH: 45
<212> TYPE: PRT
<213> ORGANISM: Artificial Sequence
<220> FEATURE:
<223> OTHER INFORMATION: CD8 alpha hinge domain

<400> SEQUENCE: 43

Thr Thr Thr Pro Ala Pro Arg Pro Pro Thr Pro Ala Pro Thr Ile Ala
```

-continued

```
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 44
<211> LENGTH: 55
<212> TYPE: PRT
<213> ORGANISM: Artificial Sequence
<220> FEATURE:
<223> OTHER INFORMATION: CD8 alpha hinge domain

<400> SEQUENCE: 44

```
Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55
```

<210> SEQ ID NO 45
<211> LENGTH: 112
<212> TYPE: PRT
<213> ORGANISM: Artificial Sequence
<220> FEATURE:
<223> OTHER INFORMATION: CD3 zeta signaling domain

<400> SEQUENCE: 45

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 46
<211> LENGTH: 57
<212> TYPE: DNA
<213> ORGANISM: Artificial Sequence
<220> FEATURE:
<223> OTHER INFORMATION: IgG Signal peptide

<400> SEQUENCE: 46

```
atggagtttg ggctgagctg gctttttctt gtggctattt taaaaggtgt ccagtgc        57
```

<210> SEQ ID NO 47
<211> LENGTH: 396
<212> TYPE: DNA
<213> ORGANISM: Artificial Sequence
<220> FEATURE:

<223> OTHER INFORMATION: CysR

<400> SEQUENCE: 47

```
aaaggaatat ttgtcattca gtcagagtct ttgaaaaagt gcatacaggc tggaaaaagc     60
gtgcttaccc tggagaactg caagcaagct aataagcata tgctttggaa atgggttagc    120
aaccacggac tctttaatat cggaggctcc ggctgtctgg gcctgaactt cagtgcaccg    180
gagcaaccgc tttctctgta cgaatgtgat agcacacttg ttagtcttcg gtggcggtgt    240
aaccgaaaaa tgattacagg ccctctgcaa tatagtgttc aagtggccca cgacaataca    300
gttgtggcgt ctagaaaata tattcacaag tggatttcct acgggagcgg cggaggggat    360
atatgtgaat atcttcacaa agacttgcat acaatc                              396
```

<210> SEQ ID NO 48
<211> LENGTH: 19
<212> TYPE: PRT
<213> ORGANISM: Artificial Sequence
<220> FEATURE:
<223> OTHER INFORMATION: IgG Signal peptide

<400> SEQUENCE: 48

```
Met Glu Phe Gly Leu Ser Trp Leu Phe Leu Val Ala Ile Leu Lys Gly
1               5                   10                  15

Val Gln Cys
```

<210> SEQ ID NO 49
<211> LENGTH: 132
<212> TYPE: PRT
<213> ORGANISM: Artificial Sequence
<220> FEATURE:
<223> OTHER INFORMATION: CysR

<400> SEQUENCE: 49

```
Lys Gly Ile Phe Val Ile Gln Ser Glu Ser Leu Lys Lys Cys Ile Gln
1               5                   10                  15

Ala Gly Lys Ser Val Leu Thr Leu Glu Asn Cys Lys Gln Ala Asn Lys
            20                  25                  30

His Met Leu Trp Lys Trp Val Ser Asn His Gly Leu Phe Asn Ile Gly
        35                  40                  45

Gly Ser Gly Cys Leu Gly Leu Asn Phe Ser Ala Pro Glu Gln Pro Leu
    50                  55                  60

Ser Leu Tyr Glu Cys Asp Ser Thr Leu Val Ser Leu Arg Trp Arg Cys
65                  70                  75                  80

Asn Arg Lys Met Ile Thr Gly Pro Leu Gln Tyr Ser Val Gln Val Ala
                85                  90                  95

His Asp Asn Thr Val Val Ala Ser Arg Lys Tyr Ile His Lys Trp Ile
            100                 105                 110

Ser Tyr Gly Ser Gly Gly Gly Asp Ile Cys Glu Tyr Leu His Lys Asp
        115                 120                 125

Leu His Thr Ile
    130
```

<210> SEQ ID NO 50
<211> LENGTH: 990
<212> TYPE: DNA
<213> ORGANISM: Artificial Sequence
<220> FEATURE:
<223> OTHER INFORMATION: CysR-FNII-CTLD1

<400> SEQUENCE: 50

-continued

```
aaagggatct ttgttataca aagtgagagc ttgaaaaaat gtatacaggc tggcaaaagt      60

gtactgactc ttgaaaattg caaacaagcc aacaaacaca tgctgtggaa atgggtgtct     120

aatcacggtc tcttcaatat tggggggaagt ggatgcctcg gcctgaattt ctccgctccc   180

gaacagcccc tctcacttta tgagtgtgat tcaactctgg tgtccttgag gtggcgatgt     240

aaccgcaaga tgataaccgg ccccctccag tattccgtcc aagtagcaca cgacaatacc     300

gtggtggcat ctaggaaata cattcataag tggatatctt atggcagtgg tggcggtgac     360

atatgcgagt acctgcacaa ggacctccac acaataaagg ggaacacgca cgggatgccg     420

tgtatgttcc cgttccaata taatcatcaa tggcaccatg agtgtacgag agaggggcga     480

gaagacgacc tcctgtggtg tgcgaccacc tcaagatatg aacgggatga gaagtggggc     540

ttttgccccg acccaacctc cgccgaggtt ggttgcgaca ctatttggga aaaagatttg     600

aacagtcata tatgctatca atttaatttg ttgagttcac tctcctggag cgaagcgcac     660

agctcttgtc agatgcaagg tggtacattg cttagcatta ctgatgaaac tgaggagaat     720

ttcattaggg agcatatgtc ctcaaagaca gtagaggtgt ggatgggtct gaaccagctc     780

gacgaacacg ccggttggca gtggtcagat ggaacgcctc tgaattatct caactggtcc     840

cctgaggtca actttgaacc gtttgtggaa gatcattgtg gtactttttc cagttttatg     900

ccaagcgcct ggcgaagccg agactgcgag tctacgttgc cctatatctg caagaagtat     960

ttgaatcaca tagatcatga aattgttgaa                                      990
```

<210> SEQ ID NO 51
<211> LENGTH: 330
<212> TYPE: PRT
<213> ORGANISM: Artificial Sequence
<220> FEATURE:
<223> OTHER INFORMATION: CysR-FNII-CTLD1

<400> SEQUENCE: 51

```
Lys Gly Ile Phe Val Ile Gln Ser Glu Ser Leu Lys Lys Cys Ile Gln
1               5                   10                  15

Ala Gly Lys Ser Val Leu Thr Leu Glu Asn Cys Lys Gln Ala Asn Lys
            20                  25                  30

His Met Leu Trp Lys Trp Val Ser Asn His Gly Leu Phe Asn Ile Gly
        35                  40                  45

Gly Ser Gly Cys Leu Gly Leu Asn Phe Ser Ala Pro Glu Gln Pro Leu
    50                  55                  60

Ser Leu Tyr Glu Cys Asp Ser Thr Leu Val Ser Leu Arg Trp Arg Cys
65                  70                  75                  80

Asn Arg Lys Met Ile Thr Gly Pro Leu Gln Tyr Ser Val Gln Val Ala
                85                  90                  95

His Asp Asn Thr Val Val Ala Ser Arg Lys Tyr Ile His Lys Trp Ile
            100                 105                 110

Ser Tyr Gly Ser Gly Gly Gly Asp Ile Cys Glu Tyr Leu His Lys Asp
        115                 120                 125

Leu His Thr Ile Lys Gly Asn Thr His Gly Met Pro Cys Met Phe Pro
    130                 135                 140

Phe Gln Tyr Asn His Gln Trp His His Glu Cys Thr Arg Glu Gly Arg
145                 150                 155                 160

Glu Asp Asp Leu Leu Trp Cys Ala Thr Thr Ser Arg Tyr Glu Arg Asp
                165                 170                 175

Glu Lys Trp Gly Phe Cys Pro Asp Pro Thr Ser Ala Glu Val Gly Cys
```

```
            180                 185                 190

Asp Thr Ile Trp Glu Lys Asp Leu Asn Ser His Ile Cys Tyr Gln Phe
        195                 200                 205

Asn Leu Leu Ser Ser Leu Ser Trp Ser Glu Ala His Ser Ser Cys Gln
    210                 215                 220

Met Gln Gly Gly Thr Leu Leu Ser Ile Thr Asp Glu Thr Glu Glu Asn
225                 230                 235                 240

Phe Ile Arg Glu His Met Ser Ser Lys Thr Val Glu Val Trp Met Gly
                245                 250                 255

Leu Asn Gln Leu Asp Glu His Ala Gly Trp Gln Trp Ser Asp Gly Thr
            260                 265                 270

Pro Leu Asn Tyr Leu Asn Trp Ser Pro Glu Val Asn Phe Glu Pro Phe
        275                 280                 285

Val Glu Asp His Cys Gly Thr Phe Ser Ser Phe Met Pro Ser Ala Trp
    290                 295                 300

Arg Ser Arg Asp Cys Glu Ser Thr Leu Pro Tyr Ile Cys Lys Lys Tyr
305                 310                 315                 320

Leu Asn His Ile Asp His Glu Ile Val Glu
                325                 330


<210> SEQ ID NO 52
<211> LENGTH: 1848
<212> TYPE: DNA
<213> ORGANISM: Artificial Sequence
<220> FEATURE:
<223> OTHER INFORMATION: CysR-FNII-CTLD1-3

<400> SEQUENCE: 52

aaagggattt tcgtgataca gtccgagagt ctcaaaaagt gtatccaggc aggcaaaagt      60

gttctcactc tggaaaactg caaacaagcg aacaagcaca tgttgtggaa gtgggttagt     120

aaccatggac tgttcaacat cggaggtagt ggatgccttg gtctcaattt ctctgctccg     180

gaacagcctt tgtcactgta cgaatgcgac tccactctcg ttagtcttag atggcgatgc     240

aatcgcaaaa tgattacggg accacttcaa tattcagttc aagtggcaca tgataacacc     300

gtagtggcct cacggaaata catccataaa tggatttctt atggtagcgg gggcggcgat     360

atatgtgaat acctccataa ggatctccac accattaagg gtaatactca cggtatgccg     420

tgtatgtttc cttttcagta caatcatcag tggcatcatg aatgcacgag ggaaggacgc     480

gaggacgatt tgctctggtg cgcaaccacc tcacgctacg agagagacga aaaatggggc     540

ttttgcccgg accccactag tgctgaggta ggatgtgata cgatttggga aaaggatttg     600

aattctcata tttgctacca gtttaatctt ctttcatccc tgtcctggtc tgaggctcat     660

tctagttgcc agatgcaagg tgggactttg ctttcaatta ctgacgagac tgaggaaaat     720

tttatccgag agcatatgtc ttctaaaacc gtagaggtat ggatgggcct gaaccaattg     780

gacgaacacg cgggctggca gtggagcgac gggacacctc tcaactacct taattggagc     840

cctgaggtaa actttgaacc gtttgtcgag gatcactgcg gaactttcag cagcttcatg     900

cctagtgcat ggcggtcccg agactgtgag agcacccttc catacatatg taaaaaatac     960

ctcaatcaca tagaccacga gatcgtagag aaggatgcat ggaaatatta tgctacgcac    1020

tgtgagccgg gatggaatcc ttataaccgc aactgttaca agctgcaaaa agaagagaag    1080

acatggcatg aggcgctgcg ctcatgtcaa gcggacaatt ctgcacttat agatataact    1140

agtttggcgg aggtagaatt tttggttacg cttctcggcg atgagaatgc gtccgagacg    1200
```

-continued

```
tggatagggt tgtcaagcaa taaaattcct gtaagttttg aatggtcaaa tgactcttct   1260

gtcatcttca ccaattggca cacactcgaa ccccatatct tcccaaaccg aagccagttg   1320

tgtgtcagcg ctgagcaatc agaaggacat tggaaagtta aaaactgtga agaaagactg   1380

ttctacatct gtaagaaggc aggacatgtg ctttcagatg cggaaagcgg ctgtcaagaa   1440

ggttgggagc gccatggagg tttctgttat aaaatcgaca cagttttgcg atctttcgat   1500

caggcttcaa gcgggtacta ttgtcctcct gcactggtta caatcacgaa ccggtttgaa   1560

caggctttta taacttcttt gatttccagc gtggttaaaa tgaaggactc ttatttctgg   1620

atagccctgc aagaccaaaa tgataccggt gagtacacat ggaaaccggt aggtcaaaag   1680

ccagagccag tccagtacac tcattggaat acccaccagc ctaggtactc cggcgggtgt   1740

gtggcgatgc ggggtcgcca ccctctcgga cgctgggagg tgaagcattg ccgccacttc   1800

aaggcgatga gcttgtgtaa acagcccgtc gaaaatcagg aaaaggca                 1848


<210> SEQ ID NO 53
<211> LENGTH: 616
<212> TYPE: PRT
<213> ORGANISM: Artificial Sequence
<220> FEATURE:
<223> OTHER INFORMATION: CysR-FNII-CTLD1-3

<400> SEQUENCE: 53

Lys Gly Ile Phe Val Ile Gln Ser Glu Ser Leu Lys Lys Cys Ile Gln
1               5                   10                  15

Ala Gly Lys Ser Val Leu Thr Leu Glu Asn Cys Lys Gln Ala Asn Lys
            20                  25                  30

His Met Leu Trp Lys Trp Val Ser Asn His Gly Leu Phe Asn Ile Gly
        35                  40                  45

Gly Ser Gly Cys Leu Gly Leu Asn Phe Ser Ala Pro Glu Gln Pro Leu
    50                  55                  60

Ser Leu Tyr Glu Cys Asp Ser Thr Leu Val Ser Leu Arg Trp Arg Cys
65                  70                  75                  80

Asn Arg Lys Met Ile Thr Gly Pro Leu Gln Tyr Ser Val Gln Val Ala
                85                  90                  95

His Asp Asn Thr Val Val Ala Ser Arg Lys Tyr Ile His Lys Trp Ile
            100                 105                 110

Ser Tyr Gly Ser Gly Gly Gly Asp Ile Cys Glu Tyr Leu His Lys Asp
        115                 120                 125

Leu His Thr Ile Lys Gly Asn Thr His Gly Met Pro Cys Met Phe Pro
    130                 135                 140

Phe Gln Tyr Asn His Gln Trp His His Glu Cys Thr Arg Glu Gly Arg
145                 150                 155                 160

Glu Asp Asp Leu Leu Trp Cys Ala Thr Thr Ser Arg Tyr Glu Arg Asp
                165                 170                 175

Glu Lys Trp Gly Phe Cys Pro Asp Pro Thr Ser Ala Glu Val Gly Cys
            180                 185                 190

Asp Thr Ile Trp Glu Lys Asp Leu Asn Ser His Ile Cys Tyr Gln Phe
        195                 200                 205

Asn Leu Leu Ser Ser Leu Ser Trp Ser Glu Ala His Ser Ser Cys Gln
    210                 215                 220

Met Gln Gly Gly Thr Leu Leu Ser Ile Thr Asp Glu Thr Glu Glu Asn
225                 230                 235                 240

Phe Ile Arg Glu His Met Ser Ser Lys Thr Val Glu Val Trp Met Gly
                245                 250                 255
```

```
Leu Asn Gln Leu Asp Glu His Ala Gly Trp Gln Trp Ser Asp Gly Thr
            260                 265                 270

Pro Leu Asn Tyr Leu Asn Trp Ser Pro Glu Val Asn Phe Glu Pro Phe
        275                 280                 285

Val Glu Asp His Cys Gly Thr Phe Ser Ser Phe Met Pro Ser Ala Trp
    290                 295                 300

Arg Ser Arg Asp Cys Glu Ser Thr Leu Pro Tyr Ile Cys Lys Lys Tyr
305                 310                 315                 320

Leu Asn His Ile Asp His Glu Ile Val Glu Lys Asp Ala Trp Lys Tyr
                325                 330                 335

Tyr Ala Thr His Cys Glu Pro Gly Trp Asn Pro Tyr Asn Arg Asn Cys
            340                 345                 350

Tyr Lys Leu Gln Lys Glu Glu Lys Thr Trp His Glu Ala Leu Arg Ser
        355                 360                 365

Cys Gln Ala Asp Asn Ser Ala Leu Ile Asp Ile Thr Ser Leu Ala Glu
    370                 375                 380

Val Glu Phe Leu Val Thr Leu Leu Gly Asp Glu Asn Ala Ser Glu Thr
385                 390                 395                 400

Trp Ile Gly Leu Ser Ser Asn Lys Ile Pro Val Ser Phe Glu Trp Ser
                405                 410                 415

Asn Asp Ser Ser Val Ile Phe Thr Asn Trp His Thr Leu Glu Pro His
            420                 425                 430

Ile Phe Pro Asn Arg Ser Gln Leu Cys Val Ser Ala Glu Gln Ser Glu
        435                 440                 445

Gly His Trp Lys Val Lys Asn Cys Glu Glu Arg Leu Phe Tyr Ile Cys
    450                 455                 460

Lys Lys Ala Gly His Val Leu Ser Asp Ala Glu Ser Gly Cys Gln Glu
465                 470                 475                 480

Gly Trp Glu Arg His Gly Gly Phe Cys Tyr Lys Ile Asp Thr Val Leu
                485                 490                 495

Arg Ser Phe Asp Gln Ala Ser Ser Gly Tyr Tyr Cys Pro Pro Ala Leu
            500                 505                 510

Val Thr Ile Thr Asn Arg Phe Glu Gln Ala Phe Ile Thr Ser Leu Ile
        515                 520                 525

Ser Ser Val Val Lys Met Lys Asp Ser Tyr Phe Trp Ile Ala Leu Gln
    530                 535                 540

Asp Gln Asn Asp Thr Gly Glu Tyr Thr Trp Lys Pro Val Gly Gln Lys
545                 550                 555                 560

Pro Glu Pro Val Gln Tyr Thr His Trp Asn Thr His Gln Pro Arg Tyr
                565                 570                 575

Ser Gly Gly Cys Val Ala Met Arg Gly Arg His Pro Leu Gly Arg Trp
            580                 585                 590

Glu Val Lys His Cys Arg His Phe Lys Ala Met Ser Leu Cys Lys Gln
        595                 600                 605

Pro Val Glu Asn Gln Glu Lys Ala
    610                 615
```

<210> SEQ ID NO 54
<211> LENGTH: 2268
<212> TYPE: DNA
<213> ORGANISM: Artificial Sequence
<220> FEATURE:
<223> OTHER INFORMATION: CysR-FNII-CTLD1-3 7

<400> SEQUENCE: 54

```
aaagggattt tcgtgataca gtccgagagt ctcaaaaagt gtatccaggc aggcaaaagt     60
gttctcactc tggaaaactg caaacaagcg aacaagcaca tgttgtggaa gtgggttagt    120
aaccatggac tgttcaacat cggaggtagt ggatgccttg gtctcaattt ctctgctccg    180
gaacagcctt tgtcactgta cgaatgcgac tccactctcg ttagtcttag atggcgatgc    240
aatcgcaaaa tgattacggg accacttcaa tattcagttc aagtggcaca tgataacacc    300
gtagtggcct cacggaaata catccataaa tggatttctt atggtagcgg gggcggcgat    360
atatgtgaat acctccataa ggatctccac accattaagg gtaatactca cggtatgccg    420
tgtatgtttc cttttcagta caatcatcag tggcatcatg aatgcacgag ggaaggacgc    480
gaggacgatt tgctctggtg cgcaaccacc tcacgctacg agagagacga aaaatggggc    540
ttttgcccgg accccactag tgctgaggta ggatgtgata cgatttggga aaaggatttg    600
aattctcata tttgctacca gtttaatctt ctttcatccc tgtcctggtc tgaggctcat    660
tctagttgcc agatgcaagg tgggactttg ctttcaatta ctgacgagac tgaggaaaat    720
tttatccgag agcatatgtc ttctaaaacc gtagaggtat ggatgggcct gaaccaattg    780
gacgaacacg cgggctggca gtggagcgac gggacacctc tcaactacct taattggagc    840
cctgaggtaa actttgaacc gtttgtcgag gatcactgcg gaactttcag cagcttcatg    900
cctagtgcat ggcggtcccg agactgtgag agcacccttc catacatatg taaaaaatac    960
ctcaatcaca tagaccacga gatcgtagag aaggatgcat ggaaatatta tgctacgcac   1020
tgtgagccgg gatggaatcc ttataaccgc aactgttaca agctgcaaaa agaagagaag   1080
acatggcatg aggcgctgcg ctcatgtcaa gcggacaatt ctgcacttat agatataact   1140
agtttggcgg aggtagaatt tttggttacg cttctcggcg atgagaatgc gtccgagacg   1200
tggatagggt tgtcaagcaa taaaattcct gtaagttttg aatggtcaaa tgactcttct   1260
gtcatcttca ccaattggca cacactcgaa ccccatatct tcccaaaccg aagccagttg   1320
tgtgtcagcg ctgagcaatc agaaggacat tggaaagtta aaaactgtga agaaagactg   1380
ttctacatct gtaagaaggc aggacatgtg ctttcagatg cggaaagcgg ctgtcaagaa   1440
ggttgggagc gccatggagg tttctgttat aaaatcgaca cagttttgcg atctttcgat   1500
caggcttcaa gcgggtacta ttgtcctcct gcactggtta caatcacgaa ccggtttgaa   1560
caggctttta taacttcttt gatttccagc gtggttaaaa tgaaggactc ttatttctgg   1620
atagccctgc aagaccaaaa tgataccggt gagtacacat ggaaaccggt aggtcaaaag   1680
ccagagccag tccagtacac tcattggaat acccaccagc ctaggtactc cggcgggtgt   1740
gtggcgatgc ggggtcgcca ccctctcgga cgctgggagg tgaagcattg ccgccacttc   1800
aaggcgatga gcttgtgtaa acagcccgtc gaaaatcagg aaaaggcagt taacacatct   1860
gatatgtacc ctatgcctaa cacactcgaa tatgggaata ggacgtacaa gattataaac   1920
gcgaacatga cgtggtatgc tgcaatcaag acgtgcctca tgcacaaagc tcagcttgtg   1980
tctattactg accaatacca ccaatcattt ttgacagtcg tgttgaatcg attggggtac   2040
gcccattgga tcggtctctt cacgacggac aatgggctca attttgactg gagtgacggt   2100
actaaatcat cctttacttt ttggaaggat gaagaaagtt ctctgttggg cgattgcgtg   2160
tttgctgact caaatggccg atggcattcc acagcctgtg aaagttttct gcagggagct   2220
atttgccacg tgcctcccga aacgcggcag tccgaacacc cggaattg                2268
```

<210> SEQ ID NO 55

```
<211> LENGTH: 756
<212> TYPE: PRT
<213> ORGANISM: Artificial Sequence
<220> FEATURE:
<223> OTHER INFORMATION: CysR-FNII-CTLD1-3 7

<400> SEQUENCE: 55

Lys Gly Ile Phe Val Ile Gln Ser Glu Ser Leu Lys Lys Cys Ile Gln
1               5                   10                  15

Ala Gly Lys Ser Val Leu Thr Leu Glu Asn Cys Lys Gln Ala Asn Lys
            20                  25                  30

His Met Leu Trp Lys Trp Val Ser Asn His Gly Leu Phe Asn Ile Gly
        35                  40                  45

Gly Ser Gly Cys Leu Gly Leu Asn Phe Ser Ala Pro Glu Gln Pro Leu
    50                  55                  60

Ser Leu Tyr Glu Cys Asp Ser Thr Leu Val Ser Leu Arg Trp Arg Cys
65                  70                  75                  80

Asn Arg Lys Met Ile Thr Gly Pro Leu Gln Tyr Ser Val Gln Val Ala
                85                  90                  95

His Asp Asn Thr Val Val Ala Ser Arg Lys Tyr Ile His Lys Trp Ile
            100                 105                 110

Ser Tyr Gly Ser Gly Gly Gly Asp Ile Cys Glu Tyr Leu His Lys Asp
        115                 120                 125

Leu His Thr Ile Lys Gly Asn Thr His Gly Met Pro Cys Met Phe Pro
    130                 135                 140

Phe Gln Tyr Asn His Gln Trp His His Glu Cys Thr Arg Glu Gly Arg
145                 150                 155                 160

Glu Asp Asp Leu Leu Trp Cys Ala Thr Thr Ser Arg Tyr Glu Arg Asp
                165                 170                 175

Glu Lys Trp Gly Phe Cys Pro Asp Pro Thr Ser Ala Glu Val Gly Cys
            180                 185                 190

Asp Thr Ile Trp Glu Lys Asp Leu Asn Ser His Ile Cys Tyr Gln Phe
        195                 200                 205

Asn Leu Leu Ser Ser Leu Ser Trp Ser Glu Ala His Ser Ser Cys Gln
    210                 215                 220

Met Gln Gly Gly Thr Leu Leu Ser Ile Thr Asp Glu Thr Glu Glu Asn
225                 230                 235                 240

Phe Ile Arg Glu His Met Ser Ser Lys Thr Val Glu Val Trp Met Gly
                245                 250                 255

Leu Asn Gln Leu Asp Glu His Ala Gly Trp Gln Trp Ser Asp Gly Thr
            260                 265                 270

Pro Leu Asn Tyr Leu Asn Trp Ser Pro Glu Val Asn Phe Glu Pro Phe
        275                 280                 285

Val Glu Asp His Cys Gly Thr Phe Ser Ser Phe Met Pro Ser Ala Trp
    290                 295                 300

Arg Ser Arg Asp Cys Glu Ser Thr Leu Pro Tyr Ile Cys Lys Lys Tyr
305                 310                 315                 320

Leu Asn His Ile Asp His Glu Ile Val Glu Lys Asp Ala Trp Lys Tyr
                325                 330                 335

Tyr Ala Thr His Cys Glu Pro Gly Trp Asn Pro Tyr Asn Arg Asn Cys
            340                 345                 350

Tyr Lys Leu Gln Lys Glu Glu Lys Thr Trp His Glu Ala Leu Arg Ser
        355                 360                 365

Cys Gln Ala Asp Asn Ser Ala Leu Ile Asp Ile Thr Ser Leu Ala Glu
    370                 375                 380
```

```
Val Glu Phe Leu Val Thr Leu Leu Gly Asp Glu Asn Ala Ser Glu Thr
385                 390                 395                 400

Trp Ile Gly Leu Ser Ser Asn Lys Ile Pro Val Ser Phe Glu Trp Ser
                405                 410                 415

Asn Asp Ser Ser Val Ile Phe Thr Asn Trp His Thr Leu Glu Pro His
            420                 425                 430

Ile Phe Pro Asn Arg Ser Gln Leu Cys Val Ser Ala Glu Gln Ser Glu
        435                 440                 445

Gly His Trp Lys Val Lys Asn Cys Glu Glu Arg Leu Phe Tyr Ile Cys
    450                 455                 460

Lys Lys Ala Gly His Val Leu Ser Asp Ala Glu Ser Gly Cys Gln Glu
465                 470                 475                 480

Gly Trp Glu Arg His Gly Gly Phe Cys Tyr Lys Ile Asp Thr Val Leu
                485                 490                 495

Arg Ser Phe Asp Gln Ala Ser Ser Gly Tyr Tyr Cys Pro Pro Ala Leu
            500                 505                 510

Val Thr Ile Thr Asn Arg Phe Glu Gln Ala Phe Ile Thr Ser Leu Ile
        515                 520                 525

Ser Ser Val Val Lys Met Lys Asp Ser Tyr Phe Trp Ile Ala Leu Gln
    530                 535                 540

Asp Gln Asn Asp Thr Gly Glu Tyr Thr Trp Lys Pro Val Gly Gln Lys
545                 550                 555                 560

Pro Glu Pro Val Gln Tyr Thr His Trp Asn Thr His Gln Pro Arg Tyr
                565                 570                 575

Ser Gly Gly Cys Val Ala Met Arg Gly Arg His Pro Leu Gly Arg Trp
            580                 585                 590

Glu Val Lys His Cys Arg His Phe Lys Ala Met Ser Leu Cys Lys Gln
        595                 600                 605

Pro Val Glu Asn Gln Glu Lys Ala Val Asn Thr Ser Asp Met Tyr Pro
    610                 615                 620

Met Pro Asn Thr Leu Glu Tyr Gly Asn Arg Thr Tyr Lys Ile Ile Asn
625                 630                 635                 640

Ala Asn Met Thr Trp Tyr Ala Ala Ile Lys Thr Cys Leu Met His Lys
                645                 650                 655

Ala Gln Leu Val Ser Ile Thr Asp Gln Tyr His Gln Ser Phe Leu Thr
            660                 665                 670

Val Val Leu Asn Arg Leu Gly Tyr Ala His Trp Ile Gly Leu Phe Thr
        675                 680                 685

Thr Asp Asn Gly Leu Asn Phe Asp Trp Ser Asp Gly Thr Lys Ser Ser
    690                 695                 700

Phe Thr Phe Trp Lys Asp Glu Glu Ser Ser Leu Leu Gly Asp Cys Val
705                 710                 715                 720

Phe Ala Asp Ser Asn Gly Arg Trp His Ser Thr Ala Cys Glu Ser Phe
                725                 730                 735

Leu Gln Gly Ala Ile Cys His Val Pro Pro Glu Thr Arg Gln Ser Glu
            740                 745                 750

His Pro Glu Leu
        755
```

<210> SEQ ID NO 56
<211> LENGTH: 1410
<212> TYPE: DNA
<213> ORGANISM: Artificial Sequence
<220> FEATURE:

-continued

<223> OTHER INFORMATION: CysR-FNII-CTLD1 7

<400> SEQUENCE: 56

```
aaaggcatct tcgtaatcca gtcagaaagt ttgaaaaaat gtatccaagc tggcaaatca     60
gtacttaccc ttgagaactg caagcaagcc aataaacata tgctgtggaa atgggtctca    120
aaccacggcc tcttcaatat tggtgggtca ggttgcttgg ggttgaattt ctccgcccca    180
gagcaaccac tcagccttta cgagtgtgat tccacacttg tctctttgcg atggcgctgc    240
aataggaaaa tgatcacagg ccccttcag tactctgtgc aagttgctca tgataacaca     300
gtcgtggcga gtcggaaata tattcacaaa tggatttctt atgggagtgg tggaggagat    360
atatgcgagt atttgcataa ggacttgcac accatcaagg gaaacactca cggtatgcca    420
tgtatgtttc cgttccaata taatcatcaa tggcaccacg aatgtacccg agagggacgc    480
gaggacgatc ttctttggtg cgccacaacc tctcgatatg aacgagatga gaagtggggg    540
ttttgtcctg acccaaccag tgcagaagta gggtgcgata ccatctggga gaaagacttg    600
aactcacaca tatgctatca gtttaatttg ttgtcttctt tgtcatggag cgaagctcat    660
tcatcatgcc agatgcaggg cgggacactg ctttctatca ccgacgagac tgaggaaaat    720
tttatccgcg agcacatgtc aagcaagaca gttgaggttt ggatggggct caatcaactg    780
gacgaacacg cagggtggca gtggtccgat ggcactccgc tcaactacct taactggagc    840
ccagaggtga actttgagcc gtttgtcgaa gatcactgtg gtacttttag ctccttcatg    900
ccgtccgcat ggagaagtcg cgactgcgag tcaaccctcc cttacatctg taagaaatac    960
ctcaaccaca tagatcacga aatcgtagag gtcaatacgt ccgacatgta cccaatgcca   1020
aatacgttgg aatatgggaa taggacatac aagataatta acgcaaatat gacgtggtat   1080
gccgcaatca aaacgtgcct catgcacaag gcacagctcg tgtcaattac ggaccagtac   1140
caccaatcat ttctcacagt cgttcttaat cgattgggtt atgcacactg gataggcttg   1200
ttcacgacgg acaatggttt gaactttgac tggtccgatg gaactaaaag ttctttcact   1260
ttttggaagg atgaggagtc ctccttgctc ggggactgcg tcttcgcaga ttcaaacggg   1320
cgctggcact caacggcatg tgagtccttc ctgcagggag ctatatgcca tgtgccacca   1380
gaaacacgcc agtctgagca ccctgagttg                                     1410
```

<210> SEQ ID NO 57
<211> LENGTH: 470
<212> TYPE: PRT
<213> ORGANISM: Artificial Sequence
<220> FEATURE:
<223> OTHER INFORMATION: CysR-FNII-CTLD1 7

<400> SEQUENCE: 57

```
Lys Gly Ile Phe Val Ile Gln Ser Glu Ser Leu Lys Lys Cys Ile Gln
1               5                   10                  15

Ala Gly Lys Ser Val Leu Thr Leu Glu Asn Cys Lys Gln Ala Asn Lys
            20                  25                  30

His Met Leu Trp Lys Trp Val Ser Asn His Gly Leu Phe Asn Ile Gly
        35                  40                  45

Gly Ser Gly Cys Leu Gly Leu Asn Phe Ser Ala Pro Glu Gln Pro Leu
    50                  55                  60

Ser Leu Tyr Glu Cys Asp Ser Thr Leu Val Ser Leu Arg Trp Arg Cys
65                  70                  75                  80

Asn Arg Lys Met Ile Thr Gly Pro Leu Gln Tyr Ser Val Gln Val Ala
                85                  90                  95
```

```
His Asp Asn Thr Val Val Ala Ser Arg Lys Tyr Ile His Lys Trp Ile
            100                 105                 110

Ser Tyr Gly Ser Gly Gly Gly Asp Ile Cys Glu Tyr Leu His Lys Asp
        115                 120                 125

Leu His Thr Ile Lys Gly Asn Thr His Gly Met Pro Cys Met Phe Pro
    130                 135                 140

Phe Gln Tyr Asn His Gln Trp His His Glu Cys Thr Arg Glu Gly Arg
145                 150                 155                 160

Glu Asp Asp Leu Leu Trp Cys Ala Thr Thr Ser Arg Tyr Glu Arg Asp
                165                 170                 175

Glu Lys Trp Gly Phe Cys Pro Asp Pro Thr Ser Ala Glu Val Gly Cys
            180                 185                 190

Asp Thr Ile Trp Glu Lys Asp Leu Asn Ser His Ile Cys Tyr Gln Phe
        195                 200                 205

Asn Leu Leu Ser Ser Leu Ser Trp Ser Glu Ala His Ser Ser Cys Gln
    210                 215                 220

Met Gln Gly Gly Thr Leu Leu Ser Ile Thr Asp Glu Thr Glu Glu Asn
225                 230                 235                 240

Phe Ile Arg Glu His Met Ser Ser Lys Thr Val Glu Val Trp Met Gly
                245                 250                 255

Leu Asn Gln Leu Asp Glu His Ala Gly Trp Gln Trp Ser Asp Gly Thr
            260                 265                 270

Pro Leu Asn Tyr Leu Asn Trp Ser Pro Glu Val Asn Phe Glu Pro Phe
        275                 280                 285

Val Glu Asp His Cys Gly Thr Phe Ser Ser Phe Met Pro Ser Ala Trp
    290                 295                 300

Arg Ser Arg Asp Cys Glu Ser Thr Leu Pro Tyr Ile Cys Lys Lys Tyr
305                 310                 315                 320

Leu Asn His Ile Asp His Glu Ile Val Glu Val Asn Thr Ser Asp Met
                325                 330                 335

Tyr Pro Met Pro Asn Thr Leu Glu Tyr Gly Asn Arg Thr Tyr Lys Ile
            340                 345                 350

Ile Asn Ala Asn Met Thr Trp Tyr Ala Ala Ile Lys Thr Cys Leu Met
        355                 360                 365

His Lys Ala Gln Leu Val Ser Ile Thr Asp Gln Tyr His Gln Ser Phe
    370                 375                 380

Leu Thr Val Val Leu Asn Arg Leu Gly Tyr Ala His Trp Ile Gly Leu
385                 390                 395                 400

Phe Thr Thr Asp Asn Gly Leu Asn Phe Asp Trp Ser Asp Gly Thr Lys
                405                 410                 415

Ser Ser Phe Thr Phe Trp Lys Asp Glu Glu Ser Ser Leu Leu Gly Asp
            420                 425                 430

Cys Val Phe Ala Asp Ser Asn Gly Arg Trp His Ser Thr Ala Cys Glu
        435                 440                 445

Ser Phe Leu Gln Gly Ala Ile Cys His Val Pro Pro Glu Thr Arg Gln
    450                 455                 460

Ser Glu His Pro Glu Leu
465                 470
```

<210> SEQ ID NO 58
<211> LENGTH: 1251
<212> TYPE: DNA
<213> ORGANISM: Artificial Sequence
<220> FEATURE:

<223> OTHER INFORMATION: CysR-CTLD1 7

<400> SEQUENCE: 58

```
aaaggaatct tcgtaattca atctgagagt ctgaaaaaat gtattcaggc cggtaagagc     60
gtactcacgc ttgaaaattg caaacaggcc aacaaacaca tgctttggaa atgggtttca    120
aatcacgggt tgtttaacat agggggatca ggatgtctgg gccttaactt ttccgcacct    180
gaacaacctc ttagtctgta tgagtgtgac tcaacgctgg tctccttgcg ctggagatgc    240
aatcggaaga tgataaccgg gcccctccag tattccgttc aggtcgccca cgataatact    300
gttgttgcat cccgaaaata tattcataag tggatctcct acgggagtgg agggggcgat    360
atttgtgaat acctccacaa ggatctgcac actatcactt ctgcggaagt aggctgtgac    420
acaatctggg agaaagatct gaattcacac atttgctatc agttcaatct tctgagttct    480
ttgagctggt ccgaagcaca ttcatcctgt cagatgcaag gtggaacact cttgtcaata    540
acagatgaaa cggaagagaa ctttattaga gaacatatgt cctcaaagac tgtggaggtg    600
tggatgggac ttaaccagct cgatgaacat gcaggatggc agtggagtga cggaacgcca    660
ctgaactacc tgaattggag cccagaggtg aatttcgagc ctttcgtaga ggaccattgc    720
ggtacttttt catcttttat gcccagcgca tggagatccc gagattgtga aagcacgctg    780
ccctatattt gtaaaaagta cctgaaccac atagatcatg agatagttga ggtaaataca    840
agtgatatgt accccatgcc gaacacactc gagtacggaa atagaaccta caagataatc    900
aacgctaaca tgacctggta cgcggccatt aagacctgcc tcatgcacaa ggctcaactc    960
gtcagtatta ctgaccaata tcaccagtca tttctcaccg tcgtgttgaa tcgcctcggt   1020
tacgcccact ggatcggttt gtttacaacg gacaatggac tcaatttcga ttggtcagac   1080
ggaaccaaat ctagttttac cttctggaaa gacgaggaat caagcctgct tggggactgc   1140
gtatttgcgg actctaatgg ccgatggcat agtacagcgt gtgagagctt tttgcagggg   1200
gcgatttgtc atgttccgcc ggaaacccgc caaagcgagc atccagaatt g            1251
```

<210> SEQ ID NO 59
<211> LENGTH: 417
<212> TYPE: PRT
<213> ORGANISM: Artificial Sequence
<220> FEATURE:
<223> OTHER INFORMATION: CysR-CTLD1 7

<400> SEQUENCE: 59

```
Lys Gly Ile Phe Val Ile Gln Ser Glu Ser Leu Lys Lys Cys Ile Gln
1               5                   10                  15

Ala Gly Lys Ser Val Leu Thr Leu Glu Asn Cys Lys Gln Ala Asn Lys
            20                  25                  30

His Met Leu Trp Lys Trp Val Ser Asn His Gly Leu Phe Asn Ile Gly
        35                  40                  45

Gly Ser Gly Cys Leu Gly Leu Asn Phe Ser Ala Pro Glu Gln Pro Leu
    50                  55                  60

Ser Leu Tyr Glu Cys Asp Ser Thr Leu Val Ser Leu Arg Trp Arg Cys
65                  70                  75                  80

Asn Arg Lys Met Ile Thr Gly Pro Leu Gln Tyr Ser Val Gln Val Ala
                85                  90                  95

His Asp Asn Thr Val Val Ala Ser Arg Lys Tyr Ile His Lys Trp Ile
            100                 105                 110

Ser Tyr Gly Ser Gly Gly Gly Asp Ile Cys Glu Tyr Leu His Lys Asp
        115                 120                 125
```

```
Leu His Thr Ile Thr Ser Ala Glu Val Gly Cys Asp Thr Ile Trp Glu
    130                 135                 140

Lys Asp Leu Asn Ser His Ile Cys Tyr Gln Phe Asn Leu Leu Ser Ser
145                 150                 155                 160

Leu Ser Trp Ser Glu Ala His Ser Ser Cys Gln Met Gln Gly Gly Thr
                165                 170                 175

Leu Leu Ser Ile Thr Asp Glu Thr Glu Glu Asn Phe Ile Arg Glu His
            180                 185                 190

Met Ser Ser Lys Thr Val Glu Val Trp Met Gly Leu Asn Gln Leu Asp
        195                 200                 205

Glu His Ala Gly Trp Gln Trp Ser Asp Gly Thr Pro Leu Asn Tyr Leu
    210                 215                 220

Asn Trp Ser Pro Glu Val Asn Phe Glu Pro Phe Val Glu Asp His Cys
225                 230                 235                 240

Gly Thr Phe Ser Ser Phe Met Pro Ser Ala Trp Arg Ser Arg Asp Cys
                245                 250                 255

Glu Ser Thr Leu Pro Tyr Ile Cys Lys Lys Tyr Leu Asn His Ile Asp
            260                 265                 270

His Glu Ile Val Glu Val Asn Thr Ser Asp Met Tyr Pro Met Pro Asn
        275                 280                 285

Thr Leu Glu Tyr Gly Asn Arg Thr Tyr Lys Ile Ile Asn Ala Asn Met
    290                 295                 300

Thr Trp Tyr Ala Ala Ile Lys Thr Cys Leu Met His Lys Ala Gln Leu
305                 310                 315                 320

Val Ser Ile Thr Asp Gln Tyr His Gln Ser Phe Leu Thr Val Val Leu
                325                 330                 335

Asn Arg Leu Gly Tyr Ala His Trp Ile Gly Leu Phe Thr Thr Asp Asn
            340                 345                 350

Gly Leu Asn Phe Asp Trp Ser Asp Gly Thr Lys Ser Ser Phe Thr Phe
        355                 360                 365

Trp Lys Asp Glu Glu Ser Ser Leu Leu Gly Asp Cys Val Phe Ala Asp
    370                 375                 380

Ser Asn Gly Arg Trp His Ser Thr Ala Cys Glu Ser Phe Leu Gln Gly
385                 390                 395                 400

Ala Ile Cys His Val Pro Pro Glu Thr Arg Gln Ser Glu His Pro Glu
                405                 410                 415

Leu


<210> SEQ ID NO 60
<211> LENGTH: 387
<212> TYPE: DNA
<213> ORGANISM: Artificial Sequence
<220> FEATURE:
<223> OTHER INFORMATION: CysR

<400> SEQUENCE: 60

aagggcatct tcgtgatcca gagcgagagc ctgaagaagt gcatccaggc cggcaagagc      60

gtgctgaccc tggaaaattg caagcaggcc aacaagcaca tgctgtggaa atgggtgtcc     120

aaccacggcc tgttcaacat cggcggctct ggatgtctgg gcctgaattt ctctgcccct     180

gagcagcctc tgagcctgta cgagtgtgat agcaccctgg tgtccctgag atggcggtgc     240

aaccggaaga tgatcacagg ccctctgcag tactctgtgc aggtcgccca cgacaatacc     300

gtggtggcca gcagaaagta catccacaag tggatcagct acggcagcgg cggaggcgac     360
```

-continued

```
atctgtgaat acctgcacaa ggatctg                                        387


<210> SEQ ID NO 61
<211> LENGTH: 129
<212> TYPE: PRT
<213> ORGANISM: Artificial Sequence
<220> FEATURE:
<223> OTHER INFORMATION: CysR

<400> SEQUENCE: 61

Lys Gly Ile Phe Val Ile Gln Ser Glu Ser Leu Lys Lys Cys Ile Gln
1               5                   10                  15

Ala Gly Lys Ser Val Leu Thr Leu Glu Asn Cys Lys Gln Ala Asn Lys
            20                  25                  30

His Met Leu Trp Lys Trp Val Ser Asn His Gly Leu Phe Asn Ile Gly
        35                  40                  45

Gly Ser Gly Cys Leu Gly Leu Asn Phe Ser Ala Pro Glu Gln Pro Leu
    50                  55                  60

Ser Leu Tyr Glu Cys Asp Ser Thr Leu Val Ser Leu Arg Trp Arg Cys
65                  70                  75                  80

Asn Arg Lys Met Ile Thr Gly Pro Leu Gln Tyr Ser Val Gln Val Ala
                85                  90                  95

His Asp Asn Thr Val Val Ala Ser Arg Lys Tyr Ile His Lys Trp Ile
            100                 105                 110

Ser Tyr Gly Ser Gly Gly Gly Asp Ile Cys Glu Tyr Leu His Lys Asp
        115                 120                 125

Leu


<210> SEQ ID NO 62
<211> LENGTH: 1026
<212> TYPE: DNA
<213> ORGANISM: Artificial Sequence
<220> FEATURE:
<223> OTHER INFORMATION: CysR-FNII-CTLD1

<400> SEQUENCE: 62

aagggcatct tcgtgatcca gagcgagagc ctgaagaagt gcatccaggc cggcaagagc     60

gtgctgaccc tggaaaattg caagcaggcc aacaagcaca tgctgtggaa atgggtgtcc    120

aaccacggcc tgttcaacat cggcggctct ggatgtctgg gcctgaattt ctctgcccct    180

gagcagcctc tgagcctgta cgagtgtgat agcaccctgg tgtccctgag atggcggtgc    240

aaccggaaga tgatcacagg ccctctgcag tactctgtgc aggtcgccca cgacaatacc    300

gtggtggcca gcagaaagta catccacaag tggatcagct acggcagcgg cggaggcgac    360

atctgtgaat acctgcacaa ggatctgcac accatcaagg gcaacaccca cggaatgccc    420

tgcatgttcc cgtttcagta caaccaccag tggcaccacg agtgcaccag agaaggcaga    480

gaggacgacc tgctttggtg cgccacaacc agcagatacg agcgggatga gaagtggggc    540

ttctgccctg atcctacctc tgccgaagtg ggctgcgata ccatctggga gaaagacctg    600

aacagccaca tctgctacca gttcaacctg ctgtccagcc tgtcttggag cgaggcccac    660

agcagctgtc aaatgcaagg cggcacactg ctgagcatca ccgacgagac agaggaaaac    720

ttcatccgcg agcacatgag cagcaagacc gtggaagtgt ggatgggact gaaccagctg    780

gatgagcatg ccggatggca gtggagtgat ggcacccctc tgaactacct gaactggtcc    840

cctgaagtga acttcgagcc cttcgtggaa gatcactgcg gcaccttcag cagcttcatg    900

cccagcgctt ggagaagcag agactgcgag agcaccctgc cttacatctg caagaagtac    960
```

ctgaaccaca tcgaccacga gatcgtggaa aaggacgcct ggaagtacta cgccacacac 1020
tgcgag 1026

<210> SEQ ID NO 63
<211> LENGTH: 342
<212> TYPE: PRT
<213> ORGANISM: Artificial Sequence
<220> FEATURE:
<223> OTHER INFORMATION: CysR-FNII-CTLD1

<400> SEQUENCE: 63

```
Lys Gly Ile Phe Val Ile Gln Ser Glu Ser Leu Lys Lys Cys Ile Gln
1               5                   10                  15

Ala Gly Lys Ser Val Leu Thr Leu Glu Asn Cys Lys Gln Ala Asn Lys
            20                  25                  30

His Met Leu Trp Lys Trp Val Ser Asn His Gly Leu Phe Asn Ile Gly
        35                  40                  45

Gly Ser Gly Cys Leu Gly Leu Asn Phe Ser Ala Pro Glu Gln Pro Leu
    50                  55                  60

Ser Leu Tyr Glu Cys Asp Ser Thr Leu Val Ser Leu Arg Trp Arg Cys
65                  70                  75                  80

Asn Arg Lys Met Ile Thr Gly Pro Leu Gln Tyr Ser Val Gln Val Ala
                85                  90                  95

His Asp Asn Thr Val Val Ala Ser Arg Lys Tyr Ile His Lys Trp Ile
            100                 105                 110

Ser Tyr Gly Ser Gly Gly Gly Asp Ile Cys Glu Tyr Leu His Lys Asp
        115                 120                 125

Leu His Thr Ile Lys Gly Asn Thr His Gly Met Pro Cys Met Phe Pro
    130                 135                 140

Phe Gln Tyr Asn His Gln Trp His His Glu Cys Thr Arg Glu Gly Arg
145                 150                 155                 160

Glu Asp Asp Leu Leu Trp Cys Ala Thr Thr Ser Arg Tyr Glu Arg Asp
                165                 170                 175

Glu Lys Trp Gly Phe Cys Pro Asp Pro Thr Ser Ala Glu Val Gly Cys
            180                 185                 190

Asp Thr Ile Trp Glu Lys Asp Leu Asn Ser His Ile Cys Tyr Gln Phe
        195                 200                 205

Asn Leu Leu Ser Ser Leu Ser Trp Ser Glu Ala His Ser Ser Cys Gln
    210                 215                 220

Met Gln Gly Gly Thr Leu Leu Ser Ile Thr Asp Glu Thr Glu Glu Asn
225                 230                 235                 240

Phe Ile Arg Glu His Met Ser Ser Lys Thr Val Glu Val Trp Met Gly
                245                 250                 255

Leu Asn Gln Leu Asp Glu His Ala Gly Trp Gln Trp Ser Asp Gly Thr
            260                 265                 270

Pro Leu Asn Tyr Leu Asn Trp Ser Pro Glu Val Asn Phe Glu Pro Phe
        275                 280                 285

Val Glu Asp His Cys Gly Thr Phe Ser Ser Phe Met Pro Ser Ala Trp
    290                 295                 300

Arg Ser Arg Asp Cys Glu Ser Thr Leu Pro Tyr Ile Cys Lys Lys Tyr
305                 310                 315                 320

Leu Asn His Ile Asp His Glu Ile Val Glu Lys Asp Ala Trp Lys Tyr
                325                 330                 335

Tyr Ala Thr His Cys Glu
```

340

<210> SEQ ID NO 64
<211> LENGTH: 165
<212> TYPE: DNA
<213> ORGANISM: Artificial Sequence
<220> FEATURE:
<223> OTHER INFORMATION: CD8 alpha hinge domain

<400> SEQUENCE: 64
ttcgtgccgg tcttcctgcc agcgaagcca accacgacgc cagcaccgcg accaccaaca 60
cctgcgccca ccatcgcgtc gcagcccctg tccctgcgcc cagaggcgtg cagaccagca 120
gcgggggcgg cagtgcacac gagggggctg gacttcgcct gtgat 165

<210> SEQ ID NO 65
<211> LENGTH: 60
<212> TYPE: DNA
<213> ORGANISM: Artificial Sequence
<220> FEATURE:
<223> OTHER INFORMATION: PLA2R Signal peptide

<400> SEQUENCE: 65
atgctgctga gccctagcct gctgctgctc ctgcttcttg gagcccctag aggatgtgcc 60

<210> SEQ ID NO 66
<211> LENGTH: 126
<212> TYPE: DNA
<213> ORGANISM: Artificial Sequence
<220> FEATURE:
<223> OTHER INFORMATION: 4-1BB intracellular domain

<400> SEQUENCE: 66
aagcgcggtc gcaagaaact gctctatatt tttaaacagc cattcatgag acctgtccag 60
accactcaag aggaggacgg atgttcctgt agatttcctg aagaggaaga ggggggggtgc 120 gagctg 126

<210> SEQ ID NO 67
<211> LENGTH: 57
<212> TYPE: DNA
<213> ORGANISM: Artificial Sequence
<220> FEATURE:
<223> OTHER INFORMATION: PLA2R pro-peptide

<400> SEQUENCE: 67
ggatctgaag gtgttgccgc cgctctgaca cccgagagac tgctggaatg gcaggac 57

<210> SEQ ID NO 68
<211> LENGTH: 30
<212> TYPE: DNA
<213> ORGANISM: Artificial Sequence
<220> FEATURE:
<223> OTHER INFORMATION: GS linker

<400> SEQUENCE: 68
ggtggcggag gttctggagg tggaggttcc 30

<210> SEQ ID NO 69
<211> LENGTH: 10
<212> TYPE: DNA
<213> ORGANISM: Artificial Sequence
<220> FEATURE:
<223> OTHER INFORMATION: GS linker

<400> SEQUENCE: 69 gggsggggs 10

<210> SEQ ID NO 70
<211> LENGTH: 479
<212> TYPE: PRT
<213> ORGANISM: Artificial Sequence
<220> FEATURE:
<223> OTHER INFORMATION: Extracellular domains of Construct 4027.CF12

<400> SEQUENCE: 70

Lys Gly Ile Phe Val Ile Gln Ser Glu Ser Leu Lys Lys Cys Ile Gln
1 5 10 15

Ala Gly Lys Ser Val Leu Thr Leu Glu Asn Cys Lys Gln Ala Asn Lys
20 25 30

His Met Leu Trp Lys Trp Val Ser Asn His Gly Leu Phe Asn Ile Gly
35 40 45

Gly Ser Gly Cys Leu Gly Leu Asn Phe Ser Ala Pro Glu Gln Pro Leu
50 55 60

Ser Leu Tyr Glu Cys Asp Ser Thr Leu Val Ser Leu Arg Trp Arg Cys
65 70 75 80

Asn Arg Lys Met Ile Thr Gly Pro Leu Gln Tyr Ser Val Gln Val Ala
85 90 95

His Asp Asn Thr Val Val Ala Ser Arg Lys Tyr Ile His Lys Trp Ile
100 105 110

Ser Tyr Gly Ser Gly Gly Gly Asp Ile Cys Glu Tyr Leu His Lys Asp
115 120 125

Leu His Thr Ile Lys Gly Asn Thr His Gly Met Pro Cys Met Phe Pro
130 135 140

Phe Gln Tyr Asn His Gln Trp His His Glu Cys Thr Arg Glu Gly Arg
145 150 155 160

Glu Asp Asp Leu Leu Trp Cys Ala Thr Thr Ser Arg Tyr Glu Arg Asp
165 170 175

Glu Lys Trp Gly Phe Cys Pro Asp Pro Thr Ser Ala Glu Val Gly Cys
180 185 190

Asp Thr Ile Trp Glu Lys Asp Leu Asn Ser His Ile Cys Tyr Gln Phe
195 200 205

Asn Leu Leu Ser Ser Leu Ser Trp Ser Glu Ala His Ser Ser Cys Gln
210 215 220

Met Gln Gly Gly Thr Leu Leu Ser Ile Thr Asp Glu Thr Glu Glu Asn
225 230 235 240

Phe Ile Arg Glu His Met Ser Ser Lys Thr Val Glu Val Trp Met Gly
245 250 255

Leu Asn Gln Leu Asp Glu His Ala Gly Trp Gln Trp Ser Asp Gly Thr
260 265 270

Pro Leu Asn Tyr Leu Asn Trp Ser Pro Glu Val Asn Phe Glu Pro Phe
275 280 285

Val Glu Asp His Cys Gly Thr Phe Ser Ser Phe Met Pro Ser Ala Trp
290 295 300

Arg Ser Arg Asp Cys Glu Ser Thr Leu Pro Tyr Ile Cys Lys Lys Tyr
305 310 315 320

Leu Asn His Ile Asp His Glu Ile Val Glu Lys Asp Ala Trp Lys Tyr
325 330 335

Tyr Ala Thr His Cys Glu Pro Gly Trp Asn Pro Tyr Asn Arg Asn Cys
340 345 350

```
Tyr Lys Leu Gln Lys Glu Glu Lys Thr Trp His Glu Ala Leu Arg Ser
        355                 360                 365

Cys Gln Ala Asp Asn Ser Ala Leu Ile Asp Ile Thr Ser Leu Ala Glu
    370                 375                 380

Val Glu Phe Leu Val Thr Leu Leu Gly Asp Glu Asn Ala Ser Glu Thr
385                 390                 395                 400

Trp Ile Gly Leu Ser Ser Asn Lys Ile Pro Val Ser Phe Glu Trp Ser
                405                 410                 415

Asn Asp Ser Ser Val Ile Phe Thr Asn Trp His Thr Leu Glu Pro His
            420                 425                 430

Ile Phe Pro Asn Arg Ser Gln Leu Cys Val Ser Ala Glu Gln Ser Glu
        435                 440                 445

Gly His Trp Lys Val Lys Asn Cys Glu Glu Arg Leu Phe Tyr Ile Cys
    450                 455                 460

Lys Lys Ala Gly His Val Leu Ser Asp Ala Glu Ser Gly Cys Gln
465                 470                 475


<210> SEQ ID NO 71
<211> LENGTH: 629
<212> TYPE: PRT
<213> ORGANISM: Artificial Sequence
<220> FEATURE:
<223> OTHER INFORMATION: Extracellular domains of Construct 4028.CF123

<400> SEQUENCE: 71

Lys Gly Ile Phe Val Ile Gln Ser Glu Ser Leu Lys Lys Cys Ile Gln
1               5                   10                  15

Ala Gly Lys Ser Val Leu Thr Leu Glu Asn Cys Lys Gln Ala Asn Lys
            20                  25                  30

His Met Leu Trp Lys Trp Val Ser Asn His Gly Leu Phe Asn Ile Gly
        35                  40                  45

Gly Ser Gly Cys Leu Gly Leu Asn Phe Ser Ala Pro Glu Gln Pro Leu
    50                  55                  60

Ser Leu Tyr Glu Cys Asp Ser Thr Leu Val Ser Leu Arg Trp Arg Cys
65                  70                  75                  80

Asn Arg Lys Met Ile Thr Gly Pro Leu Gln Tyr Ser Val Gln Val Ala
                85                  90                  95

His Asp Asn Thr Val Val Ala Ser Arg Lys Tyr Ile His Lys Trp Ile
            100                 105                 110

Ser Tyr Gly Ser Gly Gly Gly Asp Ile Cys Glu Tyr Leu His Lys Asp
        115                 120                 125

Leu His Thr Ile Lys Gly Asn Thr His Gly Met Pro Cys Met Phe Pro
    130                 135                 140

Phe Gln Tyr Asn His Gln Trp His His Glu Cys Thr Arg Glu Gly Arg
145                 150                 155                 160

Glu Asp Asp Leu Leu Trp Cys Ala Thr Thr Ser Arg Tyr Glu Arg Asp
                165                 170                 175

Glu Lys Trp Gly Phe Cys Pro Asp Pro Thr Ser Ala Glu Val Gly Cys
            180                 185                 190

Asp Thr Ile Trp Glu Lys Asp Leu Asn Ser His Ile Cys Tyr Gln Phe
        195                 200                 205

Asn Leu Leu Ser Ser Leu Ser Trp Ser Glu Ala His Ser Ser Cys Gln
    210                 215                 220

Met Gln Gly Gly Thr Leu Leu Ser Ile Thr Asp Glu Thr Glu Glu Asn
225                 230                 235                 240
```

-continued

```
Phe Ile Arg Glu His Met Ser Ser Lys Thr Val Glu Val Trp Met Gly
                245                 250                 255

Leu Asn Gln Leu Asp Glu His Ala Gly Trp Gln Trp Ser Asp Gly Thr
            260                 265                 270

Pro Leu Asn Tyr Leu Asn Trp Ser Pro Glu Val Asn Phe Glu Pro Phe
        275                 280                 285

Val Glu Asp His Cys Gly Thr Phe Ser Ser Phe Met Pro Ser Ala Trp
    290                 295                 300

Arg Ser Arg Asp Cys Glu Ser Thr Leu Pro Tyr Ile Cys Lys Lys Tyr
305                 310                 315                 320

Leu Asn His Ile Asp His Glu Ile Val Glu Lys Asp Ala Trp Lys Tyr
                325                 330                 335

Tyr Ala Thr His Cys Glu Pro Gly Trp Asn Pro Tyr Asn Arg Asn Cys
            340                 345                 350

Tyr Lys Leu Gln Lys Glu Glu Lys Thr Trp His Glu Ala Leu Arg Ser
        355                 360                 365

Cys Gln Ala Asp Asn Ser Ala Leu Ile Asp Ile Thr Ser Leu Ala Glu
    370                 375                 380

Val Glu Phe Leu Val Thr Leu Leu Gly Asp Glu Asn Ala Ser Glu Thr
385                 390                 395                 400

Trp Ile Gly Leu Ser Ser Asn Lys Ile Pro Val Ser Phe Glu Trp Ser
                405                 410                 415

Asn Asp Ser Ser Val Ile Phe Thr Asn Trp His Thr Leu Glu Pro His
            420                 425                 430

Ile Phe Pro Asn Arg Ser Gln Leu Cys Val Ser Ala Glu Gln Ser Glu
        435                 440                 445

Gly His Trp Lys Val Lys Asn Cys Glu Glu Arg Leu Phe Tyr Ile Cys
    450                 455                 460

Lys Lys Ala Gly His Val Leu Ser Asp Ala Glu Ser Gly Cys Gln Glu
465                 470                 475                 480

Gly Trp Glu Arg His Gly Gly Phe Cys Tyr Lys Ile Asp Thr Val Leu
                485                 490                 495

Arg Ser Phe Asp Gln Ala Ser Ser Gly Tyr Tyr Cys Pro Pro Ala Leu
            500                 505                 510

Val Thr Ile Thr Asn Arg Phe Glu Gln Ala Phe Ile Thr Ser Leu Ile
        515                 520                 525

Ser Ser Val Val Lys Met Lys Asp Ser Tyr Phe Trp Ile Ala Leu Gln
    530                 535                 540

Asp Gln Asn Asp Thr Gly Glu Tyr Thr Trp Lys Pro Val Gly Gln Lys
545                 550                 555                 560

Pro Glu Pro Val Gln Tyr Thr His Trp Asn Thr His Gln Pro Arg Tyr
                565                 570                 575

Ser Gly Gly Cys Val Ala Met Arg Gly Arg His Pro Leu Gly Arg Trp
            580                 585                 590

Glu Val Lys His Cys Arg His Phe Lys Ala Met Ser Leu Cys Lys Gln
        595                 600                 605

Pro Val Glu Asn Gln Glu Lys Ala Glu Tyr Glu Glu Arg Trp Pro Phe
    610                 615                 620

His Pro Cys Tyr Leu
625
```

<210> SEQ ID NO 72
<211> LENGTH: 336
<212> TYPE: DNA

-continued

```
<213> ORGANISM: Artificial Sequence
<220> FEATURE:
<223> OTHER INFORMATION: CD3zeta intracellular domain

<400> SEQUENCE: 72

agagtgaagt tcagcaggag cgcagacgcc cccgcgtaca agcagggcca gaaccagctc     60

tataacgagc tcaatctagg acgaagagag gagtacgatg ttttggacaa gagacgtggc    120

cgggaccctg agatgggggg aaagccgaga aggaagaacc ctcaggaagg cctgtacaat    180

gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgc                              336
```

COMPOSITIONS AND METHODS OF PHOSPHOLIPASE A2 RECEPTOR CHIMERIC AUTOANTIBODY RECEPTOR T CELLS

CROSS-REFERENCE TO RELATED APPLICATION

The present application is a continuation of Ser. No. 17/051,248, filed Oct. 28, 2020, a 35 U.S.C. § 371 national phase application from, and claims priority to, International Application No. PCT/US2019/030459, filed May 2, 2019, and published under PCT Article 21(2) in English, which is entitled to priority under 35 U.S.C. § 119(e) to U.S. Provisional Patent Application No. 62/665,863 filed May 2, 2018, which is hereby incorporated by reference in its entirety herein.

BACKGROUND OF THE INVENTION

Membranous nephropathy (MN) is among the most common primary causes of nephrotic syndrome in adults (up to one-third of cases). About 15-25% of membranous nephropathy cases are secondary membranous nephropathy, caused by drugs, infections, tumors, or immune diseases. The remaining 75-85% of membranous nephropathy cases are idiopathic, also called primary membranous nephropathy. MN is caused by immune complex formation in the glomerulus. The immune complexes are formed by binding of antibodies to antigens on the podocyte. The immune complex serves as an activator that triggers complement-mediated lysis of glomerular epithelial cells and the release of proteases and oxidants damaging capillary walls. Up to 40% of patients with primary membranous nephropathy who do not receive immunosuppressive treatment develop end-stage renal disease requiring dialysis or kidney transplantation.

The M-type phospholipase A2 receptor (PLA2R) has been described as a major autoantigen in primary membranous nephropathy. Autoantibodies to PLA2R are present in 70-80% of cases of primary membranous nephropathy, and can be used for the diagnosis and monitoring of treatment of primary membranous nephropathy both in the native kidneys and after kidney transplant.

Current guidelines suggest treatment with alkylating agents or calcineurin inhibitors as first-line therapy for the treatment of severe, primary membranous nephropathy. Rituximab, an anti-CD20 antibody, has also shown promise and is being evaluated for treating MN. However, since these treatments lack specificity for the autoreactive B cells that produce the serum anti-PLA2R antibody, they can be associated with risk of life-threatening infections. Moreover, relapse can occur in patients who achieve remission in proteinuria, and disease can recur after kidney transplantation. Importantly, relapse is usually associated with recurrence in detectable anti-PLA2R autoantibody, thus further supporting the role of this antibody in disease pathogenesis.

There is an urgent need in the art for achieving a more specific and effective treatment for primary membranous nephropathy. This invention addresses this need.

SUMMARY OF THE INVENTION

In one aspect, the invention includes a polynucleotide encoding a chimeric autoantibody receptor (CAAR), wherein the CAAR comprises a phospholipase A2 receptor (PLA2R) autoantigen or fragment thereof, and optionally, a transmembrane domain, an intracellular domain of a costimulatory molecule, and/or a signaling domain.

In another aspect, the invention includes a vector comprising any one of the polynucleotides disclosed herein.

In yet another aspect, the invention includes a chimeric autoantibody receptor (CAAR) comprising an extracellular domain comprising a phospholipase A2 receptor (PLA2R) autoantigen or fragment thereof.

In still another aspect, the invention includes a chimeric autoantibody receptor (CAAR) comprising an extracellular domain comprising a phospholipase A2 receptor (PLA2R) autoantigen or fragment thereof, and optionally, a transmembrane domain, an intracellular domain of a costimulatory molecule, and/or a signaling domain.

Another aspect of the invention includes a genetically modified cell comprising any one of the CAARs disclosed herein.

Yet another aspect of the invention includes genetically modified cell comprising: (a) a chimeric autoantibody receptor (CAAR) comprising an extracellular domain comprising a phospholipase A2 receptor (PLA2R) autoantigen or fragment thereof, a killer immunoglobulin-like receptor (KIR) transmembrane domain and a KIR cytoplasmic domain; and (b) DAP12.

Still another aspect of the invention includes a pharmaceutical composition comprising any one of the polynucleotides disclosed herein, any one of the CAARs disclosed herein or any one of the cells disclosed herein, and a pharmaceutically acceptable excipient.

In another aspect, the invention includes a method for treating an autoantibody-mediated kidney disease in a subject. The method comprises administering to the subject an effective amount of a genetically modified T cell comprising a polynucleotide encoding a chimeric autoantibody receptor (CAAR), wherein the polynucleotide encodes a phospholipase A2 receptor (PLA2R) autoantigen or fragment thereof, and optionally, a transmembrane domain, an intracellular domain of a costimulatory molecule, and/or a signaling domain, thereby treating the autoantibody mediated kidney disease in the subject.

In yet another aspect, the invention includes a method for preventing or reducing glomerulus damage in a subject at risk of or suffering from an autoantibody-mediated kidney disease, the method comprising: administering to the subject an effective amount of a genetically modified T cell comprising a polynucleotide encoding a chimeric autoantibody receptor (CAAR), wherein the polynucleotide encodes a phospholipase A2 receptor (PLA2R) autoantigen or fragment thereof, and optionally a transmembrane domain, an intracellular domain of a costimulatory molecule, and/or a signaling domain, thereby preventing or reducing glomerulus damage in the subject.

In still another aspect, the invention includes a method for treating an autoantibody-mediated kidney disease in a subject. The method comprises administering to the subject an effective amount of a genetically modified T cell comprising: (a) a polynucleotide encoding a chimeric autoantibody receptor (CAAR) comprising an extracellular domain comprising phospholipase A2 receptor (PLA2R) autoantigen or fragment thereof, a killer immunoglobulin-like receptor (KIR) transmembrane domain and a KIR cytoplasmic domain; and (b) a polynucleotide encoding DAP12, thereby treating the autoantibody-mediated kidney disease in the subject.

In another aspect, the invention includes a method for preventing or reducing glomerulus damage in a subject at risk of or suffering from an autoantibody-mediated kidney disease The method comprises administering to the subject an effective amount of a genetically modified T cell comprising: (a) a polynucleotide encoding a chimeric autoantibody receptor (CAAR) comprising an extracellular domain comprising phospholipase A2 receptor (PLA2R) autoantigen or fragment thereof, a killer immunoglobulin-like receptor (KIR) transmembrane domain and a KIR cytoplasmic domain; and (b) a polynucleotide encoding DAP12, thereby preventing or reducing glomerulus damage in the subject.

In various embodiments of the above aspects or any other aspect of the invention delineated herein, the PLA2R autoantigen or fragment thereof is selected from the group consisting of: (a) an extracellular domain comprising a CysR or ricin B type lectin domain, a fibronectin type II domain, a C-type lectin domain 1 and a C-type lectin domain 2; and (b) an extracellular domain comprising a CysR or ricin B type lectin domain, a fibronectin type II domain, a C-type lectin domain 1, a C-type lectin domain 2 and a C-type lectin domain 3.

In certain embodiments, the PLA2R autoantigen or fragment thereof is selected from the group consisting of: (a) an extracellular domain comprising a cysteine rich domain, (b) an extracellular domain comprising a cysteine rich domain, a fibronectin type II domain, and a C-type lectin domain 1, (c) an extracellular domain comprising a cysteine rich domain, a fibronectin type II domain, a C-type lectin domain 1, a C-type lectin domain 2, and a C-type lectin domain 3, (d) an extracellular domain comprising a cysteine rich domain, a fibronectin type II domain, a C-type lectin domain 1, a C-type lectin domain 2, a C-type lectin domain 3, and a C-type lectin domain 7, (e) an extracellular domain comprising a cysteine rich domain, a fibronectin type II domain, a C-type lectin domain 1, and a C-type lectin domain 7, or (f) an extracellular domain comprising a cysteine rich domain, a C-type lectin domain 1, and a C-type lectin domain 7.

In certain embodiments, the PLA2R extracellular domain is encoded by a nucleic acid sequence comprising SEQ ID NO: 8 or SEQ ID NO: 15 or SEQ ID NO: 47 or SEQ ID NO: 60 or SEQ ID NO: 50 or SEQ ID NO: 62 or SEQ ID NO: 52 or SEQ ID NO: 54 or SEQ ID NO: 56 or SEQ ID NO: 58.

In certain embodiments, the transmembrane domain comprises a CD8 alpha chain transmembrane domain. In certain embodiments, the CD8 alpha chain transmembrane domain is encoded by a nucleic acid sequence comprising SEQ ID NO: 20. In certain embodiments, the CD8 alpha chain transmembrane domain comprises the amino acid sequence of SEQ ID NO: 19.

In certain embodiments, the CAAR further comprises a hinge domain. In certain embodiments, the hinge domain is encoded by a nucleic acid sequence comprising SEQ ID NO: 10 or SEQ ID NO: 42 or SEQ ID NO: 64. In certain embodiments, the hinge domain comprises the amino acid sequence of SEQ ID NO: SEQ ID NO: 43 or SEQ ID NO: 44.

In certain embodiments, the CAAR further comprises a GS linker. In certain embodiments, the GS linker is encoded by a nucleic acid sequence comprising SEQ ID NO: 68. In certain embodiments, the GS linker comprises SEQ ID NO: 69.

In certain embodiments, the intracellular domain of a costimulatory molecule comprises 4-1BB. In certain embodiments, the 4-1BB intracellular domain is encoded by a nucleic acid sequence comprising SEQ ID NO: 22 or SEQ ID NO: 66. In certain embodiments, the 4-1BB intracellular domain comprises the amino acid sequence of SEQ ID NO: 21.

In certain embodiments, the signaling domain comprises a CD3 zeta signaling domain. In certain embodiments, the CD3 zeta signaling domain is encoded by a nucleic acid sequence comprising SEQ ID NO: 24 or SEQ ID NO: 72. In certain embodiments, the CD3 zeta signaling domain comprises an amino acid sequence of SEQ ID NO: 23 or SEQ ID NO: 45.

In certain embodiments, the CAAR is encoded by a nucleic acid sequence selected from the group consisting of SEQ ID NOs: 11, 17, 25, 27, 29, 31, 33, 35, 37, and 39. In certain embodiments, the CAAR comprises an amino acid sequence selected from the group consisting of SEQ ID NOs: 12, 18, 26, 28, 30, 32, 34, 36, 38, and 40.

In certain embodiments, the CAAR comprises a phospholipase A2 receptor (PLA2R) autoantigen or fragment thereof, a killer immunoglobulin-like receptor (KIR) transmembrane domain and a KIR cytoplasmic domain.

In certain embodiments, the vector is a lentiviral vector. In certain embodiments, the vector is a RNA vector.

In certain embodiments, the cell expresses the CAAR and has high affinity to autoantibody-based BCRs on B cells. In certain embodiments, the cell expresses the CAAR and induces killing of B cells expressing autoantibodies. In certain embodiments, the cell expresses the CAAR and has limited toxicity toward healthy cells.

In certain embodiments, the cell is selected from the group consisting of a helper T cell, a cytotoxic T cell, a memory T cell, regulatory T cell, gamma delta T cell, a natural killer cell, a cytokine induced killer cell, a cell line thereof, a T memory stem cell, a T cell derived from a pluripotent stem and other effector cell.

In certain embodiments, the autoantibody mediated kidney disease is selected from the group consisting of a glomerular disease and a primary membranous nephropathy.

In certain embodiments, the subject is a human.

In certain embodiments, the modified T cell targets B cells.

In certain embodiments, the KIR is KIRS2 or KIR2DS2.

In certain embodiments, the vector comprises an inducible promoter operably linked to the polynucleotide encoding the CAAR.

In certain embodiments, the cell comprises a polynucleotide encoding the CAAR operably linked to an inducible promoter.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A depicts construct 4025.C (or construct C), whose extracellular domain consists of the PLA2R CysR domain, followed by a CD8 hinge domain. FIG. 2B depicts construct 4026.CF1 (or construct CF1), consisting of the CysR, FNII, and CTLD1 domains followed by a CD8 hinge domain. FIG. 2C depicts construct 4027.CF12, consisting of the CysR, FNII, CTLD1, and CTLD2 domains, followed by a CD8 hinge domain. FIG. 2D depicts construct 4028.CF123 (or construct CF123), consisting of the CysR, FNII, CTLD1, CTLD2, and CTLD3 domains, followed by either a CD8 hinge (4028.CF123) or GS linker (CF123). FIG. 2E depicts construct CF1237, consisting of the CysR, FNII, CTLD1, CTLD2, CTLD3, and CTLD7 domains followed by a GS linker. FIG. 2F depicts construct CF17, consisting of the CysR, FNII, CTLD1, and CTLD7 domains, followed by a GS linker. FIG. 2G depicts construct C17, consisting of the CysR, CTLD1, and CTLD7 domains, followed by a GS linker.

FIG. 3A is an illustration showing a portion of the plasmid map comprising the 4028.CF123 CAAR. FIG. 3B is a table distinguishing the compositions of the CAAR constructs described in this invention.

FIG. 9 is a set of graphs illustrating that plate-bound MN patient IgG stimulates IFN-γ secretion from PLA2R CAAR-transduced primary human T cells. $5\times10^4$ primary human T cells were cultured for 24 h in a 96-well plate coated with 10 μg/ml of either MN patient IgG or control human IgG. Culture supernatants were then harvested for detection of IFN-γ by ELISA. IFNγ production was detectable in all culture supernatants and was elevated relative to untransduced T cells, or PLA2R CAAR T cells stimulated with control (Ctrl) human IgG.

DETAILED DESCRIPTION

Figure 1:
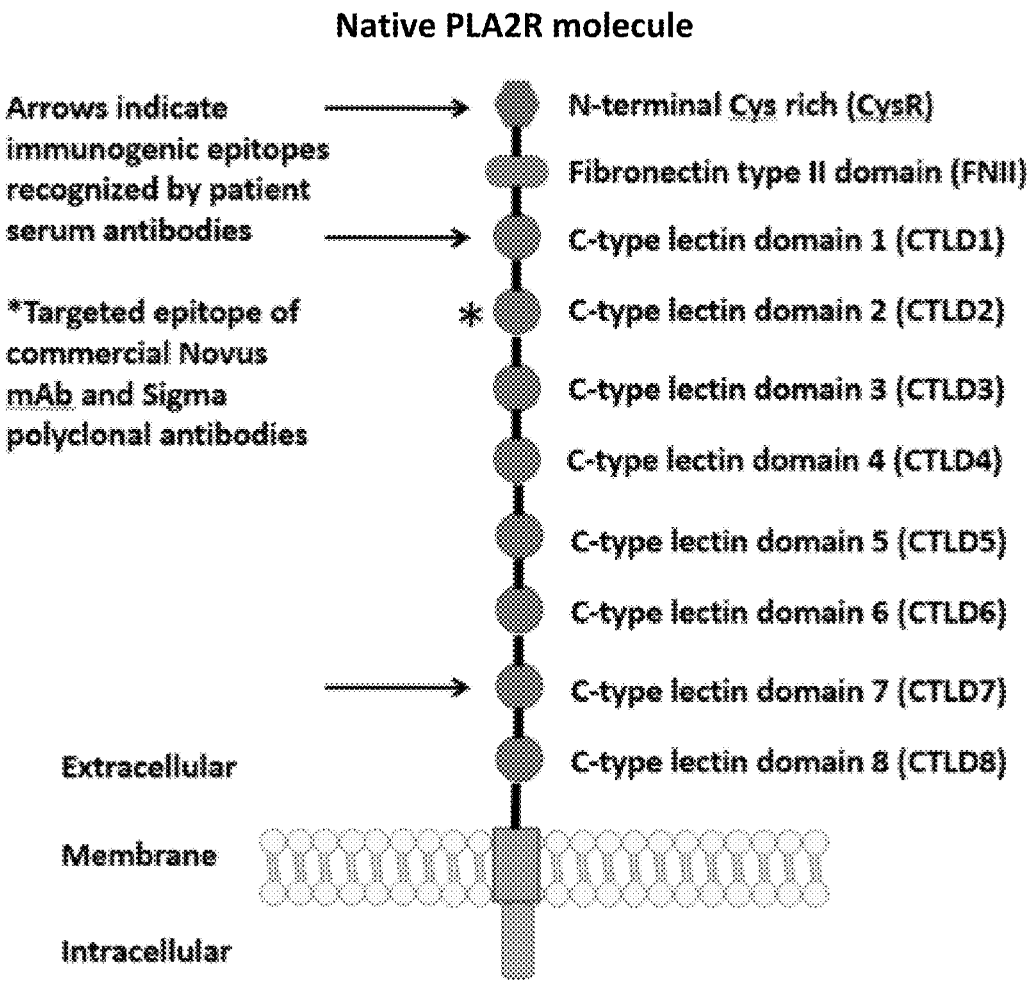
FIG. 1 is an illustration showing a schematic of the native PLA2R molecule. The N terminal cysteine-rich (CysR) domain (Ricin B type lectin domain) is the immunodominant epitope that is recognized by patient serum antibodies. In non-reducing conditions, serum antibody recognition has been reported to be dependent on the first 3 C-type lectin domains (CTLD). In addition to the cysteine-rich domain, serum antibody immunoreactivity to the C-type lectin domains 1 and 7 has also been reported. A commercial Novus monoclonal antibody (mAb) and polyclonal Sigma antibody bind to the CTLD2 domain.

The invention includes a chimeric autoantibody receptor (CAAR) specific for anti-phospholipase A2 receptor (PLA2R) B cell receptor (BCR), compositions comprising the CAAR, polynucleotides encoding the CAAR, vectors comprising a polynucleotide encoding the CAAR, and recombinant T cells comprising the CAAR. The invention also includes methods of making a genetically modified cell, e.g., a genetically modified T cell, expressing a PLA2R-CAAR wherein the expressed CAAR comprises a PLA2R extracellular domain.

The present invention also relates generally to the use of cells, e.g., T cells, engineered to express a CAAR to treat an autoantibody-mediated kidney disease associated with targeting of self-antigens (e.g. PLA2R). In one embodiment, the cells, e.g., T cells expressing the CAAR of the invention specifically bind to and kill anti-PLA2R BCR-expressing cells, but do not bind to and kill normal BCR-expressing cells.

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About," as used herein, when referring to a measurable value such as an amount, a temporal duration, and the like, is meant to encompass variations of ±20% or ±10%, in some instances ±5%, in some instances ±1%, and in some instance ±0.1% from the specified value, as such variations are appropriate to perform the disclosed methods.

The term "antibody," as used herein, refers to an immunoglobulin molecule that binds with an antigen. Antibodies can be intact immunoglobulins derived from natural sources or from recombinant sources and can be immunoreactive portions of intact immunoglobulins. Antibodies are typically tetramers of immunoglobulin molecules. The antibody in the present invention may exist in a variety of forms where the antibody is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "high affinity," as used herein, refers to high specificity in binding or interacting or attraction of a binding molecule to a target molecule. For example, in some embodiments, the binding molecule may have an affinity for the target molecule stronger than 100 nM, 50 nM, 20 nM, 15 nM, 10 nM, 9 nM, 8 nM, 7 nM, 6 nM, 5 nM, 4 nM, 3 nM, 2 nM, or 1 nM, e.g., as determined by surface plasmon resonance.

The term "antigen" or "Ag," as used herein, is defined as a molecule that provokes an immune response. This immune response may involve either antibody production, or the activation of specific immunologically competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

By "autoantigen" is meant an endogenous antigen that stimulates production of an autoimmune response, such as production of autoantibodies. Autoantigen also includes a self-antigen or antigen from a normal tissue that is the target of a cell-mediated or an antibody-mediated immune response that may result in the development of an autoimmune disease. Examples of autoantigens include, but are not limited to, PLA2R, and fragments thereof.

The term "limited toxicity," as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

"Autoantibody" refers to an antibody that is specific for an autoantigen.

The term "autoimmune disease," as used herein, is defined as a disorder or condition that results from an antibody-mediated autoimmune response against autoantigens. An autoimmune disease results in the production of autoantibodies that are inappropriately produced and/or excessively produced to a self-antigen or autoantigen.

As used herein, the term "autologous" is meant to refer to any material derived from the same individual to which it is later to be re-introduced into the individual.

"Allogeneic" refers to any material derived from a different animal of the same species.

"Xenogeneic" refers to any material derived from an animal of a different species.

"Chimeric autoantibody receptor" or "CAAR" refers to an engineered receptor that is expressed on cell, e.g., a T cell or any other effector cell type, e.g., an effector cell type capable of cell-mediated cytotoxicity. The CAAR includes an antigen or fragment thereof that is specific for an autoantibody and/or BCR, e.g., a pathogenic autoantibody and/or BCR. The CAAR optionally also includes a transmembrane domain, an intracellular domain and/or a signaling domain.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, for example, one or more amino acid residues within the extracellular regions of the CAAR of the invention can be replaced with other amino acid residues having a similar side chain or charge and the altered CAAR can be tested for the ability to bind autoantibodies using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

The term "effector function" refers to a specialized function of a cell.

As used herein, "endogenous" refers to any material from or produced inside an organism, cell, tissue or system.

As used herein, the term "exogenous" refers to any material introduced from or produced outside an organism, cell, tissue or system.

The term "expression," as used herein, is defined as the transcription and/or translation of a particular nucleotide sequence driven by a promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), retrotransposons (e.g. piggyback, sleeping beauty), and viruses (e.g., lentiviruses, retroviruses, adenoviruses, and adeno-associated viruses) that incorporate the recombinant polynucleotide.

"Homologous," as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity," as used herein, refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Intracellular domain" refers to a portion or region of a molecule that resides inside a cell.

The term "intracellular signaling domain" is meant to include any full-length or truncated portion of the intracellular domain sufficient to transduce the effector function signal.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus," as used herein, refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

As used herein, "plasma cells," refer to a type of white blood cells which can produce and secrete antibodies. Plasma cells are also referred to as plasmocytes, plasmacytes, or effector B cells. In some embodiments, these cells comprise B cell precursors capable of B-cell differentiation or B cells in the early stages of B cell differentiation, expressing a p chain on the cell surface as antigen receptor; B cells in which the transcription process has changed and IgM production has changed from membrane-type IgMs to secreted-type IgMs; mature B cells that have completed class-switching and secrete IgGs, IgAs, and IgMs; and B cells in the final stages of differentiation.

As used herein, the terms "phospholipase A2 receptor" or "M-type phospholipase A2 receptor" (PLA2R) are used interchangeably and refer to the major target antigen expressed in the kidney glomeruli in primary membranous nephropathy (MN) (Beck et al. 2009 N Engl J Med; 361: 11-21). The anti-PLA2R autoantibodies are predominantly of the IgG4 subclass but subclasses IgG1, IgG2, and IgG3 are also represented. Genetic variants of PLA2R were also shown to be associated with MN (Stanescu et al. 2011 N Engl J Med; 364(7):616-26).

As used herein, a PLA2R fragment refers to a shortened or truncated PLA2R protein. The polypeptide can have N-terminus or C-terminus truncations and/or also internal deletions. Examples of fragments are fragments comprising the C-type lectin domains ("CTLD") of PLA2R. In one embodiment, a PLA2R fragment includes the external domain of PLA2R, which is the amino acid residues 21-1397 of the human PLA2R (UniProtKB, Q13018) or any shorter portion of the amino acid residues 21-1397.

The term "polynucleotide," as used herein, is defined as a chain of nucleotides. Furthermore, nucleic acids are polymers of nucleotides. Thus, nucleic acids and polynucleotides, as used herein, are interchangeable. One skilled in the art has the general knowledge that nucleic acids are polynucleotides, which can be hydrolyzed into the monomeric "nucleotides." The monomeric nucleotides can be hydrolyzed into nucleosides. As used herein, polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. In some embodiments, a nucleic acid sequence is considered to have at least 95%, 96%, 97%, 98%, or 99% identity or homology to any nucleic acid sequence disclosed herein.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. In some embodiments, an amino acid sequence is considered to have at 95%, 96%, 97%, 98%, or 99% identity or homology to any amino acid sequence described herein.

The term "proinflammatory cytokine" refers to a cytokine or factor that promotes inflammation or inflammatory responses. Examples of proinflammatory cytokines include, but are not limited to, chemokines (CCL, CXCL, CX3CL, XCL), interleukins (such as, IL-1, IL-2, IL-3, IL-5, IL-6, IL-7, IL-9, I110 and IL-15), interferons (IFNγ), and tumor necrosis factors (TNFα and TNFβ).

The term "promoter," as used herein, is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

"Signaling domain" refers to the portion or region of a molecule that recruits and interacts with specific proteins in response to an activating signal.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cells that have been separated from the cells with which they are naturally associated in their natural state. In some embodiments, the cells are cultured in vitro. In other embodiments, the cells are not cultured in vitro.

The term "therapeutic," as used herein, means a treatment and/or prophylaxis. A therapeutic effect is obtained by suppression, remission, or eradication of a disease state.

The term "transfected" or "transformed" or "transduced," as used herein, refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

"Transmembrane domain" refers to a portion or a region of a molecule that spans a lipid bilayer membrane.

The phrase "under transcriptional control" or "operatively linked," as used herein, means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Chimeric Autoantibody Receptor (CAAR)

The present invention is partly based on the discovery that chimeric autoantibody receptors can be used to target B cells that express autoantibody-based B cell receptors, which after activation and autoantibody secretion, may cause an autoantibody-mediated kidney disease. The invention includes a chimeric autoantibody receptor (CAAR) specific for anti-phospholipase A2 receptor (PLA2R) B cell receptor (BCR), compositions comprising the CAAR, polynucleotides encoding the CAAR, vectors comprising a polynucleotide encoding the CAAR, and recombinant T cells comprising the CAAR. The invention also includes methods of making a genetically modified cell, e.g., a genetically modified T cell, expressing a PLA2R-CAAR wherein the expressed CAAR comprises a phospholipase PLA2R extracellular domain.

The present invention includes a technology for treating an autoantibody-mediated kidney disease. In particular, technologies that target B cells that ultimately produce the autoantibodies and display the autoantibodies on their cell surfaces, mark these B cells as disease-specific targets for therapeutic intervention. The invention therefore includes a method for efficiently targeting and killing the pathogenic B cells in autoantibody-mediated kidney diseases by targeting the disease-causing B cells using an antigen-specific (e.g., PLA2R) chimeric autoantibody receptor (or CAAR). In one embodiment of the present invention, only specific anti-PLA2R BCR-expressing B cells are killed, leaving intact the beneficial B cells and antibodies that protect from infection.

In one aspect, the invention includes a polynucleotide encoding a chimeric autoantibody receptor (CAAR), wherein the polynucleotide encodes a phospholipase A2 receptor (PLA2R) autoantigen or fragment thereof, and optionally, a transmembrane domain, an intracellular domain of a costimulatory molecule, and/or a signaling domain.

Autoantigen Moiety

In one embodiment, the CAAR of the invention comprises an autoantibody binding domain otherwise referred to as an autoantigen or a fragment thereof. The choice of autoantigen for use in the present invention depends upon the type of autoantibody or BCR being targeted (e.g. anti-PLA2R). For example, the autoantigen may be chosen because it recognizes a BCR or autoantibody on a target cell, such as a BCR-expressing B cell, associated with a particular autoantibody mediated kidney disease state, e.g. a glomerular disease and an primary membranous nephropathy.

In some instances, it is beneficial that the autoantibody binding domain is derived from the same species in which the CAAR will ultimately be used. For example, for use in humans, it may be beneficial that the autoantibody binding domain of the CAAR comprises a human autoantigen (or fragment thereof) that binds a human BCR or autoantibody.

In one exemplary embodiment, a genetically engineered chimeric autoantibody receptor includes PLA2R or fragments thereof, which binds an anti-PLA2R BCR, e.g., anti-PLA2R BCR on a B cell in a subject.

In one embodiment, the CAAR comprises an extracellular domain of PLA2R.

In some embodiments, the extracellular domain of PLA2R comprises an N-terminal cysteine rich domain (Ricin B type lectin domain), a Fibronectin type II domain, a C-type lectin domain 1, a C-type lectin domain 2, a C-type lectin domain 3, a C-type lectin domain 7, or a combination of any of the foregoing.

In some embodiments, the extracellular domain of PLA2R comprises the immunodominant epitope, N-terminal cysteine rich (CysR) domain (Ricin B type lectin domain), encoded by SEQ ID NO: 1, a Fibronectin type II domain encoded by SEQ ID NO: 3, a C-type lectin domain 1 encoded by SEQ ID NO: 5, and a C-type lectin domain 2 encoded by SEQ ID NO: 7. This extracellular domain of PLA2R is the extracellular domain of the construct designated as construct 4027.CF12 herein and is encoded by SEQ ID NO: 8, wherein the linker between the immunodominant epitope, N-terminal cysteine rich domain and the Fibronectin type II domain is encoded by SEQ ID NO: 2 and the linker between the Fibronectin type II domain and the C-type lectin domain 1 is encoded by SEQ ID NO: 4, and the linker between the C-type lectin domain 1 and the C-type lectin domain 2 is encoded by SEQ ID NO: 6.

In another embodiment, the extracellular domain of PLA2R comprises the extracellular domain of construct 4027.CF12 and additionally a C-type lectin domain 3 encoded by SEQ ID NO: 14. This latter extracellular domain of PLA2R is the extracellular domain of the construct designated as construct 4028.CF123 herein and is encoded by SEQ ID NO: 15, wherein the linkers between the immunodominant epitope, N-terminal cysteine rich domain, the Fibronectin type II, the C-type lectin domain 1 and the C-type lectin domain 2 are the same as those listed above herein for construct 4027.CF12 (SEQ ID NOS: 2, 4 and 6) and further wherein the linker between the C-type lectin domain 2 and the C-type lectin domain 3 is encoded by SEQ ID NO: 13.

In another embodiment, the extracellular domain of PLA2R comprises the extracellular domain of the construct referred to herein as construct C, comprising a cysteine rich domain. In certain embodiments, the cysteine rich domain comprises SEQ ID NO: 49, and may be encoded by SEQ ID NO: 47. In certain embodiments, the cysteine rich domain comprises SEQ ID NO: 1.

In another embodiment, the extracellular domain of PLA2R comprises the extracellular domain of the construct referred to herein as construct CF1, comprising a cysteine rich domain, a fibronectin type II domain, and a C-type lectin domain 1. In certain embodiments, the extracellular domain comprises SEQ ID NO: 51, and may be encoded by SEQ ID NO: 50.

In another embodiment, the extracellular domain of PLA2R comprises the extracellular domain of the construct referred to herein as construct CF123, comprising a cysteine rich domain, a fibronectin type II domain, a C-type lectin domain 1, a C-type lectin domain 2, and a C-type lectin domain 3. In certain embodiments, the extracellular domain comprises SEQ ID NO: 53, and may be encoded by SEQ ID NO: 52.

In another embodiment, the extracellular domain of PLA2R comprises the extracellular domain of the construct referred to herein as construct CF1237, comprising a cysteine rich domain, a fibronectin type II domain, a C-type lectin domain 1, a C-type lectin domain 2, a C-type lectin domain 3, and a C-type lectin domain 7. In certain embodiments, the extracellular domain comprises SEQ ID NO: 55, and may be encoded by SEQ ID NO: 54.

In another embodiment, the extracellular domain of PLA2R comprises the extracellular domain of the construct referred to herein as construct CF17, comprising a cysteine rich domain, a fibronectin type II domain, a C-type lectin domain 1, and a C-type lectin domain 7. In certain embodiments, the extracellular domain comprises SEQ ID NO: 57, and may be encoded by SEQ ID NO: 56.

In another embodiment, the extracellular domain of PLA2R comprises the extracellular domain of the construct referred to herein as construct C17, comprising a cysteine rich domain, a C-type lectin domain 1, and a C-type lectin domain 7. In certain embodiments, the extracellular domain comprises SEQ ID NO: 59, and may be encoded by SEQ ID NO: 58.

In another embodiment, the extracellular domain of PLA2R comprises the extracellular domain of the construct referred to herein as construct 4025.C, comprising a cysteine rich domain. In certain embodiments, the extracellular domain comprises SEQ ID NO: 61, and may be encoded by SEQ ID NO: 60.

In another embodiment, the extracellular domain of PLA2R comprises the extracellular domain of the construct referred to herein as construct 4026.CF1, comprising a cysteine rich domain, a fibronectin type II domain, a C-type lectin domain 1. In certain embodiments, the extracellular domain comprises SEQ ID NO: 40, and may be encoded by SEQ ID NO: 39.

In another embodiment, the extracellular domain of PLA2R comprises the extracellular domain of the construct referred to herein as construct 4027.CF12, comprising a cysteine rich domain, a fibronectin type II domain, a C-type lectin domain 1, and a C-type lectin domain 2. In certain embodiments, the extracellular domain comprises SEQ ID NO: 70, and may be encoded by SEQ ID NO: 8.

In another embodiment, the extracellular domain of PLA2R comprises the extracellular domain of the construct referred to herein as construct 4028.CF123, comprising a cysteine rich domain, a fibronectin type II domain, a C-type lectin domain 1, a C-type lectin domain 2, and a C-type lectin domain 3. In certain embodiments, the extracellular domain comprises SEQ ID NO: 71, and may be encoded by SEQ ID NO: 15.

Tolerable variations of the autoantigen or a fragment thereof will be known to those of skill in the art. For example, in some embodiments the autoantigen or a fragment thereof comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NO: 49, 51, 53, 55, 57, 59, 61, 63, 70 or 71. In some embodiments the autoantigen or a fragment thereof is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least or 99% sequence identity to the nucleic acid sequence set forth in SEQ ID NO: 8, 15, 47, 50, 52, 54, 56, 58, 60, or 62.

Transmembrane Domain

In some embodiments, the PLA2R CAAR comprises a transmembrane domain that is fused to the extracellular domain of the PLA2R CAAR. In one embodiment, the PLA2R CAAR comprises a transmembrane domain that naturally is associated with one of the domains in the PLA2R CAAR. In some instances, the transmembrane domain is selected or modified by amino acid substitution to avoid binding to the transmembrane domains of the same or different surface membrane proteins in order to minimize interactions with other members of the receptor complex.

The transmembrane domain may be derived either from a natural or from a synthetic source. When the source is natural, the domain may be derived from any membrane-bound or transmembrane protein. In one embodiment, the transmembrane domain may be synthetic, in which case it will comprise predominantly hydrophobic residues such as leucine and valine. In one aspect a triplet of phenylalanine, tryptophan and valine will be found at each end of a synthetic transmembrane domain. Optionally, a short oligo- or polypeptide linker, between 2 and 10 amino acids in length may form the linkage between the transmembrane domain and the cytoplasmic signaling domain of the PLA2R CAAR. A glycine-serine doublet provides a particularly suitable linker.

In some instances, a variety of spacer domains before the transmembrane domain can be employed as well including a hinge (e.g. a CD8 or human Ig (immunoglobulin) hinge), or a glycine-serine (GS) linker.

Examples of the hinge and/or transmembrane domain include, but are not limited to, a hinge and/or transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, killer immunoglobulin-like receptor (KIR), OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD1 id, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

In some embodiments, the PLA2R CAAR comprises a transmembrane domain, such as, but not limited to, a CD8 alpha transmembrane domain. In some embodiments, the CD8 alpha transmembrane domain comprises the amino acid sequence IYIWAPLAGTCGVLLLSLVITLYC (SEQ ID NO: 19). In some embodiments, the CD8 alpha transmembrane domain is encoded by the nucleotide sequence ATCTACATCTGGGCGCCCTTGGCCGGGACTTGTGG-GGTCCTTCTCCTGTCACT GGTTATCACCCTT-TACTGC (SEQ ID NO: 20).

In some embodiments the transmembrane domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 990/sequence identity to SEQ ID NO: 19, or is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 20.

In some embodiments, the PLA2R CAAR comprises a hinge domain such as, but not limited to, a CD8 alpha hinge domain. In some embodiments, the hinge domain comprises the amino acid sequence TTTPAPRPPTPAPTIA-SQPLSLRPEACRPAAGGAVHTRGLDFACD (SEQ ID NO: 43). In some embodiments, the hinge domain comprises the amino acid sequence FVPVFLPAKPTTTPAPRPPT-PAPTIASQPLSLRPEACRPAAGGAVHTRGLDFACD (SEQ ID NO: 44). In some embodiments, the hinge domain is encoded by the nucleotide sequence of SEQ ID NO: 10. In some embodiments, the hinge domain is encoded by the nucleotide sequence ACCACGACGCCAGCGCCGCGAC-CACCAACACCGGCGCCCACCATCGCGTCGC AGCCCCTGTCCCTGCGCCCAGAGGCGTGCCGGCC-AGCGGCGGGGGGCGCAGT GCACACGAGGGGGCTGGACTTCGCCTGTGAT (SEQ ID NO: 42). In some embodiments, the hinge domain is encoded by the nucleotide sequence TTCGTGCCGGTCTTCCTGCCAGCGAAGCCAAC-CACGACGCCAGCACCGCGAC CAC-CAACACCTGCGCCCAC-CATCGCGTCGCAGCCCCTGTCCCTGCGCCCAGA GGCGTGCA-GACCAGCAGCGGGGGGCGCAGTGCACACGAGGG-GGCTGGACTT CGCCTGTGAT (SEQ ID NO: 64). In some embodiments, the PLA2R CAAR comprises a transmembrane domain and a hinge domain.

In some embodiments the hinge domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO:43 or SEQ ID NO: 44, or is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 42 or SEQ ID NO: 64.

In some embodiments, the PLA2R CAAR comprises a glycine serine (GS) linker. In some embodiments, the PLA2R CAAR comprises a GS linker and a transmembrane domain. In some embodiments, the GS linker is encoded by the nucleotide sequence: GGTGGCGGAGGTTCTG-GAGGTGGAGGTTCC (SEQ ID NO: 68). In some embodiments, the GS linker comprises the amino acid sequence: GGGGSGGGGS (SEQ ID NO: 69). Those of skill in the art would be able to select the appropriate linker sequence, when appropriate for use in a CAAR construct.

Intracellular Domain of a Costimulatory Molecule

In some embodiments, the PLA2R CAAR comprises an intracellular domain of a costimulatory molecule. The intracellular domain of a costimulatory molecule of the PLA2R CAAR of the invention is a cytoplasmic domain responsible for the activation of at least one of the normal effector functions of the immune cell in which the PLA2R CAAR has been placed in.

Effector function of a T cell, for example, may be cytolytic activity or helper activity including the secretion of cytokines. Thus the term "intracellular domain of a costimulatory molecule" refers to the portion of a protein which transduces the effector function signal and directs the cell to perform a specialized function. While the entire intracellular domain of a costimulatory molecule can be employed, in many cases it is not necessary to use the entire domain. To the extent that a truncated portion of the intracellular domain of a costimulatory molecule is used, such truncated portion may be used in place of the intact domain as long as it transduces the effector function signal.

The intracellular domain of a costimulatory molecule refers to a portion of the CAAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, CDS, ICAM-1, GITR, BAFFR, HVEM (LIGHTR), SLAMF7, NKp80 (KLRF1), CD127, CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD1 id, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof. Thus, while the invention is exemplified primarily with 4-1BB (CD137) as the co-stimulatory signaling domains, other costimulatory domains are within the scope of the invention.

In one embodiment, the nucleic acid sequence of the intracellular domain of a costimulatory molecule encodes an amino acid sequence comprising costimulatory molecule 4-1BB (also known and referred to as CD137) intracellular domain: KRGRKKLLY-IFKQPFMRPVQTTQEEDGCSCRFPEEEEGGCEL (SEQ ID NO: 21). In still another embodiment, the nucleic acid sequence encoding the 4-1BB intracellular domain comprises: AAACGGGGCAGAAAGAAACTCCTGTATATAT-TCAAACAACCATTTATGAGAC CAGTACAAACTACT-CAAGAGGAAGATGGCTGTAGCTGCCGATTTCCAGAA-GA AGAAGAAGGAGGATGTGAACTG (SEQ ID NO: 22). In still another embodiment, the nucleic acid sequence encoding the 4-1BB intracellular domain comprises: SEQ ID NO: 66. The human intracellular 4-1BB domain provides co-stimulatory intracellular signaling upon binding to the extracellular autoantigen, such as PLA2R, or a fragment thereof, without the need of its original ligand.

In some embodiments the intracellular domain of a costimulatory molecule comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 21, or is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 22 or SEQ ID NO: 66.

It is well recognized that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Signaling Domain

In some embodiments, the PLA2R CAAR comprises a signaling domain. Primary cytoplasmic signaling sequences regulate primary activation of the TCR complex either in a stimulatory manner or in an inhibitory manner. Primary cytoplasmic signaling sequences that act in a stimulatory manner may contain signaling motifs which are known as immunoreceptor tyrosine-based activation motifs or ITAMs.

Examples of ITAM containing primary signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that signaling molecule in the CAAR of the invention comprises a signaling domain derived from CD3-zeta.

In one embodiment, the signaling domain of the CAAR can be designed to comprise the CD3-zeta signaling domain by itself or combined with any other desired cytoplasmic domain(s) useful in the context of the CAAR of the invention. For example, the signaling domain of the CAAR can comprise a CD3 zeta chain portion and a costimulatory signaling domain.

In some embodiments, the PLA2R CAAR comprises a CD3-zeta signaling domain by itself or in combination with any other desired cytoplasmic domain(s) useful in the context of the PLA2R CAAR of the invention. For example, the PLA2R CAAR can comprise a CD3 zeta chain portion and an intracellular domain of a costimulatory molecule. In some embodiments, the CD3 zeta chain portion is a human T-cell surface glycoprotein CD3 zeta chain isoform 3 intracellular domain (human CD247). The human intracellular CD3 zeta domain provides stimulatory intracellular signaling upon binding to the extracellular autoantigen, such as PLA2R or a fragment thereof, without HLA restriction.

In one embodiment, the nucleic acid sequence of the signaling domain comprises a nucleic acid sequence encoding a CD3 zeta signaling domain. In another embodiment, the nucleic acid sequence of the CD3 zeta signaling domain encodes an amino acid sequence comprising RVKFSRS-ADAPAYKQGQNQLYNELNLGRREEYDVLDKRR-GRDPEMGGKPRRK NPQEGLYNELQKDKMAEAYSEI-GMKGERRRGKGHDGLYQGLSTATKDTYDAL HMQALPPR (SEQ ID NO: 23). In another embodiment, the nucleic acid sequence of the CD3 zeta signaling domain encodes an amino acid sequence comprising RVKFSRS- ADAPAYQQGQNQLYNELNLGRREEYDVLDKRR-GRDPEMGGKPRRK NPQEGLYNELQKDKMAEAYSEI-GMKGERRRGKGHDGLYQGLSTATKDTYDAL HMQALPPR (SEQ ID NO: 45). In another embodiment, the nucleic acid sequence encoding the CD3 zeta signaling domain comprises: AGAGTGAAGTTCAGCAG-GAGCGCAGACGCCCCCGCGTACCAGCAGGGCCAG AACCAGCTCTATAACGAGCT-CAATCTAGGACGAAGAGAGGAGTACGATGTTT TGGACAAGAGACGTGGCCGGGACCCT-GAGATGGGGGGAAAGCCGAGAAGGA AGAACCCTCAGGAAGGCCTGTACAAT-GAACTGCAGAAAGATAAGATGGCGG AGGCCTA-CAGTGAGATTGGGATGAAAGGCGAGCGCCG-GAGGGGCAAGGGGC ACGATGGCCTTTACCAGGGTCTCAGTACAGCCAC-CAAGGACACCTACGACGC CCTTCA-CATGCAGGCCCTGCCCCCTCGC (SEQ ID NO: 24). In another embodiment, the nucleic acid sequence encoding the CD3 zeta signaling domain comprises SEQ ID NO: 74.

In some embodiments, the signaling domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 23 or SEQ ID NO: 45, or is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 24 or SEQ ID NO: 74.

Other Domains

In some embodiments, the PLA2R CAAR and the polynucleotide encoding the PLA2R CAAR comprise a human T cell surface glycoprotein CD8 alpha chain signal peptide. The human CD8 alpha signal peptide is responsible for the translocation of the receptor to the T cell surface.

In one embodiment, the polynucleotide encoding the PLA2R CAAR comprises a nucleic acid sequence of a peptide linker. In another embodiment, the PLA2R CAAR comprises a peptide linker. In yet another embodiment, the cytoplasmic signaling sequences within the intracellular signaling domain of the PLA2R CAAR can be linked to each other in a random or specified order. Optionally, a short oligo- or polypeptide linker, for example, between 2 and 10 amino acids in length may form the linkage. A glycine-serine doublet is a particularly suitable linker.

In some embodiments, the CAAR comprises a transmembrane domain and/or a cytoplasmic (intracellular) domain from a killer immunoglobulin-like receptor (KIR) family protein. The KIR gene family has at least 15 gene loci (KIR2DL1, KIR2DL2/L3, KIR2DL4, KIR2DL5A, KIR2DL5B, KIR2DS1, KIR2DS2, KIR2DS3, KIR2DS4, KIR2DS5, KIR3DL1/S1, KIR3DL2, KIR3DL3) and two pseudogenes (KIR2DP1 and KIR3DP1) encoded within a 100-200 Kb region of the Leukocyte Receptor Complex (LRC) located on chromosome 19 (19q13.4). The LRC constitutes a large, 1 Mb, and dense cluster of rapidly evolving immune genes which contains genes encoding other cell surface molecules with distinctive Ig-like extracellular domains. In addition, the extended LRC contains genes encoding the transmembrane adaptor molecules DAP10 and DAP12. Thus, a cell comprising the CAAR of the invention comprising a KIR transmembrane domain and/or cytoplasmic domain may also comprise a polynucleotide encoding DAP10 or DAP12. In certain embodiments, the KIR is KIRS2 or KIR2DS2

In certain embodiments, the CAAR is encoded by a nucleic acid sequence selected from the group consisting of SEQ ID NOs: 11, 17, 25, 27, 29, 31, 33, 35, 37, and 39. In certain embodiments, the CAAR comprises an amino acid sequence selected from the group consisting of SEQ ID NOs: 12, 18, 26, 28, 30, 32, 34, 36, 38, 40, and 42.

Tolerable variations of the CAAR sequences will be known to those of skill in the art. For example, in some embodiments the CAAR comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NOs: 12, and 18, 26, 28, 30, 32, 34, 36, 38, or 40. In some embodiments the CAAR is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 11, 17, 25, 27, 29, 31, 33, 35, 37, or 39.

Vector Comprising the PLA2R CAAR

In some embodiments, a $3^{rd}$ generation self-inactivating lentiviral vector plasmid can be used in which the expression of the CAR is regulated by the human elongation factor 1 alpha promoter. This results in stable (permanent) expression of the CAR in the host T cell. As an alternative approach, the encoding mRNA can be electroporated into the host cell, which would achieve the same therapeutic effect as the virally transduced T cells, but would not be permanent because the mRNA would dilute out with cell division.

In one aspect, the invention includes a vector comprising a polynucleotide encoding a chimeric autoantibody receptor (CAAR), wherein the polynucleotide comprises an extracellular domain comprising a human PLA2R autoantigen or fragment thereof, and optionally, a transmembrane domain, and/or an intracellular signaling domain. In one embodiment, the vector comprises any of the nucleic acid sequences encoding the CAAR as described herein. In another embodiment, the vector comprises a plasmid vector, viral vector, retrotransposon (e.g. piggyback, sleeping beauty), site directed insertion vector (e.g. CRISPR, Zinc finger nucleases, TALEN), or suicide expression vector, or other known vector in the art.

All constructs disclosed herein can be used with 3rd generation lentiviral vector plasmids, other viral vectors, or RNA approved for use in human cells. In one embodiment, the vector is a viral vector, such as a lentiviral vector. In another embodiment, the vector is a RNA vector.

The expression of the PLA2R CAAR can be verified by sequencing. Expression of the full length CAAR protein may be verified using immunoblot, immunohistochemistry, flow cytometry or other technology well known and available in the art.

The present invention also provides a vector in which DNA encoding the CAAR of the present invention is inserted. Vectors, including those derived from retroviruses such as lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of resulting in low immunogenicity in the subject into which they are introduced.

In brief summary, the expression of natural or synthetic polynucleotides encoding CAARs is typically achieved by operably linking a nucleic acid encoding the CAAR polypeptide or portions thereof to a promoter (e.g. EF1alpha promoter), and incorporating the construct into an expression vector. The vector is one generally capable of replication in a mammalian cell, and/or also capable of integration into the cellular genome of the mammal. Typical vectors contain transcription and translation terminators, initiation sequences, and promoters useful for regulation of the expression of the desired nucleic acid sequence.

The nucleic acid can be cloned into any number of different types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

The expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the elongation factor-1α promoter, as well as human gene promoters such as, but not limited to, the actin promoter, the myosin promoter, the hemoglobin promoter, when appropriate for use in a CAAR construct.

Further, the invention should not be limited to the use of constitutive promoters. Inducible promoters are also contemplated as part of the invention. The use of an inducible promoter provides a molecular switch capable of turning on expression of the polynucleotide sequence, which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. In some embodiments, an inducible promoter is activated in response to a extracellular ligand. For example, in some embodiments, the inducible promoter is activated (and the expression of the CAAR is regulated) by an extracellular ligand binding to a synthetic receptor. For example, in some embodiments, a synthetic receptor, e.g., a synthetic Notch receptor (i.e., "synNotch") may be employed as a binding-triggered transcriptional switch that, when bound to its ligand, activates a promoter to which a nucleic acid sequence encoding the CAAR is operably linked. Accordingly, as a non-limiting example, such systems may require the presence of a ligand (e.g., to which the synNotch binds) for the immune cell to be responsive to a BCR or autoantibody (e.g., to which the CAAR binds). The requirement of particular combinations to generate certain signaling outputs in molecular circuits results in a logic gate. See, for example, Roybal et al., 2016 Cell 164(4):770-9.

Examples of other systems for expressing or regulating expression of a chimeric receptor include those described in Wu et al. (2015) Science 350: aab4077; Fedorov et al. (2014) Cancer Journal 20:160-165; Kloss et al. (2013) Nature Biotechnology 31: 71-75; Sakemura et al. (2016) Cancer Immunol. Res. 4:658-668; Hill et al. (2018) Nature Chemical Biology 14:112-117; Di Stasi et al. (2011) N. Engl. J. Med. 365:1673-1683; Budde et al. (2013) PLoS One 8: e82742; Wei et al. (2012) Nature 488: 384-388; Ma et al. (2016) Proc. Natl. Acad. Sci. USA 113: E450-458; Rodgers et al. (2016) Proc. Natl. Acad. Sci. USA 113: E459-468; Kudo et al. (2014) Cancer Res. 74: 93-103, and Chen et al. (2010) Proc. Natl. Acad. Sci. USA 107, 8531-8536.

In order to assess the expression of a CAAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY).

Biological methods for introducing a polynucleotide of interest into a host cell include the use of DNA and RNA vectors. RNA vectors include vectors having a RNA promoter and/other relevant domains for production of a RNA transcript. Viral vectors, and especially retroviral vectors, have become the most widely used method for inserting genes into mammalian, e.g., human cells. Other viral vectors may be derived from lentivirus, poxviruses, herpes simplex virus, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances, which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Any domains and/or fragments of the CAAR, vector, and the promoter may be synthesized gene fragments amplified by PCR or any other means known in the art.

Cells Comprising the CAAR

In another aspect, the invention includes a genetically modified cell comprising the PLA2R chimeric autoantibody receptor (CAAR) disclosed herein.

In another embodiment, the genetically modified cell expresses the PLA2R CAAR. In this embodiment, the cell has high affinity for PLA2R autoantibody-based B cell receptors (BCRs) on B cells or rarely, on B cells that have differentiated into plasma cells that have not yet downregulated their BCR. As a result, the genetically modified cell can induce direct killing of anti-PLA2R B cells or indirect killing of plasma cells expressing PLA2R autoantibodies. In yet another embodiment, the genetically modified cell has low affinity for antibodies bound to an Fc receptor.

In one embodiment, the genetically modified cell is a T cell, such as a helper T cell, a cytotoxic T cell, a memory T cell, regulatory T cell, gamma delta T cell, a natural killer cell, cytokine induced killer cell, a cell line thereof, a T memory stem cell, or other T effector cell. It is also useful for the T cell to have limited toxicity toward healthy cells and specificity to cells expressing autoantibodies. Such specificity prevents or reduces off-target toxicity that is prevalent in current therapies that are not specific for autoantibodies. In one embodiment, the T cell has limited toxicity toward healthy cells. In one embodiment the T cell is an autologous cell. In another embodiment, the T cell is an allogeneic cell.

In some embodiments, the invention includes genetically modified immune cells derived from pluripotent stem cells that were differentiated in vitro. In other embodiments, the invention includes T cells, such as primary cells, expanded T cells derived from primary T cells, T cells derived from stem cells differentiated in vitro, T cell lines such as Jurkat cells, other sources of T cells, combinations thereof, and other effector cells. For example, a transduced Jurkat cell line with a NFAT response element followed by GFP can be used to detect and isolate PLA2R specific B cells and to clone the PLA2R specific antibody repertoire in a comprehensive and unbiased fashion. The interacting B and Jurkat cells can be detected as GFP positive doublets or multimers and sorted by flow cytometry. Expression cloning of the B cell receptor encoding genes will provide further information on how autoimmunity and autoantibodies in autoantibody-mediated kidney diseases, such as glomerular disease and primary membranous nephropathy develop.

The functional ability of CAARs to specifically bind to autoantibodies and sera, for example, primary membranous nephropathy sera, can be assessed in a Jurkat reporter cell line, which depends on activation of the CAAR by binding to plate-bound autoantibody (in response to which the activated cells fluoresce green due to an NFAT-GFP reporter construct contained therein). Such methods are useful and reliable qualitative measures for functional binding ability. The proper processing of the autoantigen on the cell surface is also important and can be measured using monoclonal antibodies. Furthermore, truncations of PLA2R based on major disease epitopes are also useful and included herein. Versions using a different length hinge region or GS linker are also useful. With regard to safety, preventing or reducing possible homophilic and heterophilic interactions and activation (e.g. PLA2R-PLA2R) between the transduced cells or toward podocytes is preferred.

Further assessment of efficacy and safety of the CAAR can be performed, for example, as follows:

Constructs can be transiently transfected into human cells, such as 293T/17. The surface expression can be detected with monoclonal antibodies (either IgG or ScFv) or serum antibodies from PLA2R MN patients specific for the above-mentioned extracellular domains, the linker between the domains, or other structure included in the CAAR. Binding can be verified with specific secondary antibodies and quantified by flow cytometry.

Production of membrane expressed constructs of human anti-PLA2R antibodies of any isotype can serve as target cells for testing the different PLA2R-CAARs. Additional target cell lines can be produced as needed by expression of human monoclonal antibodies on the surface of cell lines (e.g. Nalm6 or K562 cells).

Autoimmune Diseases

The present invention also provides methods for preventing, treating and/or managing a disorder or autoimmune disease associated with autoantibody-expressing cells in the context of an autoantibody-mediated kidney disease. The methods comprise administering to a subject in need thereof a genetically modified T cell comprising the CAAR of the invention that binds to the autoantibody-expressing cell. In one aspect, the subject is a human. Non-limiting examples of an autoantibody-mediated kidney disease include to glomerular disease and primary membranous nephropathy.

In the methods of treatment, T cells isolated from a subject can be modified to express the appropriate CAAR, expanded ex vivo and then reinfused into the same subject (e.g., the T cells are autologous T cells). In some embodiments, the T cells are reinfused into a different subject than the original T cells' donor (e.g., the T cells are allogeneic T cells). The modified T cells recognize target cells, such as anti-PLA2R B cells or PLA2R autoantibody producing B cells or plasma cells, and become activated, resulting in killing of the autoimmune target cells.

Relapse may also occur in patients with an autoimmune disease, for example in primary membranous nephropathy patients. In patients treated with rituximab, the relapse may be mediated by persistence of the same autoantibody B cell clones, whereas remission is associated with disappearance of these clones. By infusing PLA2R CAAR T cells, the autoimmune cells are depleted to induce long-term remission, possibly due to the longevity of the PLA2R CAAR T cells and/or autoantigen-reactive clones do not re-appear.

To monitor PLA2R CAAR-expressing cells in vitro, in situ, or in vivo, PLA2R CAAR cells can further express a detectable marker. When the PLA2R CAAR binds the target, the detectable marker is activated and expressed, which can be detected by assays known in the art, such as flow cytometry. In one embodiment, the PLA2R CAAR includes a NFAT response element and a detectable marker, such as a green fluorescent protein (GFP), to detect and quantify PLA2R CAAR expressing cells.

Sources of T Cells

Prior to expansion and genetic modification, T cells (e.g., autologous or allogeneic T cells) are obtained from a subject. Examples of subjects include humans, dogs, cats, mice, rats, and transgenic species thereof. T cells can be obtained from a number of sources, including skin, peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^+$, $GITR^+$, and $FoxP3^+$. Alternatively, in certain embodiments, T regulatory cells are depleted by anti-CD25 conjugated beads or other similar method of selection. In other embodiments, subpopulation of T cells, such as, but not limited to, cells positive or expressing high levels of one or more surface markers e.g. CD28+, CD8+, CCR7+, CD27+, CD127+, CD45RA+, and/or CD45RO+ T cells, can be isolated by positive or negative selection techniques.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment, a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs may, for example, inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In another embodiment, the cells are isolated prior to and can be frozen for later use for treatment following B-cell ablative therapy, e.g., Rituxan.

In a further embodiment of the present invention, T cells are obtained from a patient directly following treatment. In this regard, it has been observed that following certain treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., *Transplant Proc.* 30(8):3975-3977, 1998; Haanen et al., *J.Exp. Med.* 190(9):13191328, 1999; Garland et al., *J. Immunol Meth.* 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment, the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-7, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, $CD4^+$) that is greater than the cytotoxic or suppressor T cell population ($T_C$, $CD8^+$). E vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_C$ cells or $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

In one aspect, the invention includes a method for treating an autoantibody-mediated kidney disease in a subject. The method comprises: administering to the subject an effective amount of a genetically modified T cell comprising a polynucleotide encoding a chimeric autoantibody receptor (CAAR), wherein the polynucleotide encodes a phospholipase A2 receptor (PLA2R) autoantigen or fragment thereof, and optionally, a transmembrane domain, an intracellular domain of a costimulatory molecule, and/or a signaling domain, thereby treating the autoantibody-mediated kidney disease in the subject.

In another aspect, the invention includes a method for preventing or reducing glomerulus damage in a subject at risk or suffering from an autoantibody-mediated kidney disease. The method comprises: administering to the subject an effective amount of a genetically modified T cell comprising a polynucleotide encoding a CAAR, wherein the polynucleotide encodes a PLA2R autoantigen or fragment thereof, and optionally, a transmembrane domain, an intracellular domain of a costimulatory molecule, and/or a signaling domain, thereby preventing or reducing glomerulus damage in the subject.

In one embodiment, the autoantibody-mediated kidney disease is selected from the group consisting of a glomerular disease and a primary membranous nephropathy, e.g., a primary membranous nephropathy mediated by or otherwise associated with a known anti-PLA2R autoantibody and/or BCR. In another embodiment, the subject is a human.

Without wishing to be bound by any particular theory, the anti-autoantibody immune response elicited by the CAAR-modified T cells may be an active or a passive immune response. In yet another embodiment, the modified T cell targets a B cell. For example, autoantibody expressing B cells may be susceptible to indirect destruction by CAAR-redirected T cells that have previously reacted against adjacent autoantibody-expressing cells.

In one embodiment, the genetically modified T cells of the invention are modified by a fully-human CAAR. In one embodiment, the fully-human CAAR-genetically modified T cells may be a type of vaccine for ex vivo immunization and/or in vivo therapy in a mammal. In one embodiment, the mammal is a human.

With respect to ex vivo immunization, at least one of the following occurs in vitro prior to administering the cell into a mammal: i) expansion of the cells, ii) introducing to the cells a polynucleotide encoding a CAAR iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a CAAR disclosed herein. The CAAR-modified cell can be administered to a mammalian recipient to provide a therapeutic benefit. The mammalian recipient may be a human and the CAAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also includes compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the PLA2R CAAR-modified T cells of the invention are used in the treatment of diseases, disorders and conditions associated with expression of autoantibodies. In certain embodiments, the cells of the invention are used in the treatment of patients at risk for developing autoimmune kidney diseases, disorders and conditions associated with expression of autoantibodies. Thus, the present invention provides methods for the treatment or prevention of autoimmune kidney diseases, disorders and conditions associated with expression of autoantibodies (PLA2R) comprising administering to a subject in need thereof, a therapeutically effective amount of the CAAR-modified T cells of the invention.

The CAAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-BCR effective amount," "an autoimmune disease-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, activated T cells are administered to a subject. Subsequent to administration, blood is redrawn or apheresis is performed, and T cells are activated and expanded therefrom using the methods described here, and are then reinfused back into the patient. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The cells of the invention to be administered may be autologous, allogeneic or xenogeneic with respect to the subject undergoing therapy.

Administration of the cells of the invention may be carried out using any convenient means, including by aerosol inhalation, injection, ingestion, transfusion, implantation or transplantation. The compositions described herein may be administered to a patient transarterially, subcutaneously, intradermally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are administered by i.v. injection. The compositions of T cells may be injected directly into a lymph node, or other site of pathophysiologic activity.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as immunosuppressive agents, such as azathioprine, methotrexate, mycophenolate, antibodies, or other immunoablative agents such as CAMPATH, anti-CD3 antibodies or other antibody therapies, Cytoxan, fludarabine, mycophenolic acid, steroids, FR901228, cytokines, and irradiation. These drugs may, for example, inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. In further embodiments, the T cells of the invention may be used in combination with complement inhibitors to reduce risk of complement-mediated cytotoxicity or an antibody anti-FcRn, IVIg, or plasmapheresis in order to reduce the anti-PLA2R antibody concentration before therapy. In yet other embodiments, a mild lymphodepletion regimen (e.g. Low-dose fludarabine or Cytoxan) might precede treatment with the T cells of the invention.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods used in the performance of the experiments disclosed herein are now described.

—CAAR Constructs

```
A) Domains comprised in PLA2R-CAAR Construct 4027.CF12
Cysteine-rich (CysR) domain (Ricin B type lectin domain)
                                                    (SEQ ID NO: 1)
AAGGGCATCTTCGTGATCCAGAGCGAGAGCCTGAAGAAGTGCATCCAGGCCG

GCAAGAGCGTGCTGACCCTGGAAAATTGCAAGCAGGCCAACAAGCACATGC

TGTGGAAATGGGTGTCCAACCACGGCCTGTTCAACATCGGCGGCTCTGGATG

TCTGGGCCTGAATTTCTCTGCCCCTGAGCAGCCTCTGAGCCTGTACGAGTGTG

ATAGCACCCTGGTGTCCCTGAGATGGCGGTGCAACCGGAAGATGATCACAGG

CCCTCTGCAGTACTCTGTGCAGGTCGCCCACGACAATACCGTGGTGGCCAGC

AGAAAGTACATCCACAAGTGGATCAGCTACGGCAGCGGCGGAGGCGACATC

TGTGAATAC
```

-continued

Linker between ricin B type lectin domain and fibronectin type II domain
(SEQ ID NO: 2)
CTGCACAAGGATCTGCACACCATCAAGGGCAAC Fibronectin type-2 domain
(SEQ ID NO: 3)
ACCCACGGAATGCCCTGCATGTTCCCGTTTCAGTACAACCACCAGTGGCACC
ACGAGTGCACCAGAGAAGGCAGAGAGGACGACCTGCTTTGGTGCGCCACAA
CCAGCAGATACGAGCGGGATGAGAAGTGGGGCTTCTGCCCTGAT Linker between fibronectin type II domain and C-type lectin domain 1
(SEQ ID NO: 4)
CCTACCTCTGCCGAAGTGGGCTGCGATACCATCTGGGAGAAAGACCTG C-type lectin domain 1
(SEQ ID NO: 5)
AACAGCCACATCTGCTACCAGTTCAACCTGCTGTCCAGCCTGTCTTGGAGCGA
GGCCCACAGCAGCTGTCAAATGCAAGGCGGCACACTGCTGAGCATCACCGAC
GAGACAGAGGAAAACTTCATCCGCGAGCACATGAGCAGCAAGACCGTGGAA
GTGTGGATGGGACTGAACCAGCTGGATGAGCATGCCGGATGGCAGTGGAGTG
ATGGCACCCCTCTGAACTACCTGAACTGGTCCCCTGAAGTGAACTTCGAGCC
CTTCGTGGAAGATCACTGCGGCACCTTCAGCAGCTTCATGCCCAGCGCTTGG
AGAAGCAGAGACTGCGAGAGCACCCTGCCTTACATCTGCAAG Linker between C-type lectin domain 1 and C-type lectin domain 2
(SEQ ID NO: 6)
AAGTACCTGAACCACATCGACCACGAGATCGTGGAAAAGGACGCCTGGAAG
TACTACGCCACACACTGCGAGCCTGGCTGGAACCCC C-type lectin domain 2
(SEQ ID NO: 7)
TACAACCGGAACTGCTACAAGCTGCAGAAAGAGGAAAAGACCTGGCACGAG
GCCCTGAGAAGCTGCCAGGCCGATAATAGCGCCCTGATCGACATCACAAGCC
TGGCCGAGGTGGAATTTCTGGTCACTCTGCTGGGCGACGAGAACGCCTCTGA
GACATGGATCGGCCTGTCCAGCAACAAGATCCCCGTGTCCTTCGAGTGGTCC
AACGACAGCAGCGTGATCTTCACCAACTGGCACACCCTGGAACCTCACATCT
TCCCCAACAGATCCCAGCTGTGTGTGTCCGCCGAGCAGTCTGAAGGCCACTG
GAAAGTGAAGAACTGCGAGGAACGGCTGTTCTACATCTGTAAA Extracellular domains of PLA2R CAAR Construct 4027.CF12
(SEQ ID NO: 8; See FIG. 2D)
AAGGGCATCTTCGTGATCCAGAGCGAGAGCCTGAAGAAGTGCATCCAGGCCG
GCAAGAGCGTGCTGACCCTGGAAAATTGCAAGCAGGCCAACAAGCACATGC
TGTGGAAATGGGTGTCCAACCACGGCCTGTTCAACATCGGCGGCTCTGGATG
TCTGGGCCTGAATTTCTCTGCCCCTGAGCAGCCTCTGAGCCTGTACGAGTGTG
ATAGCACCCTGGTGTCCCTGAGATGGCGGTGCAACCGGAAGATGATCACAGG
CCCTCTGCAGTACTCTGTGCAGGTCGCCCACGACAATACCGTGGTGGCCAGC
AGAAAGTACATCCACAAGTGGATCAGCTACGGCAGCGGCGGAGGCGACATC
TGTGAATACCTGCACAAGGATCTGCACACCATCAAGGGCAACACCCACGGAA
TGCCCTGCATGTTCCCGTTTCAGTACAACCACCAGTGGCACCACGAGTGCACC
AGAGAAGGCAGAGAGGACGACCTGCTTTGGTGCGCCACAACCAGCAGATAC
GAGCGGGATGAGAAGTGGGGCTTCTGCCCTGATCCTACCTCTGCCGAAGTGG
GCTGCGATACCATCTGGGAGAAAGACCTGAACAGCCACATCTGCTACCAGTT -continued

CAACCTGCTGTCCAGCCTGTCTTGGAGCGAGGCCCACAGCAGCTGTCAAATG

CAAGGCGGCACACTGCTGAGCATCACCGACGAGACAGAGGAAAACTTCATC

CGCGAGCACATGAGCAGCAAGACCGTGGAAGTGTGGATGGGACTGAACCAG

CTGGATGAGCATGCCGGATGGCAGTGGAGTGATGGCACCCCTCTGAACTACC

TGAACTGGTCCCCTGAAGTGAACTTCGAGCCCTTCGTGGAAGATCACTGCGG

CACCTTCAGCAGCTTCATGCCCAGCGCTTGGAGAAGCAGAGACTGCGAGAGC

ACCCTGCCTTACATCTGCAAGAAGTACCTGAACCACATCGACCACGAGATCG

TGGAAAAGGACGCCTGGAAGTACTACGCCACACACTGCGAGCCTGGCTGGA

ACCCCTACAACCGGAACTGCTACAAGCTGCAGAAAGAGGAAAAGACCTGGC

ACGAGGCCCTGAGAAGCTGCCAGGCCGATAATAGCGCCCTGATCGACATCAC

AAGCCTGGCCGAGGTGGAATTTCTGGTCACTCTGCTGGGCGACGAGAACGCC

TCTGAGACATGGATCGGCCTGTCCAGCAACAAGATCCCCGTGTCCTTCGAGT

GGTCCAACGACAGCAGCGTGATCTTCACCAACTGGCACACCCTGGAACCTCA

CATCTTCCCCAACAGATCCCAGCTGTGTGTGTCCGCCGAGCAGTCTGAAGGC

CACTGGAAAGTGAAGAACTGCGAGGAACGGCTGTTCTACATCTGTAAA

Extracellular domains of Construct 4027.CF12

(SEQ ID NO: 70)

KGIFVIQSESLKKCIQAGKSVLTLENCKQANKHMLWKWVSNHGLFNIGGSGCLG

LNFSAPEQPLSLYECDSTLVSLRWRCNRKMITGPLQYSVQVAHDNTVVASRKYI

HKWISYGSGGGDICEYLHKDLHTIKGNTHGMPCMFPFQYNHQWHHECTREGRE

DDLLWCATTSRYERDEKWGFCPDPTSAEVGCDTIWEKDLNSHICYQFNLLSSLS

WSEAHSSCQMQGGTLLSITDETEENFIREHMSSKTVEVWMGLNQLDEHAGWQW

SDGTPLNYLNWSPEVNFEPFVEDHCGTFSSFMPSAWRSRDCESTLPYICKKYLNH

IDHEIVEKDAWKYYATHCEPGWNPYNRNCYKLQKEEKTWHEALRSCQADNSAL

IDITSLAEVEFLVTLLGDENASETWIGLSSNKIPVSFEWSNDSSVIFTNWHTLEPHIF

PNRSQLCVSAEQSEGHWKVKNCEERLFYICKKAGHVLSDAESGCQ

Link between C-type lectin domain 2 and CD8 hinge (SEQ ID NO: 9)

AAGGCCGGCCACGTGCTGTCCGATGCCGAGAGTGGATGTCAATCCGGA

CD8 hinge (SEQ ID NO: 10)

ACCACGACGCCAGCGCCGCGACCACCAACACCGGCGCCCACCATCGCGTCGC

AGCCCCTGTCCCTGCGCCCAGAGGCGTGCCGGCCAGCGGCGGGGGGCGCAGT

GCACACGAGGGGGCTGGACTTCGCCTGT

Nucleic acid sequence of PLA2R-CAAR Construct 4027.CF12

(SEQ ID NO: 11)

ATGCTGCTGAGCCCTAGCCTGCTGCTGCTCCTGCTTCTTGGAGCCCCTAGAGG

ATGTGCCGGATCTGAAGGTGTTGCCGCCGCTCTGACACCCGAGAGACTGCTG

GAATGGCAGGACAAGGGCATCTTCGTGATCCAGAGCGAGAGCCTGAAGAAG

TGCATCCAGGCCGGCAAGAGCGTGCTGACCCTGGAAAATTGCAAGCAGGCCA

ACAAGCACATGCTGTGGAAATGGGTGTCCAACCACGGCCTGTTCAACATCGG

CGGCTCTGGATGTCTGGGCCTGAATTTCTCTGCCCCTGAGCAGCCTCTGAGCC

TGTACGAGTGTGATAGCACCCTGGTGTCCCTGAGATGGCGGTGCAACCGGAA

GATGATCACAGGCCCTCTGCAGTACTCTGTGCAGGTCGCCCACGACAATACC

GTGGTGGCCAGCAGAAAGTACATCCACAAGTGGATCAGCTACGGCAGCGGC

-continued

GGAGGCGACATCTGTGAATACCTGCACAAGGATCTGCACACCATCAAGGGCA

ACACCCACGGAATGCCCTGCATGTTCCCGTTTCAGTACAACCACCAGTGGCA

CCACGAGTGCACCAGAGAAGGCAGAGAGGACGACCTGCTTTGGTGCGCCAC

AACCAGCAGATACGAGCGGGATGAGAAGTGGGGCTTCTGCCCTGATCCTACC

TCTGCCGAAGTGGGCTGCGATACCATCTGGGAGAAAGACCTGAACAGCCACA

TCTGCTACCAGTTCAACCTGCTGTCCAGCCTGTCTTGGAGCGAGGCCCACAGC

AGCTGTCAAATGCAAGGCGGCACACTGCTGAGCATCACCGACGAGACAGAG

GAAAACTTCATCCGCGAGCACATGAGCAGCAAGACCGTGGAAGTGTGGATG

GGACTGAACCAGCTGGATGAGCATGCCGGATGGCAGTGGAGTGATGGCACCC

CTCTGAACTACCTGAACTGGTCCCCTGAAGTGAACTTCGAGCCCTTCGTGGAA

GATCACTGCGGCACCTTCAGCAGCTTCATGCCCAGCGCTTGGAGAAGCAGAG

ACTGCGAGAGCACCCTGCCTTACATCTGCAAGAAGTACCTGAACCACATCGA

CCACGAGATCGTGGAAAAGGACGCCTGGAAGTACTACGCCACACACTGCGA

GCCTGGCTGGAACCCCTACAACCGGAACTGCTACAAGCTGCAGAAAGAGGA

AAAGACCTGGCACGAGGCCCTGAGAAGCTGCCAGGCCGATAATAGCGCCCT

GATCGACATCACAAGCCTGGCCGAGGTGGAATTTCTGGTCACTCTGCTGGGC

GACGAGAACGCCTCTGAGACATGGATCGGCCTGTCCAGCAACAAGATCCCCG

TGTCCTTCGAGTGGTCCAACGACAGCAGCGTGATCTTCACCAACTGGCACAC

CCTGGAACCTCACATCTTCCCCAACAGATCCCAGCTGTGTGTGTCCGCCGAGC

AGTCTGAAGGCCACTGGAAAGTGAAGAACTGCGAGGAACGGCTGTTCTACAT

CTGTAAAAAGGCCGGCCACGTGCTGTCCGATGCCGAGAGTGGATGTCAATCC

GGAACCACGACGCCAGCGCCGCGACCACCAACACCGGCGCCCACCATCGCGT

CGCAGCCCCTGTCCCTGCGCCCAGAGGCGTGCCGGCCAGCGGCGGGGGGCGC

AGTGCACACGAGGGGGCTGGACTTCGCCTGTGATATCTACATCTGGGCGCCC

TTGGCCGGGACTTGTGGGGTCCTTCTCCTGTCACTGGTTATCACCCTTTACTGC

AAACGGGGCAGAAAGAAACTCCTGTATATATTCAAACAACCATTTATGAGAC

CAGTACAAACTACTCAAGAGGAAGATGGCTGTAGCTGCCGATTTCCAGAAGA

AGAAGAAGGAGGATGTGAACTGAGAGTGAAGTTCAGCAGGAGCGCAGACGC

CCCCGCGTACAAGCAGGGCCAGAACCAGCTCTATAACGAGCTCAATCTAGGA

CGAAGAGAGGAGTACGATGTTTTGGACAAGAGACGTGGCCGGGACCCTGAG

ATGGGGGGAAAGCCGAGAAGGAAGAACCCTCAGGAAGGCCTGTACAATGAA

CTGCAGAAAGATAAGATGGCGGAGGCCTACAGTGAGATTGGGATGAAAGGC

GAGCGCCGGAGGGGCAAGGGGCACGATGGCCTTTACCAGGGTCTCAGTACA

GCCACCAAGGACACCTACGACGCCCTTCACATGCAGGCCCTGCCCCCTCGCT

AA

Amino acid sequence of PLA2R-CAAR (Construct 4027.CF12; SEQ ID NO: 12)

MLLSPSLLLLLLLGAPRGCAGSEGVAAALTPERLLEWQDKGIFVIQSESLKKCIQA

GKSVLTLENCKQANKHMLWKWVSNHGLFNIGGSGCLGLNFSAPEQPLSLYECD

STLVSLRWRCNRKMITGPLQYSVQVAHDNTVVASRKYIHKWISYGSGGGDICEY

LHKDLHTIKGNTHGMPCMFPFQYNHQWHHECTREGREDDLLWCATTSRYERDE

-continued

KWGFCPDPTSAEVGCDTIWEKDLNSHICYQFNLLSSLSWSEAHSSCQMQGGTLL

SITDETEENFIREHMSSKTVEVWMGLNQLDEHAGWQWSDGTPLNYLNWSPEVN

FEPFVEDHCGTFSSFMPSAWRSRDCESTLPYICKKYLNHIDHEIVEKDAWKYYAT

HCEPGWNPYNRNCYKLQKEEKTWHEALRSCQADNSALIDITSLAEVEFLVTLLG

DENASETWIGLSSNKIPVSFEWSNDSSVIFTNWHTLEPHIFPNRSQLCVSAEQSEG

HWKVKNCEERLFYICKKAGHVLSDAESGCQSGTTTPAPRPPTPAPTIASQPLSLRP

EACRPAAGGAVHTRGLDFACDIYIWAPLAGTCGVLLLSLVITLYCKRGRKKLLYI

FKQPFMRPVQTTQEEDGCSCRFPEEEEGGCELRVKFSRSADAPAYKQGQNQLYN

ELNLGRREEYDVLDKRRGRDPEMGGKPRRKNPQEGLYNELQKDKMAEAYSEIG

MKGERRRGKGHDGLYQGLSTATKDTYDALHMQALPPR

B) Domains comprised in PLA2R-CAAR Construct 4028.CF123
Cysteine-rich (CysR) domain (Ricin B type lectin domain) (SEQ ID NO: 1)
Linker between ricin B type lectin domain and fibronectin type II domain (SEQ ID NO: 2)
Fibronectin type II domain (SEQ ID NO: 3)
Linker between fibronectin type II domain and C-type lectin domain 1 (SEQ ID NO: 4)
C-type lectin 1 domain (SEQ ID NO: 5)
Linker between C-type lectin domain 1 and C-type lectin domain 2 (SEQ ID NO: 6)
C-type lectin domain 2 (SEQ ID NO: 7)
Linker between C-type lectin domain 2 and C-type lectin domain 3

(SEQ ID NO: 13)

AAGGCCGGCCACGTGCTGTCCGATGCCGAGAGTGGATGTCAAGAAGGCTGGG

AGAGA

C-type lectin domain 3

(SEQ ID NO: 14)

CACGGCGGCTTTTGCTACAAGATCGACACCGTGCTGCGGAGCTTCGATCAGG

CCAGCAGCGGCTACTATTGCCCTCCTGCTCTGGTCACCATCACCAACAGATTC

GAGCAGGCCTTCATCACCAGCCTGATCAGCAGCGTCGTGAAGATGAAGGACA

GCTACTTCTGGATCGCCCTGCAGGACCAGAACGACACCGGCGAGTACACATG

GAAGCCCGTGGGACAGAAACCCGAGCCTGTGCAGTACACCCACTGGAACAC

ACACCAGCCTAGATACTCCGGCGGCTGCGTGGCAATGAGAGGCAGACATCCT

CTCGGCAGATGGGAAGTGAAGCACTGTCGGCACTTCAAGGCCATGTCTCTGT

GC

Extracellular domains of PLA2R (SEQ ID NO: 15; See FIG. 2D, Construct 4028.CF123)

AAGGGCATCTTCGTGATCCAGAGCGAGAGCCTGAAGAAGTGCATCCAGGCCG

GCAAGAGCGTGCTGACCCTGGAAAATTGCAAGCAGGCCAACAAGCACATGC

TGTGGAAATGGGTGTCCAACCACGGCCTGTTCAACATCGGCGGCTCTGGATG

TCTGGGCCTGAATTTCTCTGCCCCTGAGCAGCCTCTGAGCCTGTACGAGTGTG

ATAGCACCCTGGTGTCCCTGAGATGGCGGTGCAACCGGAAGATGATCACAGG

CCCTCTGCAGTACTCTGTGCAGGTCGCCCACGACAATACCGTGGTGGCCAGC

AGAAAGTACATCCACAAGTGGATCAGCTACGGCAGCGGCGGAGGCGACATC

TGTGAATACCTGCACAAGGATCTGCACACCATCAAGGGCAACACCCACGGAA

TGCCCTGCATGTTCCCGTTTCAGTACAACCACCAGTGGCACCACGAGTGCACC

AGAGAAGGCAGAGAGGACGACCTGCTTTGGTGCGCCACAACCAGCAGATAC

GAGCGGGATGAGAAGTGGGGCTTCTGCCCTGATCCTACCTCTGCCGAAGTGG

GCTGCGATACCATCTGGGAGAAAGACCTGAACAGCCACATCTGCTACCAGTT

-continued

CAACCTGCTGTCCAGCCTGTCTTGGAGCGAGGCCCACAGCAGCTGTCAAATG

CAAGGCGGCACACTGCTGAGCATCACCGACGAGACAGAGGAAAACTTCATC

CGCGAGCACATGAGCAGCAAGACCGTGGAAGTGTGGATGGGACTGAACCAG

CTGGATGAGCATGCCGGATGGCAGTGGAGTGATGGCACCCCTCTGAACTACC

TGAACTGGTCCCCTGAAGTGAACTTCGAGCCCTTCGTGGAAGATCACTGCGG

CACCTTCAGCAGCTTCATGCCCAGCGCTTGGAGAAGCAGAGACTGCGAGAGC

ACCCTGCCTTACATCTGCAAGAAGTACCTGAACCACATCGACCACGAGATCG

TGGAAAAGGACGCCTGGAAGTACTACGCCACACACTGCGAGCCTGGCTGGA

ACCCCTACAACCGGAACTGCTACAAGCTGCAGAAAGAGGAAAAGACCTGGC

ACGAGGCCCTGAGAAGCTGCCAGGCCGATAATAGCGCCCTGATCGACATCAC

AAGCCTGGCCGAGGTGGAATTTCTGGTCACTCTGCTGGGCGACGAGAACGCC

TCTGAGACATGGATCGGCCTGTCCAGCAACAAGATCCCCGTGTCCTTCGAGT

GGTCCAACGACAGCAGCGTGATCTTCACCAACTGGCACACCCTGGAACCTCA

CATCTTCCCCAACAGATCCCAGCTGTGTGTGTCCGCCGAGCAGTCTGAAGGC

CACTGGAAAGTGAAGAACTGCGAGGAACGGCTGTTCTACATCTGTAAAAAGG

CCGGCCACGTGCTGTCCGATGCCGAGAGTGGATGTCAAGAAGGCTGGGAGAG

ACACGGCGGCTTTTGCTACAAGATCGACACCGTGCTGCGGAGCTTCGATCAG

GCCAGCAGCGGCTACTATTGCCCTCCTGCTCTGGTCACCATCACCAACAGATT

CGAGCAGGCCTTCATCACCAGCCTGATCAGCAGCGTCGTGAAGATGAAGGAC

AGCTACTTCTGGATCGCCCTGCAGGACCAGAACGACACCGGCGAGTACACAT

GGAAGCCCGTGGGACAGAAACCCGAGCCTGTGCAGTACACCCACTGGAACA

CACACCAGCCTAGATACTCCGGCGGCTGCGTGGCAATGAGAGGCAGACATCC

TCTCGGCAGATGGGAAGTGAAGCACTGTCGGCACTTCAAGGCCATGTCTCTG

TGC

Extracellular domains of Construct 4028.CF123

(SEQ ID NO: 71)

KGIFVIQSESLKKCIQAGKSVLTLENCKQANKHMLWKWVSNHGLFNIGGSGCLG

LNFSAPEQPLSLYECDSTLVSLRWRCNRKMITGPLQYSVQVAHDNTVVASRKYI

HKWISYGSGGGDICEYLHKDLHTIKGNTHGMPCMFPFQYNHQWHHECTREGRE

DDLLWCATTSRYERDEKWGFCPDPTSAEVGCDTIWEKDLNSHICYQFNLLSSLS

WSEAHSSCQMQGGTLLSITDETEENFIREHMSSKTVEVWMGLNQLDEHAGWQW

SDGTPLNYLNWSPEVNFEPFVEDHCGTFSSFMPSAWRSRDCESTLPYICKKYLNH

IDHEIVEKDAWKYYATHCEPGWNPYNRNCYKLQKEEKTWHEALRSCQADNSAL

IDITSLAEVEFLVTLLGDENASETWIGLSSNKIPVSFEWSNDSSVIFTNWHTLEPHIF

PNRSQLCVSAEQSEGHWKVKNCEERLFYICKKAGHVLSDAESGCQEGWERHGG

FCYKIDTVLRSFDQASSGYYCPPALVTITNRFEQAFITSLISSVVKMKDSYFWIAL

QDQNDTGEYTWKPVGQKPEPVQYTHWNTHQPRYSGGCVAMRGRHPLGRWEV

KHCRHFKAMSLCKQPVENQEKAEYEERWPFHPCYL

Linker between C-type lectin domain 3 and CD8 hinge (SEQ ID NO: 16)

AAGCAGCCCGTGGAAAATCAAGAGAAGGCCGAGTACGAGGAACGCTGGCCT

TTTCACCCTTGCTACCTGTCCGGA

-continued

CD8 hinge (SEQ ID NO: 10)

Nucleic acid sequence of PLA2R-CAAR
(Construct 4028.CF123; SEQ ID NO: 17)

ATGCTGCTGAGCCCTAGCCTGCTGCTGCTCCTGCTTCTTGGAGCCCCTAGAGG

ATGTGCCGGATCTGAAGGTGTTGCCGCCGCTCTGACACCCGAGAGACTGCTG

GAATGGCAGGACAAGGGCATCTTCGTGATCCAGAGCGAGAGCCTGAAGAAG

TGCATCCAGGCCGGCAAGAGCGTGCTGACCCTGGAAAATTGCAAGCAGGCCA

ACAAGCACATGCTGTGGAAATGGGTGTCCAACCACGGCCTGTTCAACATCGG

CGGCTCTGGATGTCTGGGCCTGAATTTCTCTGCCCCTGAGCAGCCTCTGAGCC

TGTACGAGTGTGATAGCACCCTGGTGTCCCTGAGATGGCGGTGCAACCGGAA

GATGATCACAGGCCCTCTGCAGTACTCTGTGCAGGTCGCCCACGACAATACC

GTGGTGGCCAGCAGAAAGTACATCCACAAGTGGATCAGCTACGGCAGCGGC

GGAGGCGACATCTGTGAATACCTGCACAAGGATCTGCACACCATCAAGGGCA

ACACCCACGGAATGCCCTGCATGTTCCCGTTTCAGTACAACCACCAGTGGCA

CCACGAGTGCACCAGAGAAGGCAGAGAGGACGACCTGCTTTGGTGCGCCAC

AACCAGCAGATACGAGCGGGATGAGAAGTGGGGCTTCTGCCCTGATCCTACC

TCTGCCGAAGTGGGCTGCGATACCATCTGGGAGAAAGACCTGAACAGCCACA

TCTGCTACCAGTTCAACCTGCTGTCCAGCCTGTCTTGGAGCGAGGCCCACAGC

AGCTGTCAAATGCAAGGCGGCACACTGCTGAGCATCACCGACGAGACAGAG

GAAAACTTCATCCGCGAGCACATGAGCAGCAAGACCGTGGAAGTGTGGATG

GGACTGAACCAGCTGGATGAGCATGCCGGATGGCAGTGGAGTGATGGCACCC

CTCTGAACTACCTGAACTGGTCCCCTGAAGTGAACTTCGAGCCCTTCGTGGAA

GATCACTGCGGCACCTTCAGCAGCTTCATGCCCAGCGCTTGGAGAAGCAGAG

ACTGCGAGAGCACCCTGCCTTACATCTGCAAGAAGTACCTGAACCACATCGA

CCACGAGATCGTGGAAAAGGACGCCTGGAAGTACTACGCCACACACTGCGA

GCCTGGCTGGAACCCCTACAACCGGAACTGCTACAAGCTGCAGAAAGAGGA

AAAGACCTGGCACGAGGCCCTGAGAAGCTGCCAGGCCGATAATAGCGCCCT

GATCGACATCACAAGCCTGGCCGAGGTGGAATTTCTGGTCACTCTGCTGGGC

GACGAGAACGCCTCTGAGACATGGATCGGCCTGTCCAGCAACAAGATCCCCG

TGTCCTTCGAGTGGTCCAACGACAGCAGCGTGATCTTCACCAACTGGCACAC

CCTGGAACCTCACATCTTCCCCAACAGATCCCAGCTGTGTGTGTCCGCCGAGC

AGTCTGAAGGCCACTGGAAAGTGAAGAACTGCGAGGAACGGCTGTTCTACAT

CTGTAAAAAGGCCGGCCACGTGCTGTCCGATGCCGAGAGTGGATGTCAAGAA

GGCTGGGAGAGACACGGCGGCTTTTGCTACAAGATCGACACCGTGCTGCGGA

GCTTCGATCAGGCCAGCAGCGGCTACTATTGCCCTCCTGCTCTGGTCACCATC

ACCAACAGATTCGAGCAGGCCTTCATCACCAGCCTGATCAGCAGCGTCGTGA

AGATGAAGGACAGCTACTTCTGGATCGCCCTGCAGGACCAGAACGACACCGG

CGAGTACACATGGAAGCCCGTGGGACAGAAACCCGAGCCTGTGCAGTACAC

CCACTGGAACACACACCAGCCTAGATACTCCGGCGGCTGCGTGGCAATGAGA

GGCAGACATCCTCTCGGCAGATGGGAAGTGAAGCACTGTCGGCACTTCAAGG

CCATGTCTCTGTGCAAGCAGCCCGTGGAAAATCAAGAGAAGGCCGAGTACGA

-continued

GGAACGCTGGCCTTTTCACCCTTGCTACCTGTCCGGAACCACGACGCCAGCG

CCGCGACCACCAACACCGGCGCCCACCATCGCGTCGCAGCCCCTGTCCCTGC

GCCCAGAGGCGTGCCGGCCAGCGGCGGGGGGCGCAGTGCACACGAGGGGGC

TGGACTTCGCCTGTGATATCTACATCTGGGCGCCCTTGGCCGGGACTTGTGGG

GTCCTTCTCCTGTCACTGGTTATCACCCTTTACTGCAAACGGGGCAGAAAGAA

ACTCCTGTATATATTCAAACAACCATTTATGAGACCAGTACAAACTACTCAAG

AGGAAGATGGCTGTAGCTGCCGATTTCCAGAAGAAGAAGAAGGAGGATGTG

AACTGAGAGTGAAGTTCAGCAGGAGCGCAGACGCCCCCGCGTACAAGCAGG

GCCAGAACCAGCTCTATAACGAGCTCAATCTAGGACGAAGAGAGGAGTACG

ATGTTTTGGACAAGAGACGTGGCCGGGACCCTGAGATGGGGGGAAAGCCGA

GAAGGAAGAACCCTCAGGAAGGCCTGTACAATGAACTGCAGAAAGATAAGA

TGGCGGAGGCCTACAGTGAGATTGGGATGAAAGGCGAGCGCCGGAGGGGCA

AGGGGCACGATGGCCTTTACCAGGGTCTCAGTACAGCCACCAAGGACACCTA

CGACGCCCTTCACATGCAGGCCCTGCCCCCTCGCTAA

Amino acid sequence of PLA2R-CAAR (Construct 4028.CF123; SEQ ID NO: 18)

MLLSPSLLLLLLLGAPRGCAGSEGVAAALTPERLLEWQDKGIFVIQSESLKKCIQA

GKSVLTLENCKQANKHMLWKWVSNHGLFNIGGSGCLGLNFSAPEQPLSLYECD

STLVSLRWRCNRKMITGPLQYSVQVAHDNTVVASRKYIHKWISYGSGGGDICEY

LHKDLHTIKGNTHGMPCMFPFQYNHQWHHECTREGREDDLLWCATTSRYERDE

KWGFCPDPTSAEVGCDTIWEKDLNSHICYQFNLLSSLSWSEAHSSCQMQGGTLL

SITDETEENFIREHMSSKTVEVWMGLNQLDEHAGWQWSDGTPLNYLNWSPEVN

FEPFVEDHCGTFSSFMPSAWRSRDCESTLPYICKKYLNHIDHEIVEKDAWKYYAT

HCEPGWNPYNRNCYKLQKEEKTWHEALRSCQADNSALIDITSLAEVEFLVTLLG

DENASETWIGLSSNKIPVSFEWSNDSSVIFTNWHTLEPHIFPNRSQLCVSAEQSEG

HWKVKNCEERLFYICKKAGHVLSDAESGCQEGWERHGGFCYKIDTVLRSFDQA

SSGYYCPPALVTITNRFEQAFITSLISSVVKMKDSYFWIALQDQNDTGEYTWKPV

GQKPEPVQYTHWNTHQPRYSGGCVAMRGRHPLGRWEVKHCRHFKAMSLCKQP

VENQEKAEYEERWPFHPCYLSGTTTPAPRPPTPAPTIASQPLSLRPEACRPAAGGA

VHTRGLDFACDIYIWAPLAGTCGVLLLSLVITLYCKRGRKKLLYIFKQPFMRPVQ

TTQEEDGCSCRFPEEEEGGCELRVKFSRSADAPAYKQGQNQLYNELNLGRREEY

DVLDKRRGRDPEMGGKPRRKNPQEGLYNELQKDKMAEAYSEIGMKGERRRGK

GHDGLYQGLSTATKDTYDALHMQALPPR

Nucleotide sequence of pTRPE.CysR.CD8H.BBz CAAR (Construct C)

(SEQ ID NO: 25)

| | |
|---|---|
| ***IgG Signal peptide*** | 1-57 (SEQ ID NO: 46) |
| <u>CysR</u> | 64-459 (SEQ ID NO: 47) |
| *CD8 Hinge region* | 466-630 (SEQ ID NO: 64) |
| **CD8 TMD** | 631-702 (SEQ ID NO: 20) |

-continued 4-1BB intracellular domain 703-828 (SEQ ID NO: 66)

CD3zeta intracellular domain 829-1164 (SEQ ID NO: 24)

Stop codon 1165-1167

*ATGGAGTTTGGGCTGAGCTGG CTTTTTCTTGTGGCTATTTT AAAAGGTGTCCAG*

*TGC* ggatccAAAGGAATATTTGTCATTCAGTCAGAGTCTTTGAAAAAGTGCATAC

AGGCTGGAAAAAGCGTGCTTACCCTGGAGAACTGCAAGCAAGCTAATAAGC

ATATGCTTTGGAAATGGGTTAGCAACCACGGACTCTTTAATATCGGAGGCTCC

GGCTGTCTGGGCCTGAACTTCAGTGCACCGGAGCAACCGCTTTCTCTGTACGA

ATGTGATAGCACACTTGTTAGTCTTCGGTGGCGGTGTAACCGAAAAATGATT

ACAGGCCCTCTGCAATATAGTGTTCAAGTGGCCCACGACAATACAGTTGTGG

CGTCTAGAAAATATATTCACAAGTGGATTTCCTACGGGAGCGGCGGAGGGGA

TATATGTGAATATCTTCACAAAGACTTGCATACAATCgctagc*TTCGTGCCGGTCT*

*TCCTGCCAGCGAAGCCAACCACGACGCCAGCACCGCGACCACCAACACCTGCGC*

*CCACCATCGCGTCGCAGCCCCTGTCCCTGCGCCCAGAGGCGTGCAGACCAGCAG*

*CGGGGGGCGCAGTGCACACGAGGGGGCTGGACTTCGCCTGTGAT*ATCTACATC

TGGGCGCCCTTGGCCGGGACTTGTGGGGTCCTTCTCCTGTCACTGGTTA

TCACCCTTTACTGCAAGCGCGGTCGCAAGAAACTGCTCTATATTTTTAAACA

GCCATTCATGAGACCTGTCCAGACCACTCAAGAGGAGGACGGATGTTCCTGT

AGATTTCCTGAAGAGGAAGAGGGGGGGTGCGAGCTGAGAGTGAAGTTCAGC

AGGAGCGCAGACGCCCCCGCGTACCAGCAGGGCCAGAACCAGCTCTATAAC

GAGCTCAATCTAGGACGAAGAGAGGAGTACGATGTTTTGGACAAGAGACGT

GGCCGGGACCCTGAGATGGGGGGAAAGCCGAGAAGGAAGAACCCTCAGGAA

GGCCTGTACAATGAACTGCAGAAAGATAAGATGGCGGAGGCCTACAGTGAG

ATTGGGATGAAAGGCGAGCGCCGGAGGGGCAAGGGGCACGATGGCCTTTAC

CAGGGTCTCAGTACAGCCACCAAGGACACCTACGACGCCCTTCACATGCAGG

CCCTGCCCCCTCGCTAA

Amino acid sequence of pTRPE.CysR.CD8H.BBz CAAR (Construct C) (SEQ ID NO: 26)

*IgG Signal peptide* 1-19 (SEQ ID NO: 48)

CysR 22-153 (SEQ ID NO: 49)

*CD8 Hinge region* 156-210 (SEQ ID NO: 44)

CD8 TMD 211-234 (SEQ ID NO: 19)

4-1BB intracellular domain 235-276 (SEQ ID NO: 21)

CD3zeta intracellular domain 277-388 (SEQ ID NO: 45)

*MEFGLSWLFLVAILKGVQC* GSKGIFVIQSESLKKCIQAGKSVLTLENCKQANKH

MLWKWVSNHGLFNIGGSGCLGLNFSAPEQPLSLYECDSTLVSLRWRCNRKMITG

-continued

PLQYSVQVAHDNTVVASRKYIHKWISYGSGGGDICEYLHKDLHTIAS*FVPVFLPA*

*KPTTTPAPRPPTPAPTIASQPLSLRPEACRPAAGGAVHTRGLDFACD*IYIWAPLAGT

CGVLLLSLVITLYCKRGRKKLLYIFKQPFMRPVQTTQEEDGCSCRFPEEEEGGCE

LRVKFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYDAL

HMQALPPR

Nucleotide sequence of pTRPE.CysR-FNII-CTLD1.CD8H.BBz CAAR (construct CF1)

(SEQ ID NO: 27)

| | |
|---|---|
| *IgG Signal peptide* | 1-57 (SEQ ID NO: 46) |
| CysR-FNII-CTLD1 | 64-1053 (SEQ ID NO: 50) |
| *CD8 Hinge region* | 1060-1224 (SEQ ID NO: 64) |
| **CD8 TMD** | 1225-1296 (SEQ ID NO: 20) |
| 4-1BB intracellular domain | 1297-1422 (SEQ ID NO: 66) |
| CD3zeta intracellular domain | 1423-1758 (SEQ ID NO: 24) |
| Stop codon | 1759-1761 |

*ATGGAGTTTGGGCTGAGCTG GCTTTTTCTTGTGGCTATT TTAAAAGGTGTCCAG*

*TGC* ggatccAAAGGGATCTTTGTTATACAAAGTGAGAGCTTGAAAAAATGTATA

CAGGCTGGCAAAAGTGTACTGACTCTTGAAAATTGCAAACAAGCCAACAAAC

ACATGCTGTGGAAATGGGTGTCTAATCACGGTCTCTTCAATATTGGGGGAAG

TGGATGCCTCGGCCTGAATTTCTCCGCTCCCGAACAGCCCCTCTCACTTTATG

AGTGTGATTCAACTCTGGTGTCCTTGAGGTGGCGATGTAACCGCAAGATGAT

AACCGGCCCCCTCCAGTATTCCGTCCAAGTAGCACACGACAATACCGTGGTG

GCATCTAGGAAATACATTCATAAGTGGATATCTTATGGCAGTGGTGGCGGTG

ACATATGCGAGTACCTGCACAAGGACCTCCACACAATAAAGGGGAACACGC

ACGGGATGCCGTGTATGTTCCCGTTCCAATATAATCATCAATGGCACCATGAG

TGTACGAGAGAGGGGCGAGAAGACGACCTCCTGTGGTGTGCGACCACCTCAA

GATATGAACGGGATGAGAAGTGGGGCTTTTGCCCCGACCCAACCTCCGCCGA

GGTTGGTTGCGACACTATTTGGGAAAAAGATTTGAACAGTCATATATGCTATC

AATTTAATTTGTTGAGTTCACTCTCCTGGAGCGAAGCGCACAGCTCTTGTCAG

ATGCAAGGTGGTACATTGCTTAGCATTACTGATGAAACTGAGGAGAATTTCA

TTAGGGAGCATATGTCCTCAAAGACAGTAGAGGTGTGGATGGGTCTGAACCA

GCTCGACGAACACGCCGGTTGGCAGTGGTCAGATGGAACGCCTCTGAATTAT

CTCAACTGGTCCCCTGAGGTCAACTTTGAACCGTTTGTGGAAGATCATTGTGG

TACTTTTTCCAGTTTTATGCCAAGCGCCTGGCGAAGCCGAGACTGCGAGTCTA

CGTTGCCCTATATCTGCAAGAAGTATTTGAATCACATAGATCATGAAATTGTT

GAAgctagc*TTCGTGCCGGTCTTCCTGCCAGCGAAGCCAACCACGACGCCAGCACC*

*GCGACCACCAACACCTGCGCCCACCATCGCGTCGCAGCCCCTGTCCCTGCGCCC*

*AGAGGCGTGCAGACCAGCAGCGGGGGGCGCAGTGCACACGAGGGGGCTGGACT*

*TCGCCTGTGAT*ATCTACATCTGGGCGCCCTTGGCCGGGACTTGTGGGGTC

-continued

CTTCTCCTGTCACTGGTTATCACCCTTTACTGCAAGCGCGGTCGCAAGAA

ACTGCTCTATATTTTTAAACAGCCATTCATGAGACCTGTCCAGACCACTCAAG

AGGAGGACGGATGTTCCTGTAGATTTCCTGAAGAGGAAGAGGGGGGGTGCG

AGCTGAGAGTGAAGTTCAGCAGGAGCGCAGACGCCCCCGCGTACCAGCAGG

GCCAGAACCAGCTCTATAACGAGCTCAATCTAGGACGAAGAGAGGAGTACG

ATGTTTTGGACAAGAGACGTGGCCGGGACCCTGAGATGGGGGGAAAGCCGA

GAAGGAAGAACCCTCAGGAAGGCCTGTACAATGAACTGCAGAAAGATAAGA

TGGCGGAGGCCTACAGTGAGATTGGGATGAAAGGCGAGCGCCGGAGGGGCA

AGGGGCACGATGGCCTTTACCAGGGTCTCAGTACAGCCACCAAGGACACCTA

CGACGCCCTTCACATGCAGGCCCTGCCCCCTCGCTAA

Amino acid sequence of pTRPE.CysR-FNII-CTLD1.CD8H.BBz CAAR (construct CF1)

(SEQ ID NO: 28)

| | |
|---|---|
| *IgG Signal peptide* | 1-19 (SEQ ID NO: 48) |
| CysR-FNII-CTLD1 | 22-351 (SEQ ID NO: 51) |
| *CD8 Hinge region* | 354-408 (SEQ ID NO: 43) |
| **CD8 TMD** | 409-432 (SEQ ID NO: 19) |
| 4-1BB intracellular domain | 433-474 (SEQ ID NO: 21) |
| CD3zeta intracellular domain | 475-586 (SEQ ID NO: 45) |

*MEFGLSWLFLVAILKGVQC*GSKGIFVIQSESLKKCIQAGKSVLTLENCKQANKHML

WKWVSNHGLFNIGGSGCLGLNFSAPEQPLSLYECDSTLVSLRWRCNRKMITGPL

QYSVQVAHDNTVVASRKYIHKWISYGSGGGDICEYLHKDLHTIKGNTHGMPCM

FPFQYNHQWHHECTREGREDDLLWCATTSRYERDEKWGFCPDPTSAEVGCDTI

WEKDLNSHICYQFNLLSSLSWSEAHSSCQMQGGTLLSITDETEENFIREHMSSKT

VEVWMGLNQLDEHAGWQWSDGTPLNYLNWSPEVNFEPFVEDHCGTFSSFMPS

AWRSRDCESTLPYICKKYLNHIDHEIVEAS*FVPVFLPAKPTTTPAPRPPTPAPTIASQ*

*PLSLRPEACRPAAGGAVHTRGLDFACD*IYIWAPLAGTCGVLLLSLVITLYCKRGR

KKLLYIFKQPFMRPVQTTQEEDGCSCRFPEEEEGGCELRVKFSRSADAPAYQQGQ

NQLYNELNLGRREEYDVLDKRRGRDPEMGGKPRRKNPQEGLYNELQKDKMAE

AYSEIGMKGERRRGKGHDGLYQGLSTATKDTYDALHMQALPPR

Nucleotide sequence of pTRPE.CysR-FNII-CTLD1-3.GS linker.BBz CAAR (construct CF123)

(SEQ ID NO: 29)

| | |
|---|---|
| ***IgG Signal peptide*** | 1-57 (SEQ ID NO: 46) |
| CysR-FNII-CTLD1-3 | 64-1911 (SEQ ID NO: 52) |
| *GS linker* | 1918-1947 (SEQ ID NO: 68) |
| **CD8 TMD** | 1954-2025 (SEQ ID NO: 20) |

-continued

| | |
|---|---|
| 4-1BB intracellular domain | 2026-2151 (SEQ ID NO: 66) |
| CD3zeta intracellular domain | 2152-2487 (SEQ ID NO: 24) |
| Stop codon | 2488-2490 |

*ATGGAGTTTGGGCTGAGCTGG CTTTTTCTTGTGGCTA TTTTAAAAGGTGTCCAG*

*TGC* ggatccAAAGGGATTTTCGTGATACAGTCCGAGAGTCTCAAAAAGTGTATC

CAGGCAGGCAAAAGTGTTCTCACTCTGGAAAACTGCAAACAAGCGAACAAG

CACATGTTGTGGAAGTGGGTTAGTAACCATGGACTGTTCAACATCGGAGGTA

GTGGATGCCTTGGTCTCAATTTCTCTGCTCCGGAACAGCCTTTGTCACTGTAC

GAATGCGACTCCACTCTCGTTAGTCTTAGATGGCGATGCAATCGCAAAATGA

TTACGGGACCACTTCAATATTCAGTTCAAGTGGCACATGATAACACCGTAGT

GGCCTCACGGAAATACATCCATAAATGGATTTCTTATGGTAGCGGGGGCGGC

GATATATGTGAATACCTCCATAAGGATCTCCACACCATTAAGGGTAATACTC

ACGGTATGCCGTGTATGTTTCCTTTTCAGTACAATCATCAGTGGCATCATGAA

TGCACGAGGGAAGGACGCGAGGACGATTTGCTCTGGTGCGCAACCACCTCAC

GCTACGAGAGAGACGAAAAATGGGGCTTTTGCCCGGACCCCACTAGTGCTGA

GGTAGGATGTGATACGATTTGGGAAAAGGATTTGAATTCTCATATTTGCTACC

AGTTTAATCTTCTTTCATCCCTGTCCTGGTCTGAGGCTCATTCTAGTTGCCAGA

TGCAAGGTGGGACTTTGCTTTCAATTACTGACGAGACTGAGGAAAATTTTATC

CGAGAGCATATGTCTTCTAAAACCGTAGAGGTATGGATGGGCCTGAACCAAT

TGGACGAACACGCGGGCTGGCAGTGGAGCGACGGGACACCTCTCAACTACCT

TAATTGGAGCCCTGAGGTAAACTTTGAACCGTTTGTCGAGGATCACTGCGGA

ACTTTCAGCAGCTTCATGCCTAGTGCATGGCGGTCCCGAGACTGTGAGAGCA

CCCTTCCATACATATGTAAAAAATACCTCAATCACATAGACCACGAGATCGT

AGAGAAGGATGCATGGAAATATTATGCTACGCACTGTGAGCCGGGATGGAAT

CCTTATAACCGCAACTGTTACAAGCTGCAAAAAGAAGAGAAGACATGGCATG

AGGCGCTGCGCTCATGTCAAGCGGACAATTCTGCACTTATAGATATAACTAG

TTTGGCGGAGGTAGAATTTTTGGTTACGCTTCTCGGCGATGAGAATGCGTCCG

AGACGTGGATAGGGTTGTCAAGCAATAAAATTCCTGTAAGTTTTGAATGGTC

AAATGACTCTTCTGTCATCTTCACCAATTGGCACACACTCGAACCCCATATCT

TCCCAAACCGAAGCCAGTTGTGTGTCAGCGCTGAGCAATCAGAAGGACATTG

GAAAGTTAAAAACTGTGAAGAAAGACTGTTCTACATCTGTAAGAAGGCAGGA

CATGTGCTTTCAGATGCGGAAAGCGGCTGTCAAGAAGGTTGGGAGCGCCATG

GAGGTTTCTGTTATAAAATCGACACAGTTTTGCGATCTTTCGATCAGGCTTCA

AGCGGGTACTATTGTCCTCCTGCACTGGTTACAATCACGAACCGGTTTGAACA

GGCTTTTATAACTTCTTTGATTTCCAGCGTGGTTAAAATGAAGGACTCTTATTT

CTGGATAGCCCTGCAAGACCAAAATGATACCGGTGAGTACACATGGAAACCG

GTAGGTCAAAAGCCAGAGCCAGTCCAGTACACTCATTGGAATACCCACCAGC

CTAGGTACTCCGGCGGGTGTGTGGCGATGCGGGGTCGCCACCCTCTCGGACG

CTGGGAGGTGAAGCATTGCCGCCACTTCAAGGCGATGAGCTTGTGTAAACAG

CCCGTCGAAAATCAGGAAAAGGCAgctagc*GGTGGCGGAGGTTCTGGAGGTGGA*

-continued

*GGTTCC*tccggaATCTACATCTGGGCGCCCTTGGCCGGGACTTGTGGGGTCC
TTCTCCTGTCACTGGTTATCACCCTTTACTGCAAGCGCGGTCGCAAGAAAC
TGCTCTATATTTTTAAACAGCCATTCATGAGACCTGTCCAGACCACTCAAGAG
GAGGACGGATGTTCCTGTAGATTTCCTGAAGAGGAAGAGGGGGGGTGCGAG
CTGAGAGTGAAGTTCAGCAGGAGCGCAGACGCCCCCGCGTACCAGCAGGGC

CAGAACCAGCTCTATAACGAGCTCAATCTAGGACGAAGAGAGGAGTACGAT

GTTTTGGACAAGAGACGTGGCCGGGACCCTGAGATGGGGGGAAAGCCGAGA

AGGAAGAACCCTCAGGAAGGCCTGTACAATGAACTGCAGAAAGATAAGATG

GCGGAGGCCTACAGTGAGATTGGGATGAAAGGCGAGCGCCGGAGGGGCAAG

GGGCACGATGGCCTTTACCAGGGTCTCAGTACAGCCACCAAGGACACCTACG

ACGCCCTTCACATGCAGGCCCTGCCCCCTCGCTAA

Amino acid sequence of pTRPE.CysR-FNII-CTLD1-3.GS linker.BBz CAAR
(construct CF123)
(SEQ ID NO: 30)

| | |
|---|---|
| *IgG Signal peptide* | 1-19 (SEQ ID NO: 48) |
| CysR-FNII-CTLD1-3 | 22-637 (SEQ ID NO: 53) |
| *GS linker* | 640-649 (SEQ ID NO: 69) |
| **CD8 TMD** | 652-675 (SEQ ID NO: 19) |
| 4-1BB intracellular domain | 676-717 (SEQ ID NO: 21) |
| CD3zeta intracellular domain | 718-829 (SEQ ID NO: 45) |

*MEFGLSWLFLVAILKGVQC* GSKGIFVIQSESLKKCIQAGKSVLTLENCKQANKH
MLWKWVSNHGLFNIGGSGCLGLNFSAPEQPLSLYECDSTLVSLRWRCNRKMITG
PLQYSVQVAHDNTVVASRKYIHKWISYGSGGGDICEYLHKDLHTIKGNTHGMPC
MFPFQYNHQWHHECTREGREDDLLWCATTSRYERDEKWGFCPDPTSAEVGCDT
IWEKDLNSHICYQFNLLSSLSWSEAHSSCQMQGGTLLSITDETEENFIREHMSSKT
VEVWMGLNQLDEHAGWQWSDGTPLNYLNWSPEVNFEPFVEDHCGTFSSFMPS
AWRSRDCESTLPYICKKYLNHIDHEIVEKDAWKYYATHCEPGWNPYNRNCYKL
QKEEKTWHEALRSCQADNSALIDITSLAEVEFLVTLLGDENASETWIGLSSNKIPV
SFEWSNDSSVIFTNWHTLEPHIFPNRSQLCVSAEQSEGHWKVKNCEERLFYICKK
AGHVLSDAESGCQEGWERHGGFCYKIDTVLRSFDQASSGYYCPPALVTITNRFE
QAFITSLISSVVKMKDSYFWIALQDQNDTGEYTWKPVGQKPEPVQYTHWNTHQP
RYSGGCVAMRGRHPLGRWEVKHCRHFKAMSLCKQPVENQEKAAS*GGGGSGGG*
*GSSG*IYIWAPLAGTCGVLLLSLVITLYCKRGRKKLLYIFKQPFMRPVQTTQEED
GCSCRFPEEEEGGCELRVKFSRSADAPAYQQGQNQLYNELNLGRREEYDVLDKR
RGRDPEMGGKPRRKNPQEGLYNELQKDKMAEAYSEIGMKGERRRGKGHDGLY
QGLSTATKDTYDALHMQALPPR

-continued

Nucleotide sequence of pTRPE.CysR-FNII-CTLD1-3 7.GS linker.BBz CAAR (construct CF1237)

(SEQ ID NO: 31)

*IgG Signal peptide* 1-57 (SEQ ID NO: 46)

CysR-FNII-CTLD1-3 7 64-2331 (SEQ ID NO: 54)

*GS linker* 2338-2367 (SEQ ID NO: 68)

CD8 TMD 2374-2445 (SEQ ID NO: 20)

4-1BB intracellular domain 2446-2571 (SEQ ID NO: 66)

CD3zeta intracellular domain 2572-2907 (SEQ ID NO: 24)

Stop codon 2908-2910

*ATGGAGTTTGGGCTGAGCTG GCTTTTTCTTGTGGCTATT TTAAAAGGTGTCCAG*

*TGC* ggatccAAAGGGATTTTCGTGATACAGTCCGAGAGTCTCAAAAAGTGTATC

CAGGCAGGCAAAAGTGTTCTCACTCTGGAAAACTGCAAACAAGCGAACAAG

CACATGTTGTGGAAGTGGGTTAGTAACCATGGACTGTTCAACATCGGAGGTA

GTGGATGCCTTGGTCTCAATTTCTCTGCTCCGGAACAGCCTTTGTCACTGTAC

GAATGCGACTCCACTCTCGTTAGTCTTAGATGGCGATGCAATCGCAAAATGA

TTACGGGACCACTTCAATATTCAGTTCAAGTGGCACATGATAACACCGTAGT

GGCCTCACGGAAATACATCCATAAATGGATTTCTTATGGTAGCGGGGGCGGC

GATATATGTGAATACCTCCATAAGGATCTCCACACCATTAAGGGTAATACTC

ACGGTATGCCGTGTATGTTTCCTTTTCAGTACAATCATCAGTGGCATCATGAA

TGCACGAGGGAAGGACGCGAGGACGATTTGCTCTGGTGCGCAACCACCTCAC

GCTACGAGAGAGACGAAAAATGGGGCTTTTGCCCGGACCCCACTAGTGCTGA

GGTAGGATGTGATACGATTTGGGAAAAGGATTTGAATTCTCATATTTGCTACC

AGTTTAATCTTCTTTCATCCCTGTCCTGGTCTGAGGCTCATTCTAGTTGCCAGA

TGCAAGGTGGGACTTTGCTTTCAATTACTGACGAGACTGAGGAAAATTTTATC

CGAGAGCATATGTCTTCTAAAACCGTAGAGGTATGGATGGGCCTGAACCAAT

TGGACGAACACGCGGGCTGGCAGTGGAGCGACGGGACACCTCTCAACTACCT

TAATTGGAGCCCTGAGGTAAACTTTGAACCGTTTGTCGAGGATCACTGCGGA

ACTTTCAGCAGCTTCATGCCTAGTGCATGGCGGTCCCGAGACTGTGAGAGCA

CCCTTCCATACATATGTAAAAAATACCTCAATCACATAGACCACGAGATCGT

AGAGAAGGATGCATGGAAATATTATGCTACGCACTGTGAGCCGGGATGGAAT

CCTTATAACCGCAACTGTTACAAGCTGCAAAAAGAAGAGAAGACATGGCATG

AGGCGCTGCGCTCATGTCAAGCGGACAATTCTGCACTTATAGATATAACTAG

TTTGGCGGAGGTAGAATTTTTGGTTACGCTTCTCGGCGATGAGAATGCGTCCG

AGACGTGGATAGGGTTGTCAAGCAATAAAATTCCTGTAAGTTTTGAATGGTC

AAATGACTCTTCTGTCATCTTCACCAATTGGCACACACTCGAACCCCATATCT

TCCCAAACCGAAGCCAGTTGTGTGTCAGCGCTGAGCAATCAGAAGGACATTG

GAAAGTTAAAAACTGTGAAGAAAGACTGTTCTACATCTGTAAGAAGGCAGGA

CATGTGCTTTCAGATGCGGAAAGCGGCTGTCAAGAAGGTTGGGAGCGCCATG

GAGGTTTCTGTTATAAAATCGACACAGTTTTGCGATCTTTCGATCAGGCTTCA

AGCGGGTACTATTGTCCTCCTGCACTGGTTACAATCACGAACCGGTTTGAACA

-continued

GGCTTTTATAACTTCTTTGATTTCCAGCGTGGTTAAAATGAAGGACTCTTATTT

CTGGATAGCCCTGCAAGACCAAAATGATACCGGTGAGTACACATGGAAACCG

GTAGGTCAAAAGCCAGAGCCAGTCCAGTACACTCATTGGAATACCCACCAGC

CTAGGTACTCCGGCGGGTGTGTGGCGATGCGGGGTCGCCACCCTCTCGGACG

CTGGGAGGTGAAGCATTGCCGCCACTTCAAGGCGATGAGCTTGTGTAAACAG

CCCGTCGAAAATCAGGAAAAGGCAGTTAACACATCTGATATGTACCCTATGC

CTAACACACTCGAATATGGGAATAGGACGTACAAGATTATAAACGCGAACAT

GACGTGGTATGCTGCAATCAAGACGTGCCTCATGCACAAAGCTCAGCTTGTG

TCTATTACTGACCAATACCACCAATCATTTTTGACAGTCGTGTTGAATCGATT

GGGGTACGCCCATTGGATCGGTCTCTTCACGACGGACAATGGGCTCAATTTTG

ACTGGAGTGACGGTACTAAATCATCCTTTACTTTTTGGAAGGATGAAGAAAG

TTCTCTGTTGGGCGATTGCGTGTTTGCTGACTCAAATGGCCGATGGCATTCCA

CAGCCTGTGAAAGTTTTCTGCAGGGAGCTATTTGCCACGTGCCTCCCGAAACG

CGGCAGTCCGAACACCCGGAATTGgctagc*GGTGGCGGAGGTTCTGGAGGTGGAG*

*GTTCC*tccggaATCTACATCTGGGCGCCCTTGGCCGGGACTTGTGGGGTCCT

TCTCCTGTCACTGGTTATCACCCTTTACTGCAAGCGCGGTCGCAAGAAACT

GCTCTATATTTTTAAACAGCCATTCATGAGACCTGTCCAGACCACTCAAGAGG

AGGACGGATGTTCCTGTAGATTTCCTGAAGAGGAAGAGGGGGGGTGCGAGCT

GAGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATGTT

TTGGACAAGAGACGTGGCCGGGACCCTGAGATGGGGGGAAAGCCGAGAAGG

AAGAACCCTCAGGAAGGCCTGTACAATGAACTGCAGAAAGATAAGATGGCG

GAGGCCTACAGTGAGATTGGGATGAAAGGCGAGCGCCGGAGGGGCAAGGGG

CACGATGGCCTTTACCAGGGTCTCAGTACAGCCACCAAGGACACCTACGACG

CCCTTCACATGCAGGCCCTGCCCCCTCGCTAA

Amino acid sequence of pTRPE.CysR-FNII-CTLD1-3 7.GS linker.BBz CAAR (construct CF1237)

(SEQ ID NO: 32)

| | |
|---|---|
| ***IgG Signal peptide*** | 1-19 (SEQ ID NO: 48) |
| CysR-FNII-CTLD1-3 7 | 22-777 (SEQ ID NO: 55) |
| *GS linker* | 780-789 (SEQ ID NO: 69) |
| **CD8 TMD** | 792-815 (SEQ ID NO: 19) |
| 4-1BB intracellular domain | 816-857 (SEQ ID NO: 21) |
| CD3zeta intracellular domain | 858-969 (SEQ ID NO: 45) |

*MEFGLSWLFLVAILKGVQC* GSKGIFVIQSESLKKCIQAGKSVLTLENCKQANKH

MLWKWVSNHGLFNIGGSGCLGLNFSAPEQPLSLYECDSTLVSLRWRCNRKMITG

PLQYSVQVAHDNTVVASRKYIHKWISYGSGGDICEYLHKDLHTIKGNTHGMPC

MFPFQYNHQWHHECTREGREDDLLWCATTSRYERDEKWGFCPDPTSAEVGCDT

-continued

IWEKDLNSHICYQFNLLSSLSWSEAHSSCQMQGGTLLSITDETEENFIREHMSSKT

VEVWMGLNQLDEHAGWQWSDGTPLNYLNWSPEVNFEPFVEDHCGTFSSFMPS

AWRSRDCESTLPYICKKYLNHIDHEIVEKDAWKYYATHCEPGWNPYNRNCYKL

QKEEKTWHEALRSCQADNSALIDITSLAEVEFLVTLLGDENASETWIGLSSNKIPV

SFEWSNDSSVIFTNWHTLEPHIFPNRSQLCVSAEQSEGHWKVKNCEERLFYICKK

AGHVLSDAESGCQEGWERHGGFCYKIDTVLRSFDQASSGYYCPPALVTITNRFE

QAFITSLISSVVKMKDSYFWIALQDQNDTGEYTWKPVGQKPEPVQYTHWNTHQP

RYSGGCVAMRGRHPLGRWEVKHCRHFKAMSLCKQPVENQEKAVNTSDMYPM

PNTLEYGNRTYKIINANMTWYAAIKTCLMHKAQLVSITDQYHQSFLTVVLNRLG

YAHWIGLFTTDNGLNFDWSDGTKSSFTFWKDEESSLLGDCVFADSNGRWHSTA

CESFLQGAICHVPPETRQSEHPELA*SGGGGSGGGGSS*GIYIWAPLAGTCGVLLLS

LVITLYCKRGRKKLLYIFKQPFMRPVQTTQEEDGCSCRFPEEEEGGCELRVKFSR

SADAPAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQALP

PR

Nucleotide sequence of pTRPE.CysR-FNII-CTLD1 7.GS linker.BBz CAAR
(construct CF17)

(SEQ ID NO: 33)

| | |
|---|---|
| ***IgG Signal peptide*** | 1-57 (SEQ ID NO: 46) |
| CysR-FNII-CTLD1 7 | 64-1473 (SEQ ID NO: 56) |
| *GS linker* | 1480-1509 (SEQ ID NO: 68) |
| **CD8 TMD** | 1516-1587 (SEQ ID NO: 20) |
| 4-1BB intracellular domain | 1588-1713 (SEQ ID NO: 66) |
| CD3zeta intracellular domain | 1714-2049 (SEQ ID NO: 24) |
| Stop codon | 2050-2052 |

*ATGGAGTTTGGGCTGAGCTGG CTTTTTCTTGTGGCTATTTT AAAAGGTGTCCAG*

*TGC* ggatccAAAGGCATCTTCGTAATCCAGTCAGAAAGTTTGAAAAAATGTATC

CAAGCTGGCAAATCAGTACTTACCCTTGAGAACTGCAAGCAAGCCAATAAAC

ATATGCTGTGGAAATGGGTCTCAAACCACGGCCTCTTCAATATTGGTGGGTCA

GGTTGCTTGGGGTTGAATTTCTCCGCCCCAGAGCAACCACTCAGCCTTTACGA

GTGTGATTCCACACTTGTCTCTTTGCGATGGCGCTGCAATAGGAAAATGATCA

CAGGCCCCCTTCAGTACTCTGTGCAAGTTGCTCATGATAACACAGTCGTGGCG

AGTCGGAAATATATTCACAAATGGATTTCTTATGGGAGTGGTGGAGGAGATA

TATGCGAGTATTTGCATAAGGACTTGCACACCATCAAGGGAAACACTCACGG

TATGCCATGTATGTTTCCGTTCCAATATAATCATCAATGGCACCACGAATGTA

CCCGAGAGGGACGCGAGGACGATCTTCTTTGGTGCGCCACAACCTCTCGATA

TGAACGAGATGAGAAGTGGGGGTTTTGTCCTGACCCAACCAGTGCAGAAGTA

GGGTGCGATACCATCTGGGAGAAAGACTTGAACTCACACATATGCTATCAGT

TTAATTTGTTGTCTTCTTTGTCATGGAGCGAAGCTCATTCATCATGCCAGATG

CAGGGCGGGACACTGCTTTCTATCACCGACGAGACTGAGGAAAATTTTATCC

-continued

```
GCGAGCACATGTCAAGCAAGACAGTTGAGGTTTGGATGGGGCTCAATCAACT

GGACGAACACGCAGGGTGGCAGTGGTCCGATGGCACTCCGCTCAACTACCTT

AACTGGAGCCCAGAGGTGAACTTTGAGCCGTTTGTCGAAGATCACTGTGGTA

CTTTTAGCTCCTTCATGCCGTCCGCATGGAGAAGTCGCGACTGCGAGTCAACC

CTCCCTTACATCTGTAAGAAATACCTCAACCACATAGATCACGAAATCGTAG

AGGTCAATACGTCCGACATGTACCCAATGCCAAATACGTTGGAATATGGGAA

TAGGACATACAAGATAATTAACGCAAATATGACGTGGTATGCCGCAATCAAA

ACGTGCCTCATGCACAAGGCACAGCTCGTGTCAATTACGGACCAGTACCACC

AATCATTTCTCACAGTCGTTCTTAATCGATTGGGTTATGCACACTGGATAGGC

TTGTTCACGACGGACAATGGTTTGAACTTTGACTGGTCCGATGGAACTAAAA

GTTCTTTCACTTTTTGGAAGGATGAGGAGTCCTCCTTGCTCGGGGACTGCGTC

TTCGCAGATTCAAACGGGCGCTGGCACTCAACGGCATGTGAGTCCTTCCTGC

AGGGAGCTATATGCCATGTGCCACCAGAAACACGCCAGTCTGAGCACCCTGA

GTTGgctagcGGTGGCGGAGGTTCTGGAGGTGGAGGTTCCtccggaATCTACATCTG

GGCGCCCTTGGCCGGGACTTGTGGGGTCCTTCTCCTGTCACTGGTTATC

ACCCTTTACTGCAAGCGCGGTCGCAAGAAACTGCTCTATATTTTTAAACAGC

CATTCATGAGACCTGTCCAGACCACTCAAGAGGAGGACGGATGTTCCTGTAG

ATTTCCTGAAGAGGAAGAGGGGGGGTGCGAGCTGAGAGTGAAGTTCAGCAG

GAGCGCAGACGCCCCCGCGTACCAGCAGGGCCAGAACCAGCTCTATAACGA

GCTCAATCTAGGACGAAGAGAGGAGTACGATGTTTTGGACAAGAGACGTGGC

CGGGACCCTGAGATGGGGGGAAAGCCGAGAAGGAAGAACCCTCAGGAAGGC

CTGTACAATGAACTGCAGAAAGATAAGATGGCGGAGGCCTACAGTGAGATTG

GGATGAAAGGCGAGCGCCGGAGGGGCAAGGGGCACGATGGCCTTTACCAGG

GTCTCAGTACAGCCACCAAGGACACCTACGACGCCCTTCACATGCAGGCCCT

GCCCCCTCGCTAA
```

Amino acid sequence of pTRPE.CysR-FNII-CTLD1_7.GS linker.BBz CAAR (construct CF17)

(SEQ ID NO: 34)

| | |
|---|---|
| **IgG Signal peptide** | 1-19 (SEQ ID NO: 48) |
| CysR-FNII-CTLD1_7 | 22-491 (SEQ ID NO: 57) |
| *GS linker* | 494-503 (SEQ ID NO: 69) |
| **CD8 TMD** | 506-529 (SEQ ID NO: 19) |
| 4-1BB intracellular domain | 530-571 (SEQ ID NO: 21) |
| CD3zeta intracellular domain | 572-683 (SEQ ID NO: 45) |

*MEFGLSWLFLVAILKGVQC* GSKGIFVIQSESLKKCIQAGKSVLTLENCKQANKH

MLWKWVSNHGLFNIGGSGCLGLNFSAPEQPLSLYECDSTLVSLRWRCNRKMITG

PLQYSVQVAHDNTVVASRKYIHKWISYGSGGGDICEYLHKDLHTIKGNTHGMPC

MFPFQYNHQWHHECTREGREDDLLWCATTSRYERDEKWGFCPDPTSAEVGCDT

-continued

IWEKDLNSHICYQFNLLSSLSWSEAHSSCQMQGGTLLSITDETEENFIREHMSSKT

VEVWMGLNQLDEHAGWQWSDGTPLNYLNWSPEVNFEPFVEDHCGTFSSFMPS

AWRSRDCESTLPYICKKYLNHIDHEIVEVNTSDMYPMPNTLEYGNRTYKIINANM

TWYAAIKTCLMHKAQLVSITDQYHQSFLTVVLNRLGYAHWIGLFTTDNGLNFD

WSDGTKSSFTFWKDEESSLLGDCVFADSNGRWHSTACESFLQGAICHVPPETRQ

SEHPELAS*GGGGSGGGGSS*GIYIWAPLAGTCGVLLLSLVITLYCKRGRKKLLYI

FKQPFMRPVQTTQEEDGCSCRFPEEEEGGCELRVKFSRSADAPAYQQGQNQLYN

ELNLGRREEYDVLDKRRGRDPEMGGKPRRKNPQEGLYNELQKDKMAEAYSEIG

MKGERRRGKGHDGLYQGLSTATKDTYDALHMQALPPR

Nucleotide sequence of pTRPE.CysR-CTLD1 7.GS linker.BBz CAAR (construct C17)

(SEQ ID NO: 35)

| | |
|---|---|
| ***IgG Signal peptide*** | 1-57 (SEQ ID NO: 46) |
| CysR-FNII-CTLD1 7 | 64-1314 (SEQ ID NO: 58) |
| *GS linker* | 1321-1350 (SEQ ID NO: 68) |
| **CD8 TMD** | 1357-1428 (SEQ ID NO: 20) |
| 4-1BB intracellular domain | 1429-1554 (SEQ ID NO: 66) |
| CD3zeta intracellular domain | 1555-1890 (SEQ ID NO: 24) |
| Stop codon | 1891-1893 |

*ATGGAGTTTGGGCTGAGCTGG CTTTTTCTTGTGGCTA TTTTAAAAGGTGTCCAG*

*TGC* ggatccAAAGGAATCTTCGTAATTCAATCTGAGAGTCTGAAAAAATGTATTC

AGGCCGGTAAGAGCGTACTCACGCTTGAAAATTGCAAACAGGCCAACAAAC

ACATGCTTTGGAAATGGGTTTCAAATCACGGGTTGTTTAACATAGGGGGATC

AGGATGTCTGGGCCTTAACTTTTCCGCACCTGAACAACCTCTTAGTCTGTATG

AGTGTGACTCAACGCTGGTCTCCTTGCGCTGGAGATGCAATCGGAAGATGAT

AACCGGGCCCCTCCAGTATTCCGTTCAGGTCGCCCACGATAATACTGTTGTTG

CATCCCGAAAATATATTCATAAGTGGATCTCCTACGGGAGTGGAGGGGGGCGA

TATTTGTGAATACCTCCACAAGGATCTGCACACTATCACTTCTGCGGAAGTAG

GCTGTGACACAATCTGGGAGAAAGATCTGAATTCACACATTTGCTATCAGTTC

AATCTTCTGAGTTCTTTGAGCTGGTCCGAAGCACATTCATCCTGTCAGATGCA

AGGTGGAACACTCTTGTCAATAACAGATGAAACGGAAGAGAACTTTATTAGA

GAACATATGTCCTCAAAGACTGTGGAGGTGTGGATGGGACTTAACCAGCTCG

ATGAACATGCAGGATGGCAGTGGAGTGACGGAACGCCACTGAACTACCTGA

ATTGGAGCCCAGAGGTGAATTTCGAGCCTTTCGTAGAGGACCATTGCGGTAC

TTTTTCATCTTTTATGCCCAGCGCATGGAGATCCCGAGATTGTGAAAGCACGC

TGCCCTATATTTGTAAAAAGTACCTGAACCACATAGATCATGAGATAGTTGA

GGTAAATACAAGTGATATGTACCCCATGCCGAACACACTCGAGTACGGAAAT

AGAACCTACAAGATAATCAACGCTAACATGACCTGGTACGCGGCCATTAAGA

CCTGCCTCATGCACAAGGCTCAACTCGTCAGTATTACTGACCAATATCACCAG

TCATTTCTCACCGTCGTGTTGAATCGCCTCGGTTACGCCCACTGGATCGGTTT

-continued

GTTTACAACGGACAATGGACTCAATTTCGATTGGTCAGACGGAACCAAATCT

AGTTTTACCTTCTGGAAAGACGAGGAATCAAGCCTGCTTGGGGACTGCGTAT

TTGCGGACTCTAATGGCCGATGGCATAGTACAGCGTGTGAGAGCTTTTTGCA

GGGGGCGATTTGTCATGTTCCGCCGGAAACCCGCCAAAGCGAGCATCCAGAA

TTGgctagc*GGTGGCGGAGGTTCTGGAGGTGGAGGTTCC*tccggaATCTACATCTGG

GCGCCCTTGGCCGGGACTTGTGGGGTCCTTCTCCTGTCACTGGTTATCA

CCCTTTACTGCAAGCGCGGTCGCAAGAAACTGCTCTATATTTTTAAACAGCC

ATTCATGAGACCTGTCCAGACCACTCAAGAGGAGGACGGATGTTCCTGTAGA

TTTCCTGAAGAGGAAGAGGGGGGGTGCGAGCTGAGAGTGAAGTTCAGCAGG

AGCGCAGACGCCCCCGCGTACCAGCAGGGCCAGAACCAGCTCTATAACGAG

CTCAATCTAGGACGAAGAGAGGAGTACGATGTTTTGGACAAGAGACGTGGCC

GGGACCCTGAGATGGGGGGAAAGCCGAGAAGGAAGAACCCTCAGGAAGGCC

TGTACAATGAACTGCAGAAAGATAAGATGGCGGAGGCCTACAGTGAGATTG

GGATGAAAGGCGAGCGCCGGAGGGGCAAGGGGCACGATGGCCTTTACCAGG

GTCTCAGTACAGCCACCAAGGACACCTACGACGCCCTTCACATGCAGGCCCT

GCCCCCTCGCTAA

Amino acid sequence of pTRPE.CysR-CTLD1 7.GS linker.BBz CAAR (construct C17)

(SEQ ID NO: 36)

| | |
|---|---|
| ***IgG Signal peptide*** | 1-19 (SEQ ID NO: 48) |
| CysR-CTLD1 7 | 22-438 (SEQ ID NO: 59) |
| *GS linker* | 441-450 (SEQ ID NO: 69) |
| **CD8 TMD** | 453-476 (SEQ ID NO: 19) |
| 4-1BB intracellular domain | 477-518 (SEQ ID NO: 21) |
| CD3zeta intracellular domain | 519-630 (SEQ ID NO: 45) |

*MEFGLSWLFLVAILKGVQC* GSKGIFVIQSESLKKCIQAGKSVLTLENCKQANKH

MLWKWVSNHGLFNIGGSGCLGLNFSAPEQPLSLYECDSTLVSLRWRCNRKMITG

PLQYSVQVAHDNTVVASRKYIHKWISYGSGGGDICEYLHKDLHTITSAEVGCDTI

WEKDLNSHICYQFNLLSSLSWSEAHSSCQMQGGTLLSITDETEENFIREHMSSKT

VEVWMGLNQLDEHAGWQWSDGTPLNYLNWSPEVNFEPFVEDHCGTFSSFMPS

AWRSRDCESTLPYICKKYLNHIDHEIVEVNTSDMYPMPNTLEYGNRTYKIINANM

TWYAAIKTCLMHKAQLVSITDQYHQSFLTVVLNRLGYAHWIGLFTTDNGLNFD

WSDGTKSSFTFWKDEESSLLGDCVFADSNGRWHSTACESFLQGAICHVPPETRQ

SEHPELAS*GGGGSGGGGS*GIYIWAPLAGTCGVLLLSLVITLYCKRGRKKLLYI

FKQPFMRPVQTTQEEDGCSCRFPEEEEGGCELRVKFSRSADAPAYQQGQNQLYN

ELNLGRREEYDVLDKRRGRDPEMGGKPRRKNPQEGLYNELQKDKMAEAYSEIG

MKGERRRGKGHDGLYQGLSTATKDTYDALHMQALPPR

-continued

Nucleotide sequence of 4025 pTRPE.CysR.CD8H.BBz CAAR (construct 4025.C)
(SEQ ID NO: 37)

*PLA2R Signal peptide* 1-60 (SEQ ID NO: 65)

PLA2R pro-peptide 61-117 (SEQ ID NO: 67)

CysR 118-504 (SEQ ID NO: 60)

*CD8 Hinge region* 511-645 (SEQ ID NO: 42)

CD8 TMD 646-717 (SEQ ID NO: 20)

4-1BB intracellular domain 718-843 (SEQ ID NO: 22)

CD3zeta intracellular domain 844-1179 (SEQ ID NO: 72)

Stop codon 1180-1182

*ATGCTGCTGAGCCCTAGCCTG CTGCTGCTCCTGCTTCTT GGAGCCCCTAGAGG*

*ATGTGCC* GGATCTGAAGGTGTTGCCGCCGCTCTGACACCCGAGAGACTG

CTGGAATGGCAGGACAAGGGCATCTTCGTGATCCAGAGCGAGAGCCTGAAG

AAGTGCATCCAGGCCGGCAAGAGCGTGCTGACCCTGGAAAATTGCAAGCAG

GCCAACAAGCACATGCTGTGGAAATGGGTGTCCAACCACGGCCTGTTCAACA

TCGGCGGCTCTGGATGTCTGGGCCTGAATTTCTCTGCCCCTGAGCAGCCTCTG

AGCCTGTACGAGTGTGATAGCACCCTGGTGTCCCTGAGATGGCGGTGCAACC

GGAAGATGATCACAGGCCCTCTGCAGTACTCTGTGCAGGTCGCCCACGACAA

TACCGTGGTGGCCAGCAGAAAGTACATCCACAAGTGGATCAGCTACGGCAGC

GGCGGAGGCGACATCTGTGAATACCTGCACAAGGATCTGtccgga*ACCACGACG*

*CCAGCGCCGCGACCACCAACACCGGCGCCCACCATCGCGTCGCAGCCCCTGTCC*

*CTGCGCCCAGAGGCGTGCCGGCCAGCGGCGGGGGGCGCAGTGCACACGAGGG*

*GGCTGGACTTCGCCTGTGAT*ATCTACATCTGGGCGCCCTTGGCCGGGACTT

GTGGGGTCCTTCTCCTGTCACTGGTTATCACCCTTTACTGCAAACGGGGC

AGAAAGAAACTCCTGTATATATTCAAACAACCATTTATGAGACCAGTACAAA

CTACTCAAGAGGAAGATGGCTGTAGCTGCCGATTTCCAGAAGAAGAAGAAG

GAGGATGTGAACTGAGAGTGAAGTTCAGCAGGAGCGCAGACGCCCCCGCGT

ACAAGCAGGGCCAGAACCAGCTCTATAACGAGCTCAATCTAGGACGAAGAG

AGGAGTACGATGTTTTGGACAAGAGACGTGGCCGGGACCCTGAGATGGGGG

GAAAGCCGAGAAGGAAGAACCCTCAGGAAGGCCTGTACAATGAACTGCAGA

AAGATAAGATGGCGGAGGCCTACAGTGAGATTGGGATGAAAGGCGAGCGCC

GGAGGGGCAAGGGGCACGATGGCCTTTACCAGGGTCTCAGTACAGCCACCA

AGGACACCTACGACGCCCTTCACATGCAGGCCCTGCCCCCTCGCTAA

Amino acid sequence of 4025 pTRPE.CysR.CD8H.BBz CAAR (construct 4025.C)
(SEQ ID NO: 38)

*PLA2R Signal peptide* 1-20

CysR 40-168 (SEQ ID NO: 61)

*CD8 Hinge region* 171-215 (SEQ ID NO: 43)

CD8 TMD 216-239 (SEQ ID NO: 19)

-continued 4-1BB intracellular domain 240-281 (SEQ ID NO: 21)

CD3zeta intracellular domain 282-393 (SEQ ID NO: 23)

MLLSPSLLLLLLLGAPRGCAGSEGVAAALTPERLLEWQDKGIFVIQSESLKKCIQ

AGKSVLTLENCKQANKHMLWKWVSNHGLFNIGGSGCLGLNFSAPEQPLSLYEC

DSTLVSLRWRCNRKMITGPLQYSVQVAHDNTVVASRKYIHKWISYGSGGGDICE

YLHKDLSG*TTTPAPRPPTPAPTIASQPLSLRPEACRPAAGGAVHTRGLDFACD*IYIWA

PLAGTCGVLLLSLVITLYCKRGRKKLLYIFKQPFMRPVQTTQEEDGCSCRFPEE

EEGGCELRVKFSRSADAPAYKQGQNQLYNELNLGRREEYDVLDKRRGRDPEMG

GKPRRKNPQEGLYNELQKDKMAEAYSEIGMKGERRRGKGHDGLYQGLSTATK

DTYDALHMQALPPR

Nucleotide sequence of 4026 pTRPE. CysR-FNII-CTLD1.CD8H.BBz CAAR (construct 4026.CF1)

(SEQ ID NO: 39)

*PLA2R Signal peptide* 1-60 (SEQ ID NO: 65)

PLA2R pro-peptide 61-117

CysR-FNII-CTLD1 118-1143 (SEQ ID NO: 62)

*CD8 Hinge region* 1149-1284 (SEQ ID NO: 42)

CD8 TMD 1285-1356 (SEQ ID NO: 20)

4-1BB intracellular domain 1357-1482 (SEQ ID NO: 22)

CD3zeta intracellular domain 1483-1818 (SEQ ID NO: 72)

Stop codon 1819-1821

*ATGCTGCTGAGCCCTAGCCT GCTGCTGCTCCTGCTTC TTGGAGCCCCTAGAGG*

*ATGTGCC* GGATCTGAAGGTGTTGCCGCCGCTCTGACACCCGAGAGACTG

CTGGAATGGCAGGACAAGGGCATCTTCGTGATCCAGAGCGAGAGCCTGAAG

AAGTGCATCCAGGCCGGCAAGAGCGTGCTGACCCTGGAAAATTGCAAGCAG

GCCAACAAGCACATGCTGTGGAAATGGGTGTCCAACCACGGCCTGTTCAACA

TCGGCGGCTCTGGATGTCTGGGCCTGAATTTCTCTGCCCCTGAGCAGCCTCTG

AGCCTGTACGAGTGTGATAGCACCCTGGTGTCCCTGAGATGGCGGTGCAACC

GGAAGATGATCACAGGCCCTCTGCAGTACTCTGTGCAGGTCGCCCACGACAA

TACCGTGGTGGCCAGCAGAAAGTACATCCACAAGTGGATCAGCTACGGCAGC

GGCGGAGGCGACATCTGTGAATACCTGCACAAGGATCTGCACACCATCAAGG

GCAACACCCACGGAATGCCCTGCATGTTCCCGTTTCAGTACAACCACCAGTG

GCACCACGAGTGCACCAGAGAAGGCAGAGAGGACGACCTGCTTTGGTGCGC

CACAACCAGCAGATACGAGCGGGATGAGAAGTGGGGCTTCTGCCCTGATCCT

ACCTCTGCCGAAGTGGGCTGCGATACCATCTGGGAGAAAGACCTGAACAGCC

ACATCTGCTACCAGTTCAACCTGCTGTCCAGCCTGTCTTGGAGCGAGGCCCAC

AGCAGCTGTCAAATGCAAGGCGGCACACTGCTGAGCATCACCGACGAGACA

GAGGAAAACTTCATCCGCGAGCACATGAGCAGCAAGACCGTGGAAGTGTGG

ATGGGACTGAACCAGCTGGATGAGCATGCCGGATGGCAGTGGAGTGATGGC

-continued

ACCCCTCTGAACTACCTGAACTGGTCCCCTGAAGTGAACTTCGAGCCCTTCGT

GGAAGATCACTGCGGCACCTTCAGCAGCTTCATGCCCAGCGCTTGGAGAAGC

AGAGACTGCGAGAGCACCCTGCCTTACATCTGCAAGAAGTACCTGAACCACA

TCGACCACGAGATCGTGGAAAAGGACGCCTGGAAGTACTACGCCACACACTG

CGAGtccgga*ACCACGACGCCAGCGCCGCGACCACCAACACCGGCGCCCACCATCG*

*CGTCGCAGCCCCTGTCCCTGCGCCCAGAGGCGTGCCGGCCAGCGGCGGGGGGC*

*GCAGTGCACACGAGGGGGCTGGACTTCGCCTGTGAT*ATCTACATCTGGGCGCC

CTTGGCCGGGACTTGTGGGGTCCTTCTCCTGTCACTGGTTATCACCCTTT

ACTGCAAACGGGGCAGAAAGAAACTCCTGTATATATTCAAACAACCATTTAT

GAGACCAGTACAAACTACTCAAGAGGAAGATGGCTGTAGCTGCCGATTTCCA

GAAGAAGAAGAAGGAGGATGTGAACTGAGAGTGAAGTTCAGCAGGAGCGCA

GACGCCCCCGCGTACAAGCAGGGCCAGAACCAGCTCTATAACGAGCTCAATC

TAGGACGAAGAGAGGAGTACGATGTTTTGGACAAGAGACGTGGCCGGGACC

CTGAGATGGGGGGAAAGCCGAGAAGGAAGAACCCTCAGGAAGGCCTGTACA

ATGAACTGCAGAAAGATAAGATGGCGGAGGCCTACAGTGAGATTGGGATGA

AAGGCGAGCGCCGGAGGGGCAAGGGGCACGATGGCCTTTACCAGGGTCTCA

GTACAGCCACCAAGGACACCTACGACGCCCTTCACATGCAGGCCCTGCCCCC

TCGCTAA

Amino acid sequence of 4026 pTRPE. CysR-FNII-CTLD1.CD8H.BBz CAAR (construct 4026.CF1)

(SEQ ID NO: 40)

| | |
|---|---|
| ***PLA2R Signal peptide*** | 1-20 |
| CysR-FNII-CTLD1 | 40-381 (SEQ ID NO: 63) |
| *CD8 Hinge region* | 384-428 (SEQ ID NO: 43) |
| **CD8 TMD** | 429-452 (SEQ ID NO: 19) |
| 4-1BB intracellular domain | 453-494 (SEQ ID NO: 21) |
| CD3zeta intracellular domain | 495-606 (SEQ ID NO: 23) |

*MLLSPSLLLLLLLGAPRGCA* GSEGVAAALTPERLLEWQDKGIFVIQSESLKKCIQA

GKSVLTLENCKQANKHMLWKWVSNHGLFNIGGSGCLGLNFSAPEQPLSLYECD

STLVSLRWRCNRKMITGPLQYSVQVAHDNTVVASRKYIHKWISYGSGGGDICEY

LHKDLHTIKGNTHGMPCMFPFQYNHQWHHECTREGREDDLLWCATTSRYERDE

KWGFCPDPTSAEVGCDTIWEKDLNSHICYQFNLLSSLSWSEAHSSCQMQGGTLL

SITDETEENFIREHMSSKTVEVWMGLNQLDEHAGWQWSDGTPLNYLNWSPEVN

FEPFVEDHCGTFSSFMPSAWRSRDCESTLPYICKKYLNHIDHEIVEKDAWKYYAT

HCESG*TTTPAPRPPTPAPTIASQPLSLRPEACRPAAGGAVHTRGLDFACD*IYIWAPLA

GTCGVLLLSLVITLYCKRGRKKLLYIFKQPFMRPVQTTQEEDGCSCRFPEEEEG

GCELRVKFSRSADAPAYKQNQLYNELNLGRREEYDVLDKRRGRDPEMGGKP

-continued
RRKNPQEGLYNELQKDKMAEAYSEIGMKGERRRGKGHDGLYQGLSTATKDTY

DALHMQALPPR

>BC144631.1 Homo sapiens phospholipase A2 receptor 1, 180 kDa, mRNA (cDNA clone MGC: 178179 IMAGE: 9053162), complete cds (SEQ ID NO: 41)

CCGGAGAGCCCAGTGGTTAGCGATGCTGCTGTCGCCGTCGCTGCTGCTGCTGCTGCTGCTGGGGGCGCCG

CGGGGCTGCGCCGAGGGTGTGGCGGCGGCGCTTACCCCCGAGCGGCTCCTGGAGTGGCAGGATAAAGGAA

TATTTGTTATCCAAAGTGAGAGTCTCAAGAAATGCATTCAAGCAGGTAAATCGGTTCTGACCCTGGAGAA

CTGCAAGCAAGCAAACAAGCACATGCTGTGGAAATGGGTTTCAAACCATGGCCTCTTTAACATAGGAGGC

AGCGGTTGCCTGGGCCTGAATTTCTCCGCCCCAGAGCAGCCATTAAGCTTATATGAATGTGACTCCACCC

TCGTTTCCTTACGGTGGCGCTGTAACAGGAAGATGATCACAGGCCCGCTGCAGTACTCTGTCCAGGTGGC

GCATGACAACACAGTGGTGGCCTCACGGAAGTATATTCATAAGTGGATTTCTTATGGGTCAGGTGGTGGA

GACATTTGTGAATATCTACACAAAGATTTGCATACAATCAAAGGGAACACCCACGGGATGCCGTGTATGT

TTCCCTTCCAGTATAACCATCAGTGGCATCATGAATGTACCCGTGAAGGTCGGGAAGATGACTTACTGTG

GTGTGCCACGACAAGCCGTTATGAAAGAGATGAAAAGTGGGGATTTTGCCCTGATCCCACCTCTGCAGAA

GTAGGTTGTGATACTATTTGGGAGAAGGACCTCAATTCACACATTTGCTACCAGTTCAACCTGCTTTCAT

CTCTCTCTTGGAGTGAGGCACATTCTTCATGCCAGATGCAAGGAGGTACGCTGTTAAGTATTACAGATGA

AACTGAAGAAAATTTCATAAGGGAGCACATGAGCAGTAAAACAGTGGAGGTGTGGATGGGCCTCAATCAG

CTGGATGAACACGCTGGCTGGCAGTGGTCTGATGGAACGCCGCTCAACTATCTGAATTGGAGCCCAGAGG

TAAATTTTGAGCCATTTGTTGAAGATCACTGTGGAACATTTAGTTCATTTATGCCAAGTGCCTGGAGGAG

TCGGGATTGTGAGTCCACCTTGCCATATATATGTAAAAAATATCTAAACCACATTGATCATGAAATAGTT

GAAAAAGATGCGTGGAAATATTATGCTACCCACTGTGAGCCTGGCTGGAATCCCTACAATCGTAATTGCT

ACAAACTTCAGAAAGAAGAAAAGACCTGGCATGAGGCTCTGCGTTCTTGTCAGGCTGATAACAGTGCATT

AATAGACATAACCTCATTAGCAGAGGTGGAGTTTCTTGTAACCCTCCTTGGAGATGAAAATGCATCAGAA

ACATGGATTGGTTTGAGCAGCAATAAAATTCCAGTTTCCTTTGAATGGTCTAATGACTCTTCAGTCATCT

TTACTAATTGGCACACACTTGAGCCCCACATTTTTCCAAATAGAAGCCAGCTGTGTGTCTCAGCAGAGCA

GTCTGAGGGACACTGGAAAGTCAAAAATTGTGAAGAAAGACTTTTTTACATTTGTAAAAAAGCAGGCCAT

GTCCTCTCTGATGCTGAATCAGGATGTCAAGAGGGATGGGAGAGACATGGTGGATTCTGTTACAAAATTG

ACACAGTCCTTCGAAGCTTTGACCAAGCTTCCAGCGGTTATTACTGTCCTCCTGCACTTGTAACCATTAC

AAACAGGTTTGAACAGGCTTTTATTACCAGTTTGATCAGTAGTGTGGTAAAAATGAAGGACAGTTATTTT

TGGATAGCTCTTCAGGACCAAAATGATACGGGAGAATACACTTGGAAGCCAGTAGGGCAGAAACCCGAGC

CGGTGCAGTACACACACTGGAACACACACCAGCCGCGCTACAGTGGTGGCTGTGTTGCCATGCGAGGAAG

GCATCCACTTGGTCGCTGGGAAGTGAAGCACTGTCGGCACTTTAAGGCAATGTCCTTGTGCAAGCAGCCA

GTTGAAAATCAGGAAAAAGCAGAGTATGAAGAGAGATGGCCCTTTCACCCCTGCTATTTGGACTGGGAGT

CAGAGCCTGGTCTGGCCAGTTGCTTCAAGGTATTTCATAGTGAAAAAGTTCTGATGAAAAGAACATGGAG

AGAAGCTGAAGCATTTTGCGAAGAATTTGGAGCTCATCTTGCAAGCTTTGCCCATATTGAGGAAGAGAAT

TTTGTGAATGAGCTCTTACATTCAAAATTTAATTGGACAGAAGAAAGGCAGTTCTGGATTGGATTTAATA

AAAGAAACCCACTGAATGCCGGCTCATGGGAGTGGTCTGATAGAACTCCTGTTGTCTCTTCGTTTTTAGA

CAACACTTATTTTGGAGAAGATGCAAGAAACTGTGCTGTTTATAAGGCAAACAAAACATTGCTGCCCTTA

CACTGTGGTTCCAAACGTGAATGGATATGCAAAATCCCAAGAGATGTGAAACCCAAGATTCCGTTCTGGT

ACCAGTACGATGTACCCTGGCTCTTTTATCAGGATGCAGAATACCTTTTTCATACCTTTGCCTCAGAATG

-continued

```
GTTGAACTTTGAGTTTGTCTGTAGCTGGCTGCACAGTGATCTTCTCACAATTCATTCTGCACATGAGCAA

GAATTCATCCACAGCAAAATAAAAGCGCTATCAAAGTATGGTGCAAGTTGGTGGATTGGACTTCAAGAAG

AAAGAGCCAATGATGAATTTCGCTGGAGAGATGGAACACCAGTGATATACCAGAACTGGGACACAGGAAG

AGAAAGAACTGTGAATAATCAGAGCCAGAGATGTGGCTTTATTTCTTCTATAACAGGACTCTGGGGTAGT

GAAGAGTGTTCAGTTTCTATGCCTAGTATCTGTAAGCGAAAAAAGGTTTGGCTCATAGAGAAAAAGAAAG

ATACACCAAAACAACATGGAACGTGTCCCAAAGGATGGCTATATTTTAACTATAAGTGCCTTCTGCTGAA

TATCCCCAAAGACCCAAGCAGTTGGAAGAACTGGACGCATGCTCAACATTTCTGTGCTGAAGAAGGGGGG

ACCCTGGTCGCCATTGAAAGTGAGGTGGAGCAAGCTTTCATTACTATGAATCTTTTTGGCCAGACCACCA

GTGTGTGGATAGGTTTACAAAATGATGATTATGAAACATGGCTAAATGGAAAGCCTGTGGTATATTCTAA

CTGGTCTCCATTTGATATAATAAATATTCCAAGTCACAATACCACTGAAGTTCAGAAACACATTCCTCTC

TGTGCCTTACTCTCAAGTAATCCTAATTTTCATTTCACTGGAAAATGGTATTTTGAAGACTGTGGAAAGG

AAGGCTATGGGTTTGTTTGTGAAAAAATGCAAGATACTTCTGGACACGGTGTAAATACATCTGATATGTA

TCCAATGCCCAATACCTTAGAATATGGAAACAGAACTTACAAAATAATTAATGCAAATATGACTTGGTAT

GCAGCAATAAAAACCTGCCTGATGCACAAAGCACAACTGGTCAGCATCACAGACCAGTATCACCAGTCCT

TCCTCACTGTTGTCCTCAACCGGCTAGGATATGCCCACTGGATTGGACTGTTCACCACAGATAATGGTCT

TAATTTTGACTGGTCTGATGGCACCAAATCTTCTTTCACTTTTTGGAAAGATGAGGAGTCCTCCCTCCTT

GGTGACTGCGTTTTTGCCGACAGCAACGGACGCTGGCATAGCACAGCCTGCGAGTCATTTCTGCAAGGTG

CCATTTGTCATGTGCCACCTGAAACAAGACAATCTGAACACCCAGAGTTGTGCTCAGAAACATCTATTCC

CTGGATAAAATTTAAAAGTAATTGCTACAGTTTTTCTACAGTCCTAGACAGTATGAGTTTTGAGGCTGCT

CATGAATTTTGCAAAAAGGAAGGTTCTAATCTTTTAACAATCAAGGATGAGGCTGAAAATGCATTTCTCC

TAGAAGAGCTGTTTGCTTTTGGTTCTTCTGTCCAGATGGTTTGGTTGAATGCTCAATTTGATGATGAAAC

CATAAAGTGGTTTGATGGAACTCCCACAGACCAGTCAAACTGGGGCATTCGGAAGCCAGACACAGACTAC

TTCAAGCCCCATCATTGTGTTGCCTTGAGGATCCCTGAAGGATTATGGCAGCTATCCCCGTGTCAAGAAA

AAAAAGGCTTTATATGTAAAATGGAGGCAGATATTCACACTGCAGAGGCGCTGCCAGAAAAAGGACCAAG

TCACAGCATCATTCCTCTTGCGGTTGTACTGACACTGATAGTCATTGTGGCCATTTGCACACTTTCCTTC

TGCATATACAAGCATAACGGTGGCTTCTTCAGGAGACTTGCAGGGTTTCGGAATCCTTACTATCCTGCAA

CCAACTTTAGTACAGTATATTTAGAAGAAAATATTCTCATTTCTGATCTTGAGAAGAGTGACCAATAATA

ATGAGGTCAGAGAATGCCACAGACACCAGGG
```

—Production of HIV-1 Based Self-Inactivating Lentivirus 293T cells were transfected at a confluence of 90% with a mixture of the pTRPE-gene-of-interest, the packaging plasmid pGAG-Pol and pRSV-Rev and the envelope plasmid pCI VSVg in a complex with Lipofectamine 2000. Lentivirus containing supernatant was harvested after 24 and 48 hours, filtered through a 0.45 micron polyethersulfone (PES) membrane, concentrated at 12,000×g for 24 hours at 4° C., and stored at −80° C.

—Stimulation, Transduction, and Expansion of Primary Hunan T Cells.

Primary human T cells were cultured in CTS OpTmizer T cell expansion SFM with 5% HSAB, 2.6% supplement, 1% penicillin/streptomycin and 1% glutamax. Bulk T cells ($CD4^+$ and $CD8^+$) were stimulated with anti-CD3 and anti-CD28 beads at a bead:cell ratio of 3:1. The culture medium was supplemented with 100 IU/ml interleukin 2. 24 hours after stimulation, $10^6$ T cells were transduced with CAAR or mock transduced. Expansion of the T cells were monitored for 8-12 days. Cell surface expression of the CAAR constructs was validated by flow cytometry with IgG purified from the plasma of a patient with primary membranous nephropathy and isotype control antibody.

—Reporter Assay with NFAT-GFP Jurkat T Cells

Jurkat cells were cultured at 37° C. with 5% CO2 in a completely humidified environment using RPMI1640, HEPES 10 mM, and FBS at 10%. To test signal transduction by CAAR-target interaction, the CAAR constructs were expressed in a Jurkat reporter cell line that has been selected (G418) for stable expression of GFP controlled under an NFAT response element, facilitating GFP expression after CAAR engagement and PLCgamma and IP3 mediated intracellular calcium release. Jurkat cells were transduced with CAAR lentivirus at a multiplicity of infection of 3 and expression of the CAAR construct was validated after >72 hours with an anti-PLA2R monoclonal antibody (Novus Biologicals®) and IgG purified from the plasma of a patient with primary membranous nephropathy by flow cytometry. For characterization of CAAR-target interaction, the CAAR Jurkat cells were incubated at 37° C. for 6 hours with plate-bound anti-PLA2R monoclonal as below. GFP expression was validated by flow cytometry.

—Stimulation 1 million Jurkat-NFAT-GFP cells were transduced with each lentivirus encoding for PLA2R CAAR construct C, CF1, CF123, CF1237, CD17, C17, 4025.C, 4026.CF1, 4027.CF12, 4028.CF123 and untransduced Jurkat cells were used as negative control. Transduced and untransduced cells were plated in a 96-well plate at $2\times10^5$ cells/well in 100 μl cell culture medium.

The stimulation conditions were as follows:

Novus monoclonal antibody (mAb) anti-PLA2R either 0.5 μg/well or 1 μg/well; Clone 12-6-5

Sigma polyclonal antibody anti-PLA2R 0.5 μg/well;

Isotype antibody for Novus mAb anti-PLA2R (0.5 μg/stain)

medium only (no stimulation)

PMA/Ionomycin (maximum activation)

Or, transduced and untransduced cells were plated in a 96-well plate at $5\times10^4$ cells/well in 100 μl cell culture medium.

Cells and antibodies were incubated at 37° C. for 6 hours. At the end of the 6 h, cells were examined by flow cytometry for expression of NFAT-GFP as an indicator of T cell activation.

In Vitro IFNγ Cytokine Assay

PLA2R CAAR or mock transduced primary human T cells were cultured for 24 h at $5\times10^4$/well in a 96-well plate coated with 10 μg/ml either IgG purified from plasma of patient with primary membranous nephropathy or control human IgG. Culture supernatants were then harvested for detection of IFN-γ by ELISA.

—In Vivo Efficacy Testing of CAAR T Cells

To test the in vivo efficacy, anti-PLA2R BCR-expressing cells, for example hybridoma cells or human cell lines, targeting human PLA2R are generated. PLA2R BCR-expressing cells are transduced with lentiviral vectors expressing click-beetle green or click-beetle red luciferase and GFP. To test the efficacy of CAAR-T cells against the PLA2R-specific target cells, approximately $2\times10^5$ anti-PLA2R cells are injected intravenously into NSG mice (age 6-8 weeks), after pre-treatment of mice daily for 2 days with 600 mg/kg intravenous immunoglobulin to minimize FcγR-mediated toxicity against BCR-expressing cells. After 4-5 days, PLA2R CAAR T cells (approximately $10^7$ cells per mouse) are injected intravenously. Bioluminescence and/or serum autoantibodies are quantified every 2-3 days after injection to monitor CAAR T cell efficacy.

The results of the experiments are now described.

Example 1

Four PLA2R constructs representing different domains of the PLA2R were cloned into a CAAR expression system (4025.C, 4026.CF1, Construct 4027.CF12 and 4028.CF123). The general schematics of the extracellular domains of PLA2R of particular interest in the invention are illustrated in FIG. 1. The N terminal domain is an immunodominant epitope that is recognized by patient serum antibodies. The CysR and CTLD3 domain interact to form a ring-like structure that may better present immunodominant epitopes; hence constructs including the CysR through CTLD3 domains were generated. In addition to the cysteine-rich domain, serum antibody immunoreactivity to the C-type lectin domains 1 and 7 has also been reported.

The PLA2R CAAR constructs illustrated in FIGS. 2A-2G. All constructs use the CD8 transmembrane domain and BBZ intracellular domain and differ in their extracellular composition.

Figure 2A:
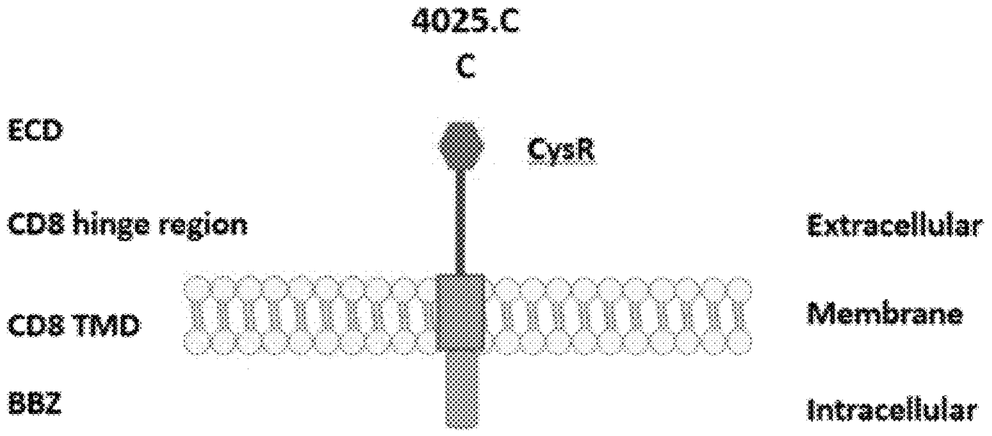
FIGS. 2A-2G are a series of schematic diagrams illustrating the various PLA2R CAAR constructs described in this invention. Abbreviations for here and throughout: ECD: extracellular domain; TMD: transmembrane domain; BBZ: cytoplasmic tandem 41BB (CD137) and CD3-zeta signaling domain; CysR=cysteine rich domain; FNII=fibronectin type II domain; CTLD=C-type lectin domain. All constructs use a CD8 transmembrane domain and BBZ cytoplasmic domain and differ in their extracellular composition as follows.

Construct 4025.C was comprised of a cysteine rich extracellular domain, a CD8 hinge region, a CD8 transmembrane domain, a 4-1BB intracellular domain and CD3 zeta signaling domain (FIG. 2A, SEQ ID NOs: 37 & 38).

Figure 2B:
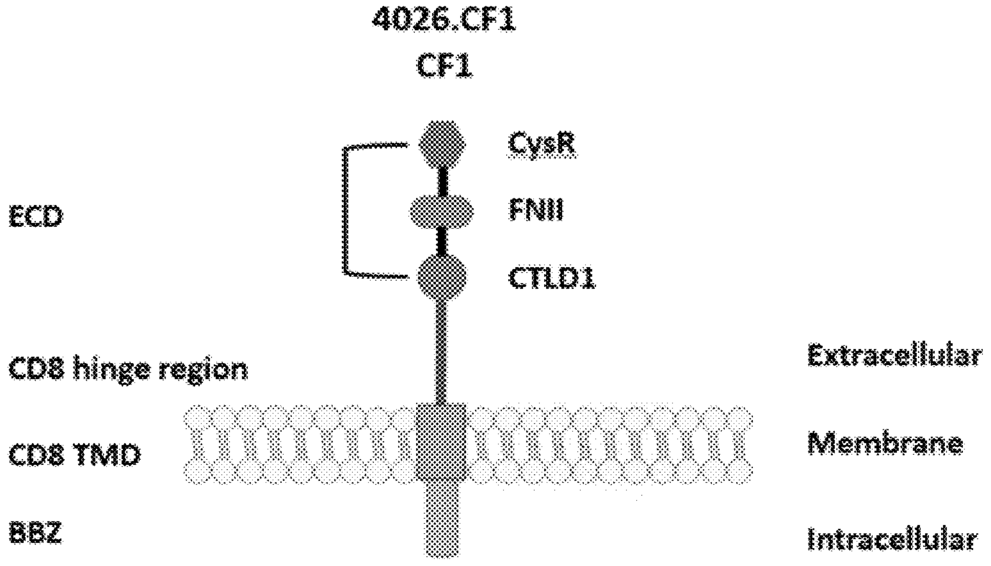

Construct 4026.CF1 was comprised of an extracellular domain comprising a cysteine rich domain, a fibronectin II domain, and a C-type lectin 1 domain. Construct 4026.CF1 also included a CD8 hinge region, a CD8 transmembrane domain, a 4-1BB intracellular domain and CD3 zeta signaling domain (FIG. 2B, SEQ ID NOs: 39 & 40).

Figure 2C:
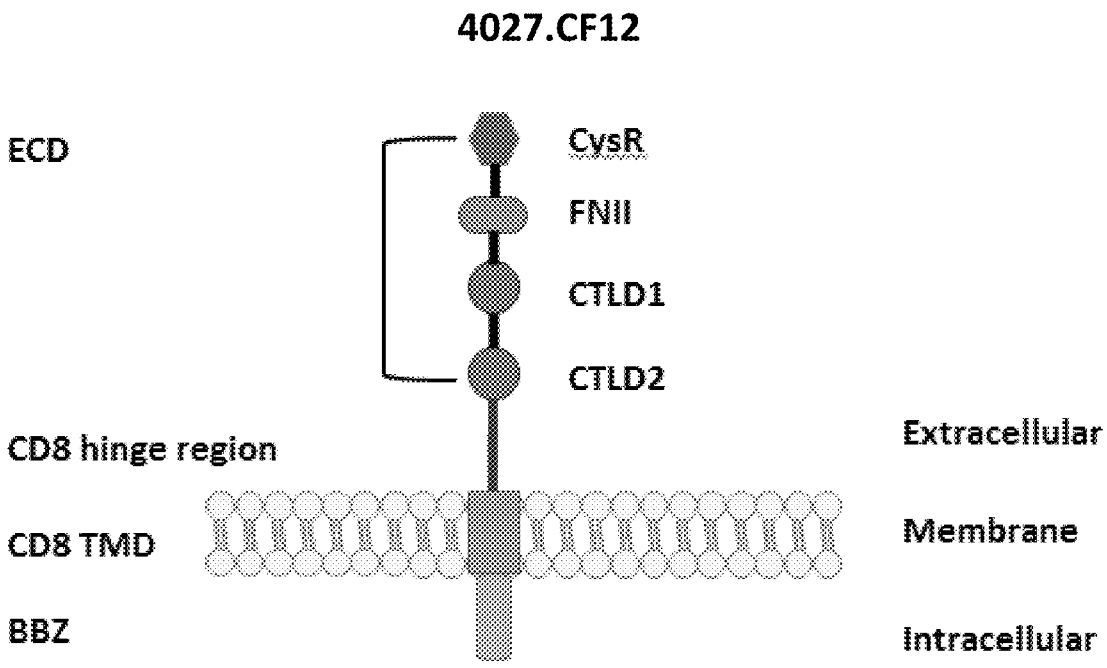

Construct 4027.CF12 was comprised of an extracellular domain comprising a cysteine rich domain, a fibronectin II domain, a C-type lectin 1 domain, and a C-type lectin 2 domain. Construct 4027.CF12 also included a CD8 hinge region, a CD8 transmembrane domain, a 4-1BB intracellular domain and CD3 zeta signaling domain (FIG. 2C, SEQ ID NOs: 11 & 12).

Figure 2D:
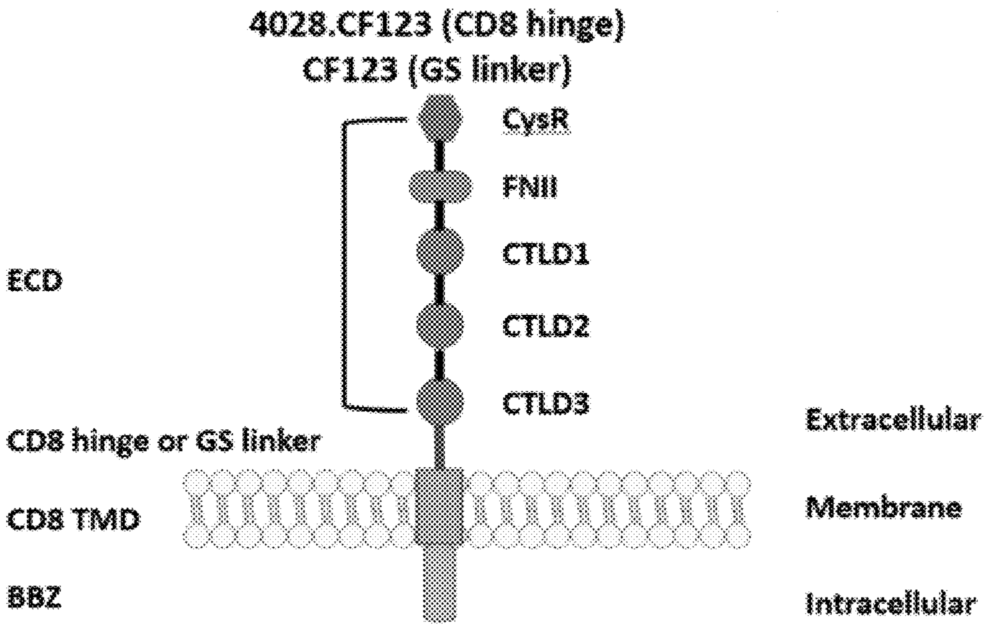
Figure 2E:
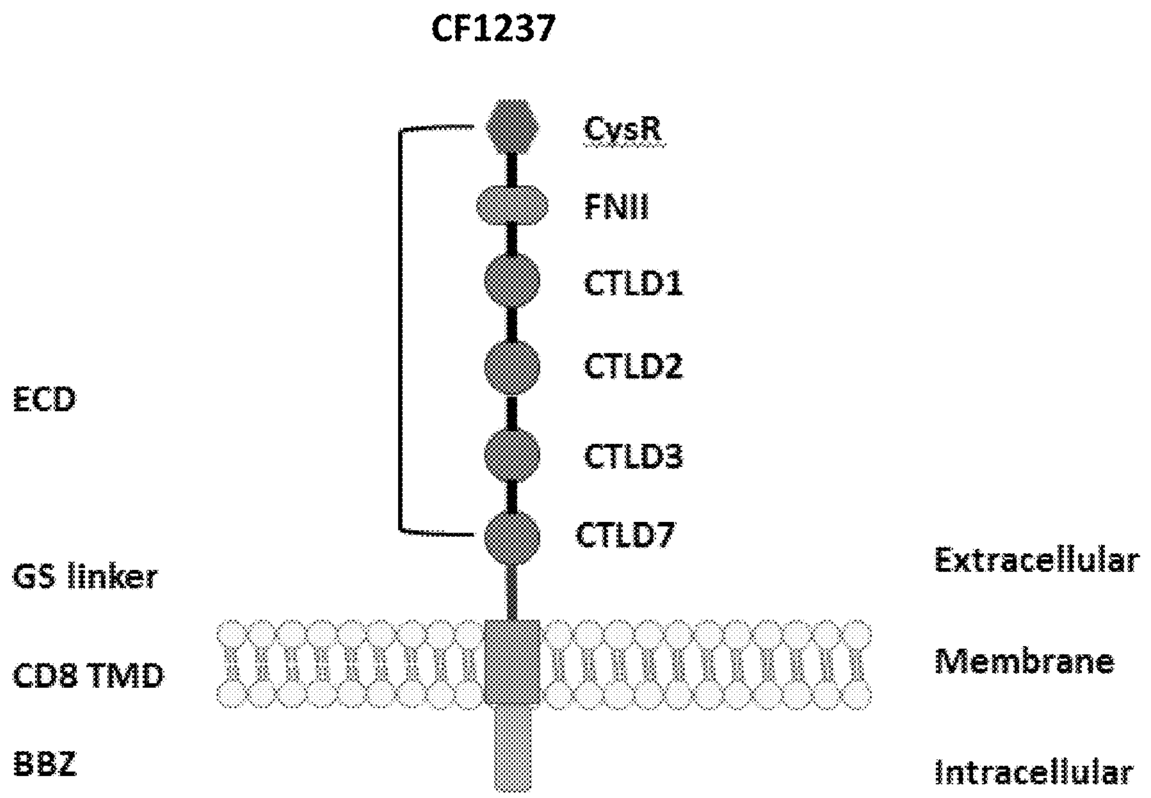
Figure 2F:
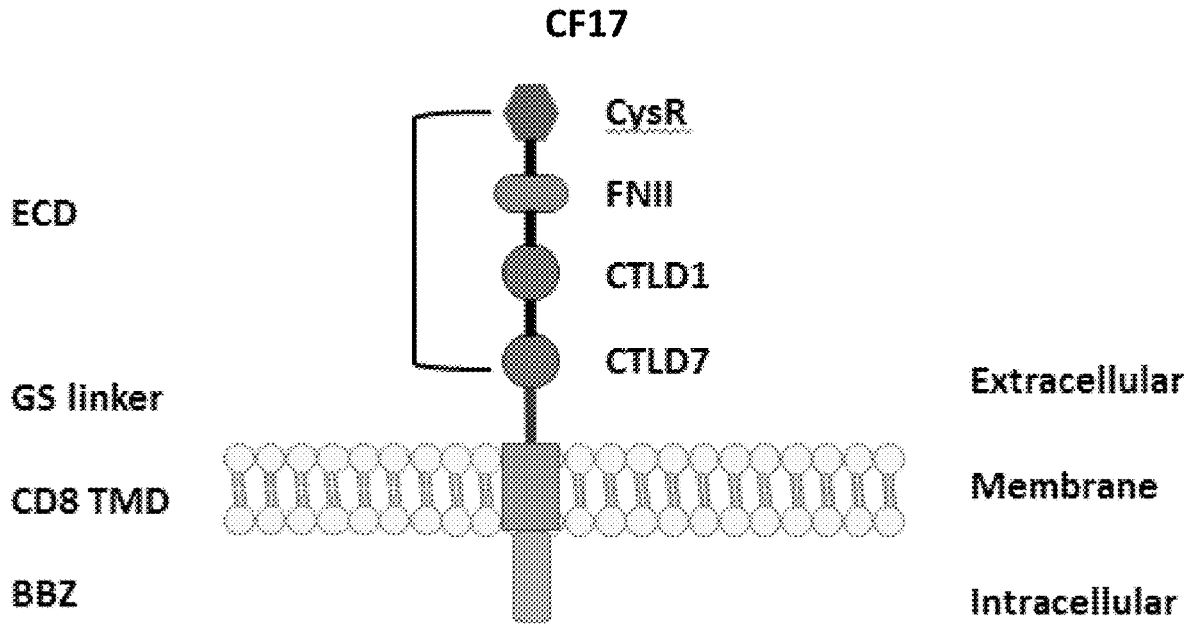
Figure 2G:
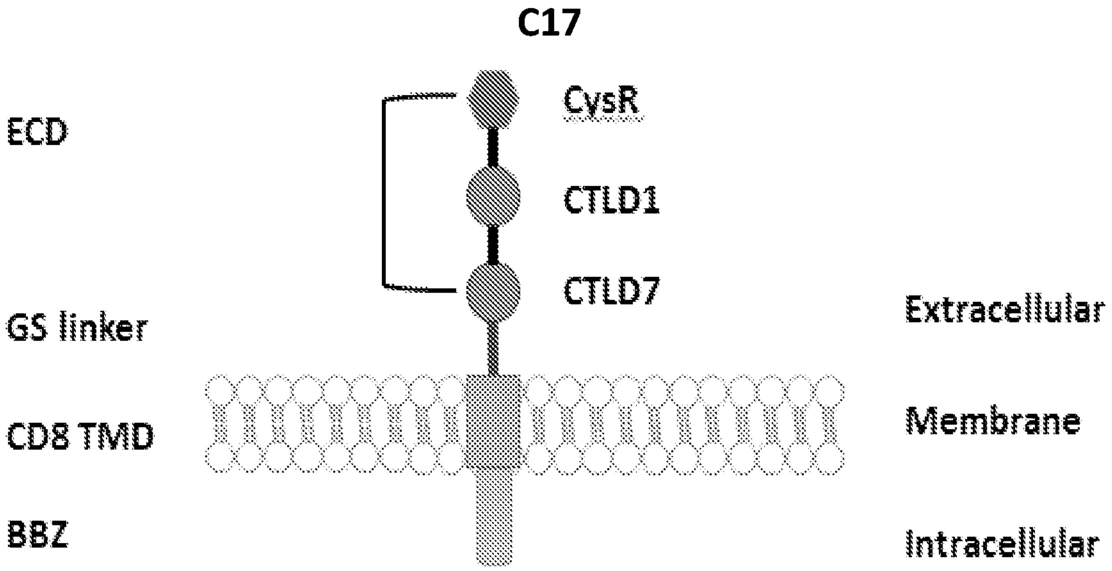

Construct 4028.CF123 was comprised of an extracellular domain comprising a cysteine rich domain, a fibronectin II domain, a C-type lectin 1 domain, a C-type lectin 2 domain, and a C-type lectin 3 domain. Construct 4028.CF123 also included a CD8 hinge region, a CD8 transmembrane domain, a 4-1BB intracellular domain and CD3 zeta signaling domain (FIG. 2D, SEQ ID NOs: 17 & 18). A detailed map of PLA2R CAAR Construct 4028.CF123 is shown in FIG. 3A.

Figure 4:
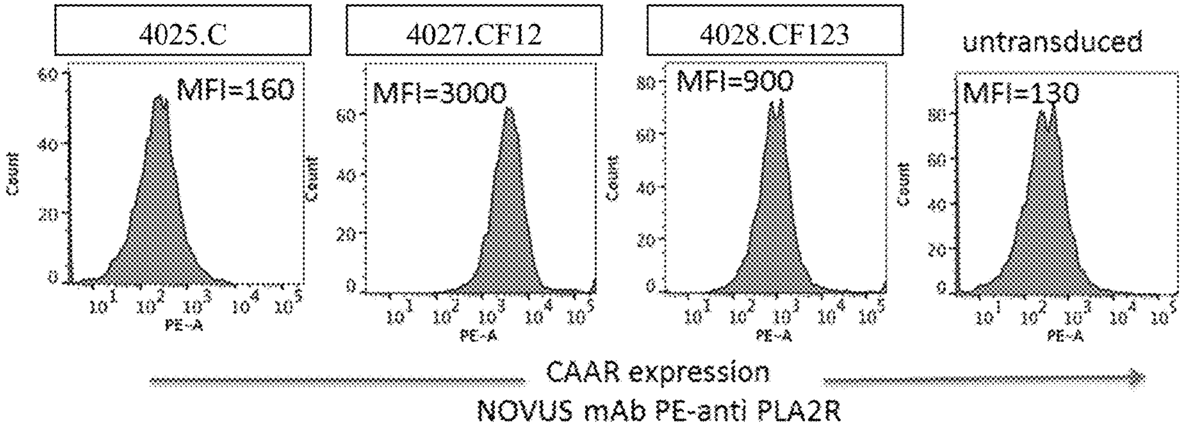
FIG. 4 is a series of flow cytometry plots demonstrating surface expression of a subset of PLA2R CAARs (4027.CF12 and 4028.CF123) on Jurkat NFAT-GFP cells. The expression of PLA2R CAAR by Jurkat NFAT-GFP cells transduced with different PLA2R lentiviral constructs was measured (MOI 5:1, 48 h) using a commercial Novus monoclonal antibody (mAb) specific for the PLA2R CTLD2 domain. Jurkat T cells expressing construct 4027.CF12 or 4028.CF123, but not those T cells bearing 4025.C, which does not include the CTLD2 domain and hence is not detectable by the mAb used, or untransduced Jurkat NFAT-GFP cells, exhibited detectable surface expression of the CAAR.

To test whether the CAAR molecules were functional, the following experiments were conducted:

1 million Jurkat-NFAT-GFP cells were transduced with each lentivirus encoding for 4025.C, 4027.CF12, 4028.CF123 and untransduced Jurkat cells were used as negative control. Transduced and untransduced cells were plated in a 96-well plate at $2\times10^5$ cells/well in 100 ul cell culture medium. FIG. 4 shows the PLA2R CAAR expression. The expression of PLA2R CAAR by Jurkat NFAT-GFP cells transduced with different PLA2R lentiviral constructs was measured by staining with soluble anti-PLA2R monoclonal antibody conjugated to PE. Jurkat T cells bearing construct 4027.CF12 or 4028.CF123, but not those T cells bearing construct 4025.C, which does not include the CTLD2 domain and hence is not detectable by the mAb used, exhibited detectable surface expression of the CAAR.

Figure 5:
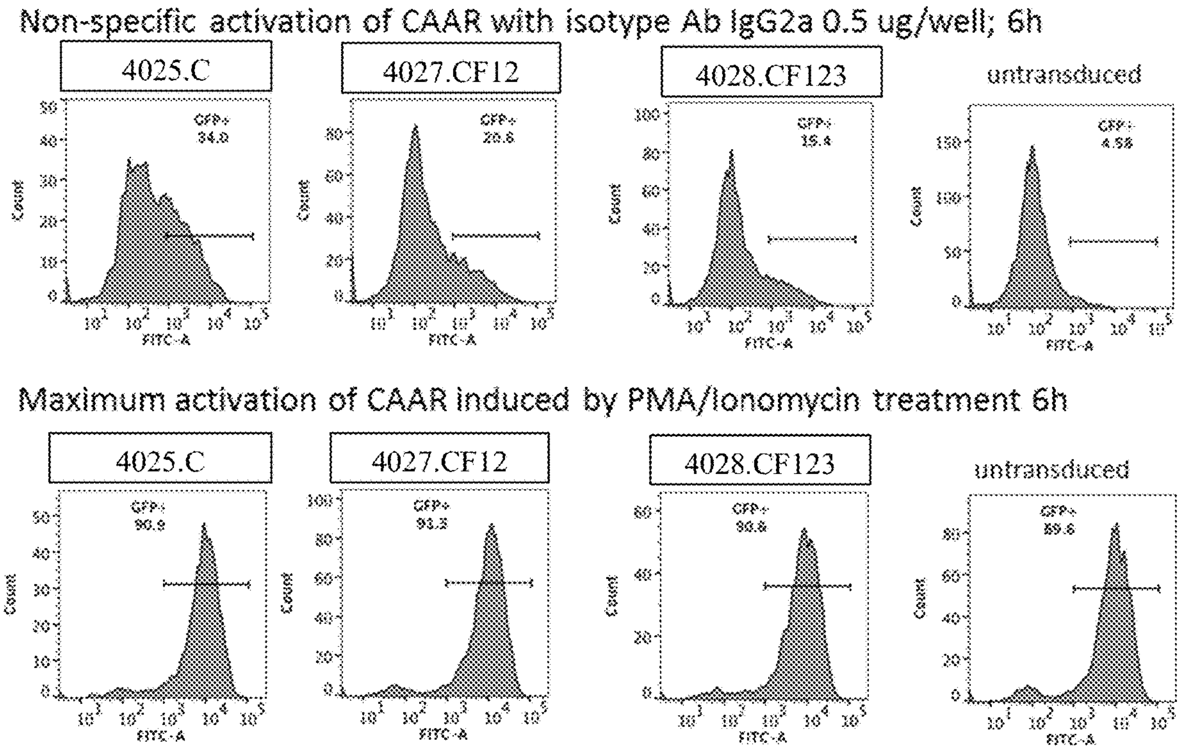
FIG. 5 is a series of flow cytometry plots showing the negative and positive controls for PLA2R CAAR T cell activation using an isotype control (top, negative control) or PMA+ionomycin (bottom, positive control).
Figure 6:
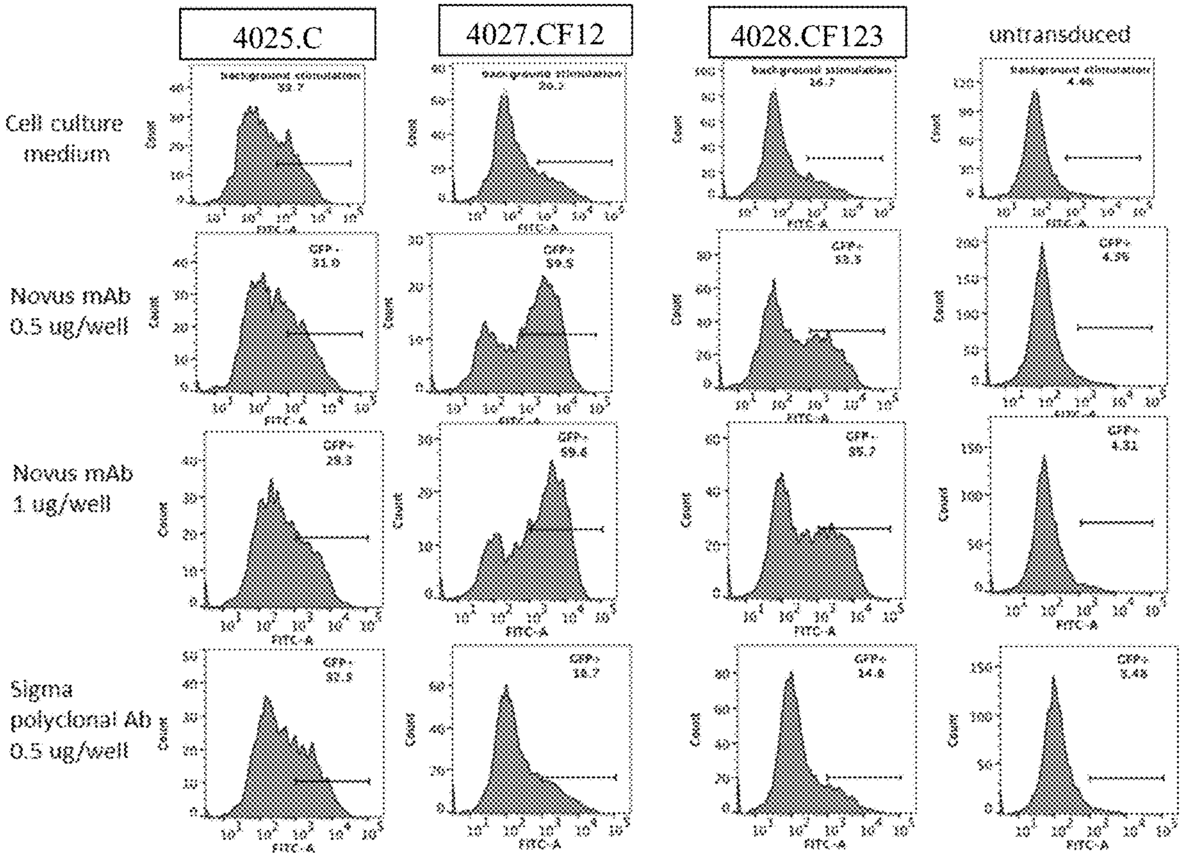
FIG. 6 is a series of flow cytometry plots showing the activation of 4027.CF12 and 4028.CF123 PLA2R CAAR T cells by plate-bound monoclonal or polyclonal antibodies specific for the PLA2R CTLD2 domain, measured as GFP expression by Jurkat NFAT-GFP cells (6 h activation). No evidence of T cell activation is seen in construct 4025.C, as expected as this construct does not contain the CTLD2 domain, and untransduced cells upon exposure to the anti-PLA2R monoclonal antibody (mAb) or the polyclonal anti-PLA2R antibody (Ab). Specific T cell activation in response to cross-linking of the PLA2R CAAR by the monoclonal anti-PLA2R mAb but not the polyclonal anti-PLA2R Ab is observed.

FIGS. 5 and 6 show T cell activation by GFP expression of Jurkat cells transduced with the indicated constructs. Negative and positive controls are shown in FIG. 5. Test samples are shown in FIG. 6.

Cells and antibodies were incubated at 37° C. for 6 hours. At the end of the 6 h, cells were examined for expression of NFAT-GFP as an indicator of T cell activation.

FIG. 5 depicts the negative and positive controls for PLA2R CAAR T cell activation using an isotype control (top, negative control) or PMA+ionomycin (bottom, positive control).

FIG. 6 illustrates the activation of PLA2R CAAR T cells by specific antibodies measured as GFP expression by Jurkat NFAT-GFP cells (6 h activation). No evidence of T cell activation is seen in construct 4025.C and untransduced cells upon exposure to the monoclonal anti-PLA2R Mab or the polyclonal anti-PLA2R Ab. Specific T cell activation in response to cross-linking by the monoclonal anti-PLA2R Ab but not the polyclonal anti-PLA2R Ab is seen using constructs 4027.CF12 and 4028.CF123.

Example 2

Six additional PLA2R CAAR constructs were designed and generated herein. Construct C was comprised of a cysteine rich domain, a CD8 hinge region, a CD8 transmembrane domain, a 4-1BB intracellular domain and CD3 zeta signaling domain (FIG. 2A, SEQ ID NOs: 25 & 26).

Construct CF1 was comprised of an extracellular domain comprising a cysteine rich domain, a fibronectin II domain, and a C-type lectin 1 domain. Construct CF1 also included a CD8 hinge region, a CD8 transmembrane domain, a 4-1BB intracellular domain and CD3 zeta signaling domain (FIG. 2B, SEQ ID NOs: 27 & 28).

Construct CF123 was comprised of an extracellular domain comprising a cysteine rich domain, a fibronectin II domain, a C-type lectin 1 domain, a C-type lectin 2 domain, and a C-type lectin 3 domain. Also included in construct CF123 was a GS linker, a CD8 transmembrane domain, a 4-1BB intracellular domain and CD3 zeta signaling domain (FIG. 2C, SEQ ID NOs: 29 & 30).

Construct CF1237 was comprised of an extracellular domain comprising a cysteine rich domain, a fibronectin II domain, a C-type lectin 1 domain, a C-type lectin 2 domain, a C-type lectin 3 domain and a C-type lectin 7 domain. Additionally included in construct CF1237 was a GS linker, a CD8 transmembrane domain, a 4-1BB intracellular domain and CD3 zeta signaling domain (FIG. 2D, SEQ ID NOs: 31 & 32).

Figure 7A:
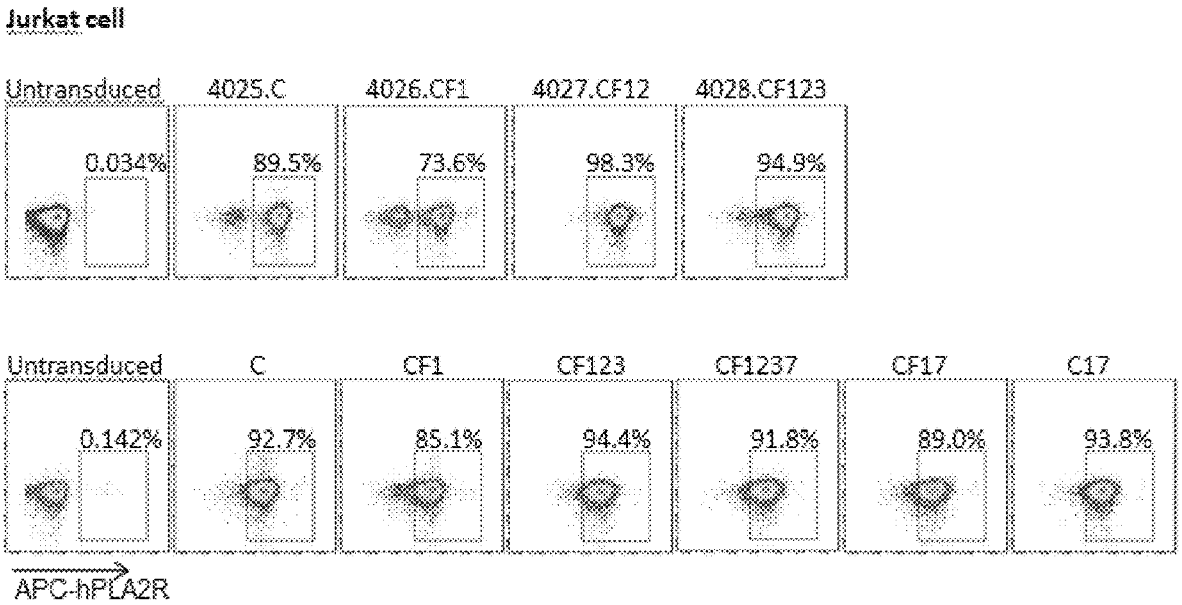
FIGS. 7A-7B are a series of plots illustrating that PLA2R MN patient IgG detects PLA2R CAAR expression on transduced Jurkat NFAT-GFP and primary human T cells. Flow cytometry plots demonstrate robust PLA2R CAAR surface expression on Jurkat NFAT-GFP cells (FIG. 7A) and primary human T cells (FIG. 7B) for all constructs evaluated (4025.C, 4026.CF1, 4027.CF12, 4028.CF123, C, CF1, CF123, CF1237, CF17, C17). The expression of PLA2R CAAR by Jurkat NFAT-GFP and primary human T cells transduced with different PLA2R lentiviral constructs (72 h) was detected by incubation with MN patient IgG followed by APC-conjugated anti-human IgG.

Construct CF17 was comprised of an extracellular domain comprising a cysteine rich domain, a fibronectin II domain, a C-type lectin 1 domain, and a C-type lectin 7 domain. Construct CF17 also included a GS linker, a CD8 transmembrane domain, a 4-1BB intracellular domain and CD3 zeta signaling domain (FIG. 7E, SEQ ID NOs: 33 & 34).

Construct C17 was comprised of an extracellular domain comprising a cysteine rich domain, a C-type lectin 1 domain, and a C-type lectin 7 domain. Construct C17 also included a GS linker, a CD8 transmembrane domain, a 4-1BB intracellular domain and CD3 zeta signaling domain (FIG. 7F, SEQ ID NOs: 35 & 36).

Figure 7B:
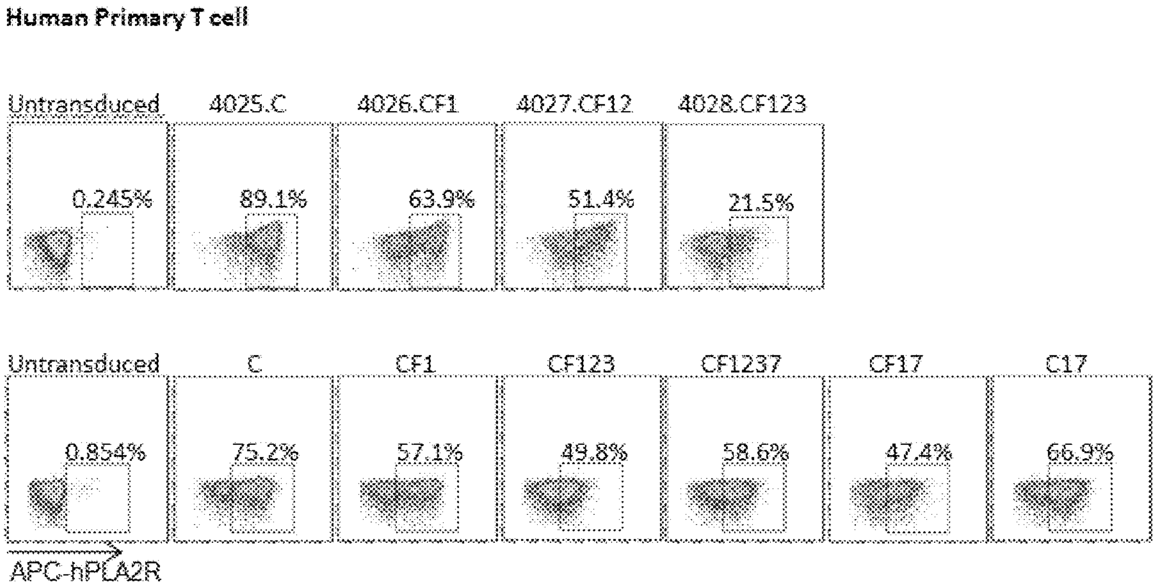

The various PLA2R CAAR constructs were transduced into Jurkat cells and primary human T cells. Surface expression of the PLA2R CAARs was assessed by flow cytometry using MN patient IgG, followed by APC-labeled anti-human IgG secondary antibody. All of the transduced Jurkat (FIG. 7A) and primary human T cells (FIG. 7B), but not the untransduced control cells, exhibited detectable surface expression of the CAAR constructs.

Figure 8:
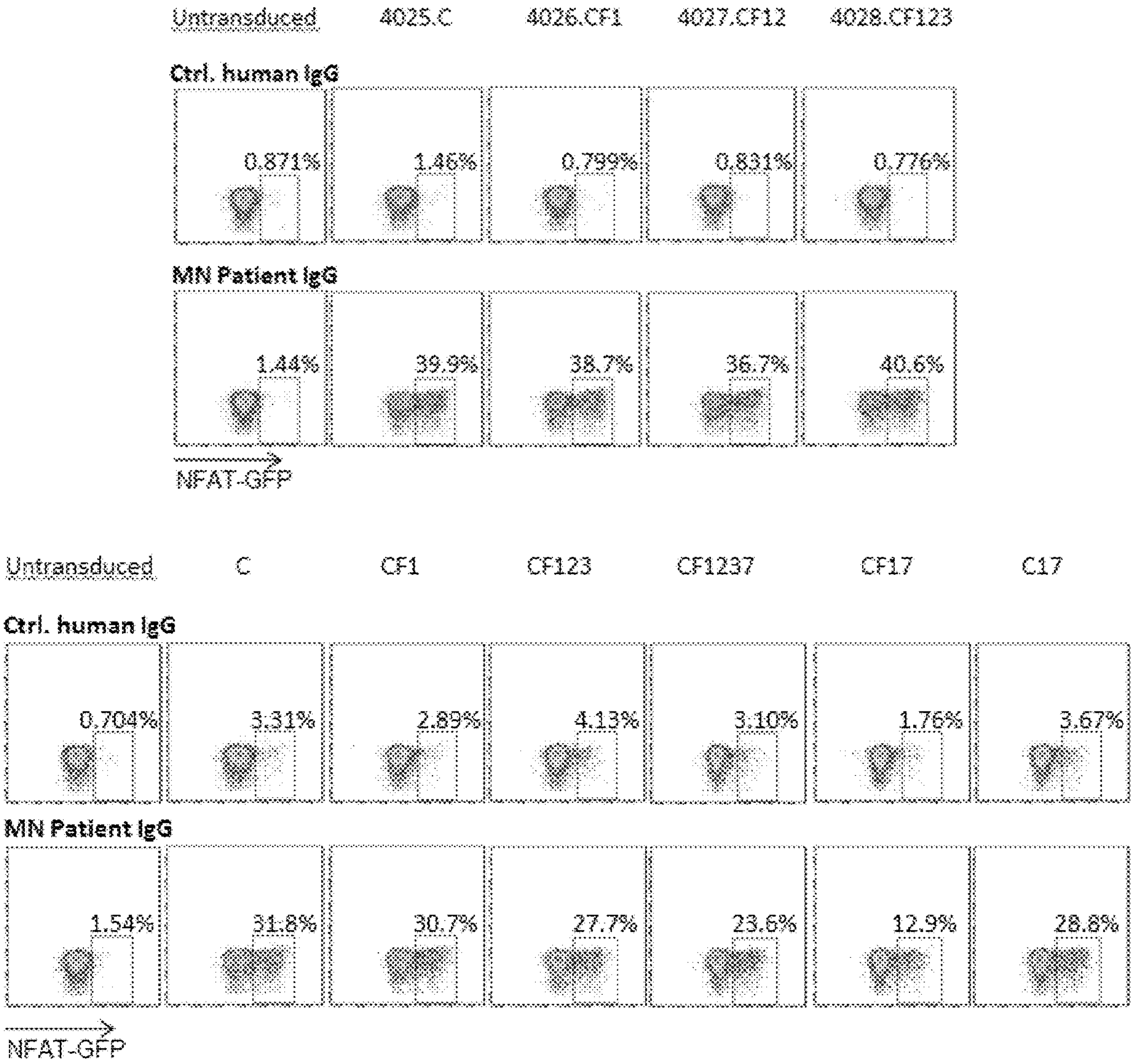
FIG. 8 is a series of plots illustrating that plate-bound MN patient IgG activates PLA2R CAAR transduced Jurkat-NFAT-GFP cells. Flow cytometry plots show the activation of PLA2R CAAR T cells by MN patient IgG measured as GFP expression by Jurkat NFAT-GFP cells (6 h activation). All evaluated PLA2R CAAR T cells (4025.C, 4026.CF1, 4027.CF12, 4028.CF123, C, CF1, CF123, CF1237, CF17, C17) transduced signal after cross-linking by plate-bound anti-PLA2R IgG.

To evaluate whether plate-bound anti-PLA2R IgG, which mimics the surface of an anti-PLA2R B cell, can lead to CAAR T cell activation, $5\times10^4$ Jurkat NFAT-GFP reporter cells were cultured for 6 h in 96-well plate coated with 10 μg/ml either MN patient IgG or control human IgG. Cells were then harvested for flow cytometry analysis. MN patient IgG, but not control human IgG activated Jurkat cells transduced with each of the 10 constructs (FIG. 8). No evidence of T cell activation was seen in untransduced Jurkat cells upon exposure to either MN patient IgG or control human IgG (FIG. 8). These studies indicate that CAAR signaling is activated upon target encounter.

To evaluate whether primary human PLA2R CAAR T cells can be activated by plate-bound anti-PLA2R IgG, PLA2R CAAR T cells were exposed to either plate-bound MN patient IgG or control human IgG for 24 h. IFN-γ secretion was measured by ELISA of culture supernatants. MN patient IgG stimulated markedly higher IFN-γ production compared to the control human IgG, reflecting primary human CAAR T cell activation after target engagement (FIG. 9).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. An isolated polynucleotide encoding a chimeric autoantibody receptor (CAAR), wherein the CAAR comprises:
(i) an extracellular domain comprising a phospholipase A2 receptor (PLA2R) autoantigen comprising the amino acid sequence of SEQ ID NO: 59;
(ii) a CD8 alpha chain transmembrane domain;
(iii) a 4-1BB intracellular domain; and
(iv) a CD3 zeta signaling domain.

2. The polynucleotide of claim 1, wherein the CD8 alpha chain transmembrane domain comprises the amino acid sequence of SEQ ID NO: 19.

3. The polynucleotide of claim 1, wherein the 4-1BB intracellular domain comprises the amino acid sequence of SEQ ID NO: 21.

4. The polynucleotide of claim 1, wherein the CD3 zeta signaling domain comprises the amino acid sequence of SEQ ID NO: 23 or SEQ ID NO: 45.

5. The polynucleotide of claim 1, wherein:
(i) the CD8 alpha chain transmembrane domain comprises the amino acid sequence of SEQ ID NO: 19;
(ii) the 4-1BB intracellular domain comprises the amino acid sequence of SEQ ID NO: 21; and
(iii) CD3 zeta signaling domain comprises the amino acid sequence of SEQ ID NO: 45.

6. A recombinant vector comprising the polynucleotide of claim 1.

7. A chimeric autoantibody receptor (CAAR) comprising:
(i) an extracellular domain comprising a phospholipase A2 receptor (PLA2R) autoantigen comprising the amino acid sequence of SEQ ID NO: 59;
(ii) a CD8 alpha chain transmembrane domain;
(iii) a 4-1BB intracellular domain; and
(iv) a CD3 zeta signaling domain.

8. The CAAR of claim 7, wherein the CD8 alpha chain transmembrane domain comprises the amino acid sequence of SEQ ID NO: 19.

9. The CAAR of claim 7, wherein the 4-1BB intracellular domain comprises the amino acid sequence of SEQ ID NO: 21.

10. The CAAR of claim 7, wherein the CD3 zeta signaling domain comprises the amino acid sequence of SEQ ID NO: 23 or SEQ ID NO: 45.

11. The CAAR of claim 7, wherein:
(i) the CD8 alpha chain transmembrane domain comprises the amino acid sequence of SEQ ID NO: 19;
(ii) the 4-1BB intracellular domain comprises the amino acid sequence of SEQ ID NO: 21; and
(iii) the CD3 zeta signaling domain comprises the amino acid sequence of SEQ ID NO: 45.

12. A genetically modified cell comprising thy: CAAR of claim 7.

13. A pharmaceutical composition comprising the polynucleotide of claim 1 and a pharmaceutically acceptable excipient.

14. A pharmaceutical composition comprising the genetically modified cell of claim 12 and a pharmaceutically acceptable excipient.

15. A method for treating an autoantibody-mediated kidney disease in a subject in need thereof, the method comprising administering to the subject an effective amount of the genetically modified cell of claim 12, thereby treating the autoantibody mediated kidney disease in the subject.

16. The method of claim 15, wherein the autoantibody mediated kidney disease is selected from the group consisting of a glomerular disease and a primary membranous nephropathy.

17. A method for reducing glomerulus damage in a subject at risk of or suffering from an autoantibody-mediated kidney disease, the method comprising administering to the subject an effective amount of the genetically modified cell of claim 12, thereby preventing or reducing glomerulus damage in the subject.

18. The method of claim 17, wherein the autoantibody mediated kidney disease is selected from the group consisting of a glomerular disease and a primary membranous nephropathy.

* * * * *